United States Patent
Toop et al.

(10) Patent No.: US 12,139,473 B2
(45) Date of Patent: Nov. 12, 2024

(54) SUBSTITUTED-N-HETEROARYL COMPOUNDS AND USES THEREOF

(71) Applicant: Bionomics Limited, Eastwood (AU)

(72) Inventors: Hamish Toop, Thebarton (AU); Dharam Paul, Thebarton (AU); Rajinder Singh, Thebarton (AU); Erin Smith, Thebarton (AU); Patrick Bazzini, Strasbourg (FR); Jean-Marie Contreras, Westhouse (FR); Christophe Morice, Widensolen (FR); Laurent Schaeffer, Fortschwihr (FR); Celine Michaut-Simon, Illkirch (FR); Florence Chery, Strasbourg (FR); Fabrice Garrido, Illkirch (FR)

(73) Assignee: Bionomics Limited, Eastwood (AU)

( * ) Notice: Subject to any disclaimer, the term of this patent is extended or adjusted under 35 U.S.C. 154(b) by 608 days.

(21) Appl. No.: 17/441,637

(22) PCT Filed: Oct. 30, 2019

(86) PCT No.: PCT/AU2019/051194
§ 371 (c)(1),
(2) Date: Sep. 21, 2021

(87) PCT Pub. No.: WO2020/000065
PCT Pub. Date: Jan. 2, 2020

(65) Prior Publication Data
US 2022/0112176 A1   Apr. 14, 2022

(30) Foreign Application Priority Data
Mar. 25, 2019 (AU) .................. 2019900992

(51) Int. Cl.
*C07D 403/04* (2006.01)
*C07D 401/14* (2006.01)
*C07D 405/14* (2006.01)

(52) U.S. Cl.
CPC ......... *C07D 403/04* (2013.01); *C07D 401/14* (2013.01); *C07D 405/14* (2013.01)

(58) Field of Classification Search
CPC .................................................. C07D 403/14
See application file for complete search history.

(56) References Cited

U.S. PATENT DOCUMENTS 6,479,435 B1 * 11/2002 Pulman .................. A01N 33/22
544/333

FOREIGN PATENT DOCUMENTS

WO   WO-2012076877 A1 *   6/2012   ......... A61K 31/4178

* cited by examiner

*Primary Examiner* — Golam M Shameem
(74) *Attorney, Agent, or Firm* — Weaver Austin Villeneuve & Sampson LLP

(57) ABSTRACT

Activators of Kv3.1 and/or Kv3.2 channels which are therapeutically useful in the treatment of cognitive dysfunction and the negative symptoms which are associated with central nervous system disorders such as schizophrenia, Alzheimer's disease, Tourette's syndrome, autism, dementia, epilepsy and other disorders where gamma oscillations are dysfunctional are provided. The activators include substituted N-heteroaryl compounds.

14 Claims, No Drawings

SUBSTITUTED-N-HETEROARYL COMPOUNDS AND USES THEREOF

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

FIELD

The present disclosure relates generally to compounds useful for the treatment and/or enhancement of cognitive function and negative symptoms associated with central nervous system disorders where the circuitry involving fast spiking PV+ interneurons and the production of cortical gamma oscillations is disrupted. The subject disclosure enables the manufacture of medicaments as well as compositions containing same for use in methods of therapy and prophylaxis of cognitive dysfunction and negative symptoms.

BACKGROUND OF THE INVENTION

The Kv3 voltage-gated potassium channels Kv3.1-Kv3.4, encoded by the KCNC1-4 genes, are responsible for the neurons ability for fast repolarization, thereby facilitating high-frequency action potential firing. Due to these fast activating properties, Kv3 channels are believed to be important in setting and controlling firing frequency in fast spiking neurons. Hence the Kv3 channels are thought to play a pivotal role in cortical neuronal networks to produce synchronized gamma (γ) frequency oscillations (30-80 Hz). When synchronized across neuronal populations, these γ oscillations are associated with productive cognitive and behavioral responses; their dysfunction is thought to be relevant for cognitive disorders and negative symptoms. Specifically, the fast-spiking interneurons involved in generating gamma synchrony are those that express the calcium-binding protein, parvalbumin (PV).

The Kv3.1 and Kv3.2 subunits are predominately expressed in PV positive fast spiking GABAergic interneurons and are involved in the rapid action potential firing of these interneurons to orchestrate the activity of cortical networks.

Studies in patients suffering from schizophrenia and in animal models of the condition, have shown an inability of cortical networks to generate coherent gamma frequency oscillations. In addition, post-mortem studies using cortical tissue obtained from patients with schizophrenia report reductions in PV and in the expression of Kv3.1 channels in the remaining PV positive interneurons. In addition, PV interneuron dysfunction leading to dysfunctional gamma oscillations is implicated in several pathologies associated with cognitive dysfunction and negative symptoms where the circuitry involving fast spiking PV+ interneurons and the production of cortical gamma oscillations is disrupted: schizophrenia, Alzheimer's disease, Tourette's syndrome, autism, dementia, epilepsy.

Hence, pharmacological manipulation of Kv3.1 and/or Kv3.2 channels, represents a possible method for treating cognitive dysfunction and negative symptoms associated with central nervous system disorders where the circuitry involving fast spiking PV+ interneurons and the production of cortical gamma oscillations is dysfunctional. Small molecules that positively modulate Kv3.1 and/or Kv3.2, by restoring fast-spiking properties to PV interneurons, represent a novel therapeutic treatment for cognitive dysfunction and negative symptoms.

SUMMARY

The instant disclosure teaches that compounds of the invention including subformulae thereof, are activators of Kv3.1 and/or Kv3.2 channels and are therefore therapeutically useful in the treatment of cognitive dysfunction and negative symptoms associated with central nervous system disorders such as schizophrenia, Alzheimer's disease, Tourette's syndrome, autism, dementia, epilepsy and other disorders where gamma oscillations are dysfunctional.

In an aspect the invention provides a compound of formula (I):

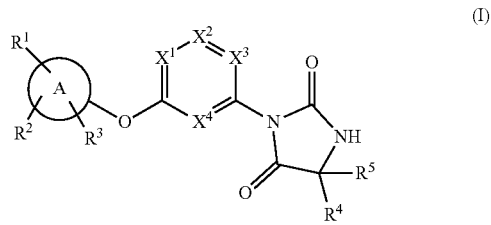

wherein:
$X^1$ and $X^4$ are both N and $X^2$ and $X^3$ are independently CR; or
$X^1$ and $X^3$ are both N and $X^2$ and $X^4$ are independently CR; or
$X^3$ and $X^4$ are both N and $X^1$ and $X^2$ are independently CR; or
$X^1$ and $X^2$ are both N and $X^3$ and $X^4$ are independently CR; or
$X^2$ and $X^3$ are both N and $X^1$ and $X^4$ are independently CR; or
$X^2$ and $X^4$ are both N and $X^1$ and $X^3$ are independently CR; or
$X^1$, $X^3$ and $X^4$ are N and $X^2$ is CR; or
$X^1$, $X^2$ and $X^4$ are N and $X^3$ is CR; or
$X^2$, $X^3$ and $X^4$ are N and $X^1$ is CR; and
Ring A is phenyl or pyridinyl;
$R^1$ is H, CN, halo, $OCF_3$, optionally substituted $C_1$-$C_5$ alkoxy, optionally substituted $C_1$-$C_5$ alkyl, optionally substituted aryl or optionally substituted heteroaryl;
$R^2$ and $R^3$ are independently H, CN, halo, optionally substituted $C_1$-$C_5$ alkyl or optionally substituted $C_1$-$C_5$ alkoxy; or
$R^2$ and $R^3$ together represent an optionally substituted 5- or 6-membered O, N or S-containing heterocyclyl; and
$R^4$ and $R^5$ are independently H, optionally substituted $C_1$-$C_4$ alkyl or optionally substituted $C_1$-$C_4$ haloalkyl; or
$R^4$ and $R^5$ together represent an optionally substituted 3-, 4-, 5-, 6- or 7-membered cycloalkyl or optionally substituted 3-, 4-, 5-, 6- or 7-membered heterocyclyl; and
R is selected from H, halo, $C_1$-$C_3$ haloalkyl, $C_1$-$C_5$ alkoxy or $C_1$-$C_5$ alkyl;
or a pharmaceutically acceptable salt, solvate or prodrug thereof, and stereoisomer thereof.

In an aspect the invention provides a compound of formula (II):

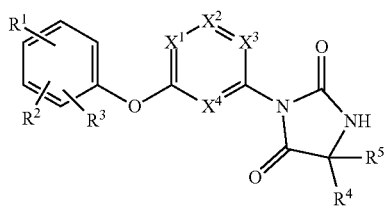

(II)

wherein:
$X^1$ and $X^4$ are both N and $X^2$ and $X^3$ are independently CR; or
$X^1$ and $X^3$ are both N and $X^2$ and $X^4$ are independently CR; or
$X^3$ and $X^4$ are both N and $X^1$ and $X^2$ are independently CR; or
$X^1$ and $X^2$ are both N and $X^3$ and $X^4$ are independently CR; or
$X^2$ and $X^3$ are both N and $X^1$ and $X^4$ are independently CR; or
$X^2$ and $X^4$ are both N and $X^1$ and $X^3$ are independently CR; or
$X^1$, $X^3$ and $X^4$ are N and $X^2$ is CR; or
$X^1$, $X^2$ and $X^4$ are N and $X^3$ is CR; or
$X^2$, $X^3$ and $X^4$ are N and $X^1$ is CR; and
$R^1$ is H, CN, halo, $OCF_3$, optionally substituted $C_1$-$C_5$ alkoxy, optionally substituted $C_1$-$C_5$ alkyl, optionally substituted aryl or optionally substituted heteroaryl;
$R^2$ and $R^3$ are independently H, CN, halo, optionally substituted $C_1$-$C_5$ alkyl or optionally substituted $C_1$-$C_5$ alkoxy; or
$R^2$ and $R^3$ together represent an optionally substituted 5- or 6-membered O, N, S-containing heterocyclyl; and
$R^4$ and $R^5$ are independently H, optionally substituted $C_1$-$C_4$ alkyl or optionally substituted $C_1$-$C_4$ haloalkyl; or
$R^4$ and $R^5$ together represent an optionally substituted 3-, 4-, 5-, 6- or 7-membered cycloalkyl or or optionally substituted 3-, 4-, 5-, 6- or 7-membered heterocyclyl; and
R is selected from H, halo, $C_1$-$C_3$ haloalkyl, $C_1$-$C_5$ alkoxy or $C_1$-$C_5$ alkyl;
or a pharmaceutically acceptable salt, solvate or prodrug thereof, and stereoisomer thereof.

In an embodiment the compound of formula (II) is a compound of formula (IIa), (IIb), or (IIc):

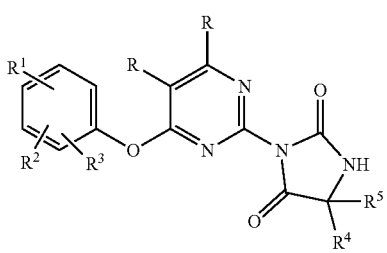

(IIa)

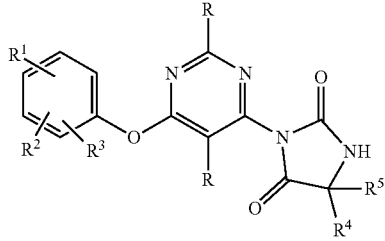

(IIb)

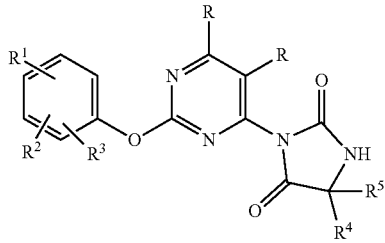

(IIc)

wherein R and $R^1$ to $R^5$ are as defined above.

In an embodiment the compound of formula (II) is a compound of formula (IId), (IIe), or (IIf):

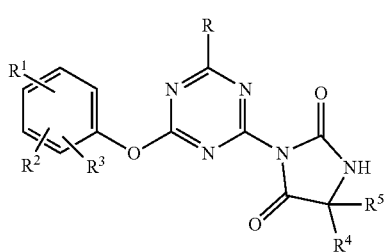

(IId)

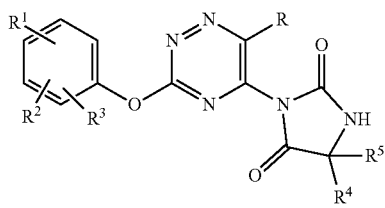

(IIe)

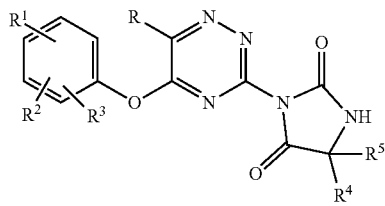

(IIf)

wherein R and $R^1$ to $R^5$ are as defined above.

In a further aspect there is provided methods for enhancing cognition in a subject in need thereof, the method comprising the step of administering an effective amount of a compound of formula (I) or pharmaceutically acceptable salt, solvate or prodrug thereof, and stereoisomer thereof:

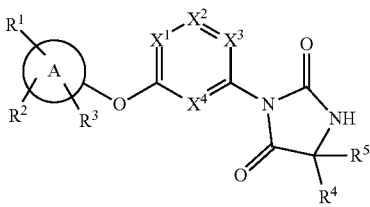

(I)

wherein:
at least one of $X^1$, $X^2$, $X^3$ or $X^4$ is N and the others are independently CR;
Ring A is phenyl or pyridinyl;
$R^1$ is H, CN, halo, $OCF_3$, optionally substituted $C_1$-$C_5$ alkoxy, optionally substituted $C_1$-$C_5$ alkyl, optionally substituted aryl or optionally substituted heteroaryl;
$R^2$ and $R^3$ are independently H, CN, halo, optionally substituted $C_1$-$C_5$ alkyl or optionally substituted $C_1$-$C_5$ alkoxy; or
$R^2$ and $R^3$ together represent an optionally substituted 5- or 6-membered O, N, S-containing heterocyclyl; and
$R^4$ and $R^5$ are independently H, optionally substituted $C_1$-$C_4$ alkyl or optionally substituted $C_1$-$C_4$ haloalkyl; or
$R^4$ and $R^5$ together represent an optionally substituted 3-, 4-, 5-, 6- or 7-membered cycloalkyl or or optionally substituted 3-, 4-, 5-, 6- or 7-membered heterocyclyl; and
R is selected from H, halo, $C_1$-$C_3$ haloalkyl, $C_1$-$C_5$ alkoxy or $C_1$-$C_5$ alkyl.

In another aspect, the method for enhancing cognition in a subject in need thereof comprises the step of administering an effective amount of a compound of formula (II) or pharmaceutically acceptable salt, solvate or prodrug thereof, and stereoisomer thereof:

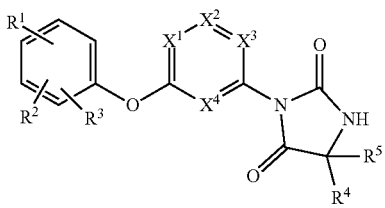

(II)

wherein:
at least one of $X^1$, $X^2$, $X^3$ or $X^4$ is N and the others are independently CR;
$R^1$ is H, CN, halo, $OCF_3$, optionally substituted $C_1$-$C_5$ alkoxy, optionally substituted $C_1$-$C_5$ alkyl, optionally substituted aryl or optionally substituted heteroaryl;
$R^2$ and $R^3$ are independently H, CN, halo, optionally substituted $C_1$-$C_5$ alkyl or optionally substituted $C_1$-$C_5$ alkoxy; or
$R^2$ and $R^3$ together represent an optionally substituted 5- or 6-membered O, N, S-containing heterocyclyl; $R^4$ and $R^5$ are independently H, optionally substituted $C_1$-$C_4$ alkyl or optionally substituted $C_1$-$C_4$ haloalkyl; or
$R^4$ and $R^5$ together represent an optionally substituted 3-, 4-, 5-, 6- or 7-membered cycloalkyl or or optionally substituted 3-, 4-, 5-, 6- or 7-membered heterocyclyl; and
R is selected from H, halo, $C_1$-$C_3$ haloalkyl, $C_1$-$C_5$ alkoxy or $C_1$-$C_5$ alkyl.

The present invention also provides methods for treating cognitive dysfuntion and negative symptoms comprising the step of administering to a patient in need thereof a compound of formula (I) or a pharmaceutically acceptable salt, solvate or prodrug thereof, and stereoisomer thereof:

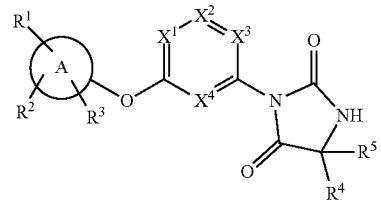

(I)

wherein:
at least one of $X^1$, $X^2$, $X^3$ or $X^4$ is N and the others are independently CR; Ring A is phenyl or pyridinyl;
$R^1$ is H, CN, halo, $OCF_3$, optionally substituted $C_1$-$C_5$ alkoxy, optionally substituted $C_1$-$C_5$ alkyl, optionally substituted aryl or optionally substituted heteroaryl;
$R^2$ and $R^3$ are independently H, CN, halo, optionally substituted $C_1$-$C_5$ alkyl or optionally substituted $C_1$-$C_5$ alkoxy; or
$R^2$ and $R^3$ together represent an optionally substituted 5- or 6-membered O, N, S-containing heterocyclyl; and
$R^4$ and $R^5$ are independently H, optionally substituted $C_1$-$C_4$ alkyl or optionally substituted $C_1$-$C_4$ haloalkyl; or
$R^4$ and $R^5$ together represent an optionally substituted 3-, 4-, 5-, 6- or 7-membered cycloalkyl or or optionally substituted 3-, 4-, 5-, 6- or 7-membered heterocyclyl; and
R is selected from H, halo, $C_1$-$C_3$ haloalkyl, $C_1$-$C_5$ alkoxy or $C_1$-$C_5$ alkyl.

The present invention also provides methods for treating cognitive dysfuntion and negative symptoms comprises the step of administering to a patient in need thereof a compound of formula (II) or a pharmaceutically acceptable salt, solvate or prodrug thereof, and stereoisomer thereof:

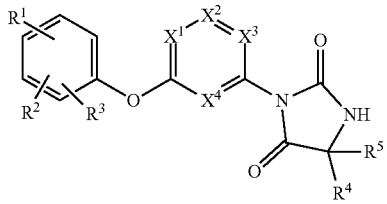

(II)

wherein:
at least one of $X^1$, $X^2$, $X^3$ or $X^4$ is N and the others are independently CR;
$R^1$ is H, CN, halo, $OCF_3$, optionally substituted $C_1$-$C_5$ alkoxy, optionally substituted $C_1$-$C_5$ alkyl, optionally substituted aryl or optionally substituted heteroaryl;
$R^2$ and $R^3$ are independently H, CN, halo, optionally substituted $C_1$-$C_5$ alkyl or optionally substituted $C_1$-$C_5$ alkoxy; or
$R^2$ and $R^3$ together represent an optionally substituted 5- or 6-membered O, N, S-containing heterocyclyl;

$R^4$ and $R^5$ are independently H, optionally substituted $C_1$-$C_4$ alkyl or optionally substituted $C_1$-$C_4$ haloalkyl; or $R^4$ and $R^5$ together represent an optionally substituted 3-, 4-, 5-, 6- or 7-membered cycloalkyl or or optionally substituted 3-, 4-, 5-, 6- or 7-membered heterocyclyl; and R is selected from H, halo, $C_1$-$C_3$ haloalkyl, $C_1$-$C_5$ alkoxy or $C_1$-$C_5$ alkyl.

The present invention also provides the use of a compound of formula (I) or a pharmaceutically acceptable salt, solvate or prodrug thereof, and stereoisomer thereof:

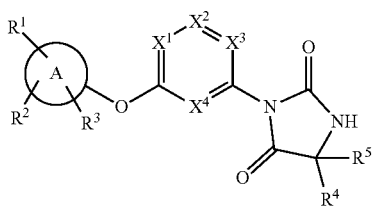

(I)

wherein:
at least one of $X^1$, $X^2$, $X^3$ or $X^4$ is N and the others are independently CR; Ring A is phenyl or pyridinyl;

$R^1$ is H, CN, halo, $OCF_3$, optionally substituted $C_1$-$C_5$ alkoxy, optionally substituted $C_1$-$C_5$ alkyl, optionally substituted aryl or optionally substituted heteroaryl;

$R^2$ and $R^3$ are independently H, CN, halo, optionally substituted $C_1$-$C_5$ alkyl or optionally substituted $C_1$-$C_5$ alkoxy; or $R^2$ and $R^3$ together represent an optionally substituted 5- or 6-membered O, N, S-containing heterocyclyl; and $R^4$ and $R^5$ are independently H, optionally substituted $C_1$-$C_4$ alkyl or optionally substituted $C_1$-$C_4$ haloalkyl; or $R^4$ and $R^5$ together represent an optionally substituted 3-, 4-, 5-, 6- or 7-membered cycloalkyl or or optionally substituted 3-, 4-, 5-, 6- or 7-membered heterocyclyl; and R is selected from H, halo, $C_1$-$C_3$ haloalkyl, $C_1$-$C_5$ alkoxy or $C_1$-$C_5$ alkyl; in the manufacture of a medicament for enhancing cognition in a subject in need thereof.

The invention provides the use of a compound of formula (II) or a pharmaceutically acceptable salt, solvate or prodrug thereof, and stereoisomer thereof:

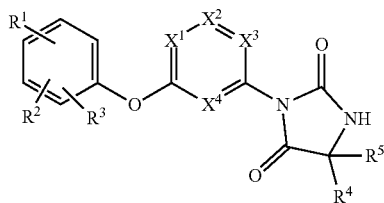

(II)

wherein:
at least one of $X^1$, $X^2$, $X^3$ or $X^4$ is N and the others are independently CR;

$R^1$ is H, CN, halo, $OCF_3$, optionally substituted $C_1$-$C_5$ alkoxy, optionally substituted $C_1$-$C_5$ alkyl, optionally substituted aryl or optionally substituted heteroaryl;

$R^2$ and $R^3$ are independently H, CN, halo, optionally substituted $C_1$-$C_5$ alkyl or optionally substituted $C_1$-$C_5$ alkoxy; or $R^2$ and $R^3$ together represent an optionally substituted 5- or 6-membered O, N, S-containing heterocyclyl;

$R^4$ and $R^5$ are independently H, optionally substituted $C_1$-$C_4$ alkyl or optionally substituted $C_1$-$C_4$ haloalkyl; or $R^4$ and $R^5$ together represent an optionally substituted 3-, 4-, 5-, 6- or 7-membered cycloalkyl or optionally substituted 3-, 4-, 5-, 6- or 7-membered heterocyclyl; and R is selected from H, halo, $C_1$-$C_3$ haloalkyl, $C_1$-$C_5$ alkoxy or $C_1$-$C_5$ alkyl; in the manufacture of a medicament for enhancing cognition in a subject in need thereof.

The present invention also provides the use of a compound of formula (I) or a pharmaceutically acceptable salt, solvate or prodrug thereof, and stereoisomer thereof:

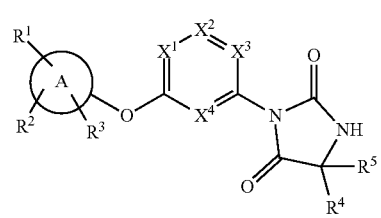

(I)

wherein:
at least one of $X^1$, $X^2$, $X^3$ or $X^4$ is N and the others are independently CR; Ring A is phenyl or pyridinyl;

$R^1$ is H, CN, halo, $OCF_3$, optionally substituted $C_1$-$C_5$ alkoxy, optionally substituted $C_1$-$C_5$ alkyl, optionally substituted aryl or optionally substituted heteroaryl;

$R^2$ and $R^3$ are independently H, CN, halo, optionally substituted $C_1$-$C_5$ alkyl or optionally substituted $C_1$-$C_5$ alkoxy; or $R^2$ and $R^3$ together represent an optionally substituted 5- or 6-membered O, N, S-containing heterocyclyl; and $R^4$ and $R^5$ are independently H, optionally substituted $C_1$-$C_4$ alkyl or optionally substituted $C_1$-$C_4$ haloalkyl; or $R^4$ and $R^5$ together represent an optionally substituted 3-, 4-, 5-, 6- or 7-membered cycloalkyl or optionally substituted 3-, 4-, 5-, 6- or 7-membered heterocyclyl; and R is selected from H, halo, $C_1$-$C_3$ haloalkyl, $C_1$-$C_5$ alkoxy or $C_1$-$C_5$ alkyl;

in the manufacture of a medicament for the treatment of cognitive dysfunction and negative symptoms associated with CNS disorders where the circuitry involving fast spiking PV+ interneurons and the production of cortical gamma oscillations is disrupted.

The invention provides the use of a compound of formula (II) or a pharmaceutically acceptable salt, solvate or prodrug thereof, and stereoisomer thereof:

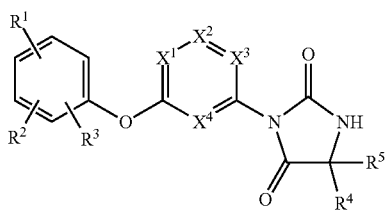

(II)

wherein:
at least one of $X^1$, $X^2$, $X^3$ or $X^4$ is N and the others are independently CR;
$R^1$ is H, CN, halo, $OCF_3$, optionally substituted $C_1$-$C_5$ alkoxy, optionally substituted $C_1$-$C_5$ alkyl, optionally substituted aryl or optionally substituted heteroaryl;
$R^2$ and $R^3$ are independently H, CN, halo, optionally substituted $C_1$-$C_5$ alkyl or optionally substituted $C_1$-$C_5$ alkoxy; or
$R^2$ and $R^3$ together represent an optionally substituted 5- or 6-membered O, N, S-containing heterocyclyl;
$R^4$ and $R^5$ are independently H, optionally substituted $C_1$-$C_4$ alkyl or optionally substituted $C_1$-$C_4$ haloalkyl; or
$R^4$ and $R^5$ together represent an optionally substituted 3-, 4-, 5-, 6- or 7-membered cycloalkyl or optionally substituted 3-, 4-, 5-, 6- or 7-membered heterocyclyl; and
R is selected from H, halo, $C_1$-$C_3$ haloalkyl, $C_1$-$C_5$ alkoxy or $C_1$-$C_5$ alkyl; in the manufacture of a medicament for the treatment of cognitive dysfunction and negative symptoms associated with CNS disorders where the circuitry involving fast spiking PV+ interneurons and the production of cortical gamma oscillations is disrupted.

The present invention also provides the use of a compound of formula (I) or a pharmaceutically acceptable salt, solvate or prodrug thereof, and stereoisomer thereof:

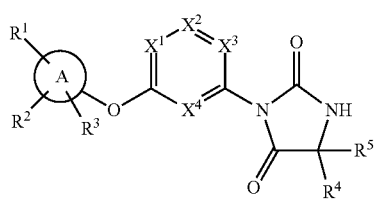

(I)

wherein:
at least one of $X^1$, $X^2$, $X^3$ or $X^4$ is N and the others are independently CR; Ring A is phenyl or pyridinyl;
$R^1$ is H, CN, halo, $OCF_3$, optionally substituted $C_1$-$C_5$ alkoxy, optionally substituted $C_1$-$C_5$ alkyl, optionally substituted aryl or optionally substituted heteroaryl;
$R^2$ and $R^3$ are independently H, CN, halo, optionally substituted $C_1$-$C_5$ alkyl or optionally substituted $C_1$-$C_5$ alkoxy; or
$R^2$ and $R^3$ together represent an optionally substituted 5- or 6-membered O, N, S-containing heterocyclyl; and
$R^4$ and $R^5$ are independently H, optionally substituted $C_1$-$C_4$ alkyl or optionally substituted $C_1$-$C_4$ haloalkyl; or
$R^4$ and $R^5$ together represent an optionally substituted 3-, 4-, 5-, 6- or 7-membered cycloalkyl or optionally substituted 3-, 4-, 5-, 6- or 7-membered heterocyclyl;

R is selected from H, halo, $C_1$-$C_3$ haloalkyl, $C_1$-$C_5$ alkoxy or $C_1$-$C_5$ alkyl; for enhancing cognition in a subject in need thereof.

The invention provides the use of a compound of formula (II) or a pharmaceutically acceptable salt, solvate or prodrug thereof, and stereoisomer thereof:

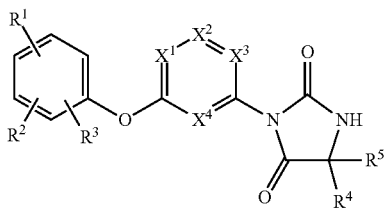

(II)

wherein:
at least one of $X^1$, $X^2$, $X^3$ or $X^4$ is N and the others are independently CR;
$R^1$ is H, CN, halo, $OCF_3$, optionally substituted $C_1$-$C_5$ alkoxy, optionally substituted $C_1$-$C_5$ alkyl, optionally substituted aryl or optionally substituted heteroaryl;
$R^2$ and $R^3$ are independently H, CN, halo, optionally substituted $C_1$-$C_5$ alkyl or optionally substituted $C_1$-$C_5$ alkoxy; or
$R^2$ and $R^3$ together represent an optionally substituted 5- or 6-membered O, N, S-containing heterocyclyl;
$R^4$ and $R^5$ are independently H, optionally substituted $C_1$-$C_4$ alkyl or optionally substituted $C_1$-$C_4$ haloalkyl; or
$R^4$ and $R^5$ together represent an optionally substituted 3-, 4-, 5-, 6- or 7-membered cycloalkyl or optionally substituted 3-, 4-, 5-, 6- or 7-membered heterocyclyl; and
R is selected from H, halo, $C_1$-$C_3$ haloalkyl, $C_1$-$C_5$ alkoxy or $C_1$-$C_5$ alkyl; for enhancing cognition in a subject in need thereof.

The present invention also provides the use of a compound of formula (I) or a pharmaceutically acceptable salt, solvate or prodrug thereof, and stereoisomer thereof:

(I)

wherein:
at least one of $X^1$, $X^2$, $X^3$ or $X^4$ is N and the others are independently CR; Ring A is phenyl or pyridinyl;
$R^1$ is H, CN, halo, $OCF_3$, optionally substituted $C_1$-$C_5$ alkoxy, optionally substituted $C_1$-$C_5$ alkyl, optionally substituted aryl or optionally substituted heteroaryl;
$R^2$ and $R^3$ are independently H, CN, halo, optionally substituted $C_1$-$C_5$ alkyl or optionally substituted $C_1$-$C_5$ alkoxy; or
$R^2$ and $R^3$ together represent an optionally substituted 5- or 6-membered O, N, S-containing heterocyclyl; and
$R^4$ and $R^5$ are independently H, optionally substituted $C_1$-$C_4$ alkyl or optionally substituted $C_1$-$C_4$ haloalkyl; or R[4] and R[5] together represent an optionally substituted 3-, 4-, 5-, 6- or 7-membered cycloalkyl or optionally substituted 3-, 4-, 5-, 6- or 7-membered heterocyclyl; and R is selected from H, halo, $C_1$-$C_3$ haloalkyl, $C_1$-$C_5$ alkoxy or $C_1$-$C_5$ alkyl;

for the treatment of cognitive dysnfunction and negative symptoms associated with CNS disorders where the circuitry involving fast spiking PV+ interneurons and the production of cortical gamma oscillations is disrupted.

The invention provides the use of a compound of formula (II) or a pharmaceutically acceptable salt, solvate or prodrug thereof, and stereoisomer thereof:

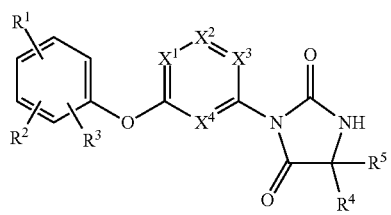

(II)

wherein:
at least one of $X^1$, $X^2$, $X^3$ or $X^4$ is N and the others are independently CR;

$R^1$ is H, CN, halo, $OCF_3$, optionally substituted $C_1$-$C_5$ alkoxy, optionally substituted $C_1$-$C_5$ alkyl, optionally substituted aryl or optionally substituted heteroaryl;

$R^2$ and $R^3$ are independently H, CN, halo, optionally substituted $C_1$-$C_5$ alkyl or optionally substituted $C_1$-$C_5$ alkoxy; or $R^2$ and $R^3$ together represent an optionally substituted 5- or 6-membered O, N, S-containing heterocyclyl;

$R^4$ and $R^5$ are independently H, optionally substituted $C_1$-$C_4$ alkyl or optionally substituted $C_1$-$C_4$ haloalkyl; or $R^4$ and $R^5$ together represent an optionally substituted 3-, 4-, 5-, 6- or 7-membered cycloalkyl or optionally substituted 3-, 4-, 5-, 6- or 7-membered heterocyclyl; and R is selected from H, halo, $C_1$-$C_3$ haloalkyl, $C_1$-$C_5$ alkoxy or $C_1$-$C_5$ alkyl;

for the treatment of cognitive dysnfunction and negative symptoms associated with CNS disorders where the circuitry involving fast spiking PV+ interneurons and the production of cortical gamma oscillations is disrupted.

DETAILED DESCRIPTION OF THE INVENTION

The present disclosure contemplates the treatment of cognitive dysfunction and negative symptoms associated with CNS disorders where the circuitry involving fast spiking PV+ interneurons and the production of cortical gamma oscillations is disrupted It is proposed herein that the compounds of formula (I) and subformulae thereof treat, negative symptoms associated with CNS disorders where the circuitry involving fast spiking PV+ interneurons and the production of cortical gamma oscillations is disrupted The invention is based on the discovery that particular 1,3 meta-disposed hydantoin substituted N-heteroaryl compounds of the general formula (I), (II) and/or (III) as shown below,

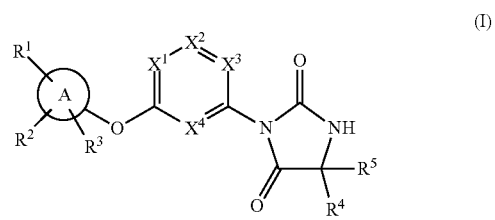

(I)

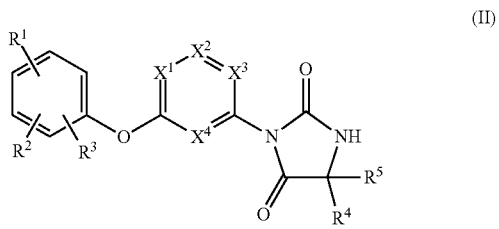

(II)

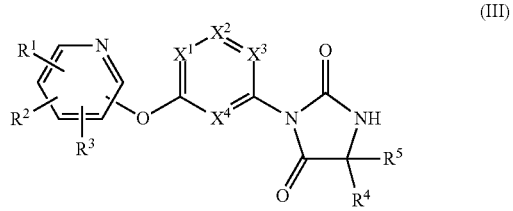

(III)

have useful properties as activators of the Kv3.1 and/or Kv3.2 channel and are able to elicit an effect on the central nervous system. In particular, the N-heteroaryl compounds are pyrimidinyl or triazinyl derivatives. Such compounds have significant potential for the treatment of a variety of cognitive dysfunctions and negative symptoms associated with CNS disorders where the circuitry involving fast spiking PV+ interneurons and the production of cortical gamma oscillations is disrupted. For example, schizophrenia, Alzheimer's disease, Tourette's syndrome, autism, epilepsy and other dementias. The compounds show unexpected superior in vivo activity relative to comparable 1,4-para-disposed derivatives.

Cognitive dysfunction or impairment refers to a category of mental health disorders that primarily affect cognitive abilities including learning, memory, perception, and problem solving. They are defined by deficits in cognitive ability that are acquired (as opposed to developmental), typically represent decline, and may have an underlying brain pathology. The instant compounds have been shown to treat a specific underlying pathology ie "where the circuitry involving fast spiking PV+ interneurons and the production of cortical gamma oscillations is disrupted".

The DSM-5 defines six key domains of cognitive function: executive function, learning and memory, perceptual-motor function, language, complex attention, and social cognition. Cognition dysfunction or impairment may be diagnosed and assessed based on the six-item cognitive impairment test (6-CIT) Kingshill Version 2000.

"Alkyl" refers to a saturated monovalent hydrocarbon radical which may be straight chained or branched and preferably have from 1 to 5 carbon atoms or more preferably 1 (i.e., for instance $C_1$-$C_4$ alkyl). Examples of such alkyl groups include methyl, ethyl, n-propyl, iso-propyl, n-butyl and iso-butyl. Unless otherwise specified, "cycloalkyl" are also included within this definition and refers to cyclic alkyl groups having a single cyclic ring or multiple condensed rings. Such cycloalkyl groups include, by way of example, single ring structures such as cyclopropyl, cyclobutyl, cyclopentyl, cyclohexyl, cyclooctyl, and the like.

"Alkoxy" refers to the group alkyl-O— where the alkyl group is as described above but restricted to $C_1$-$C_5$ alkoxy. Examples include methoxy, ethoxy and n-propoxy. Cyclyl groups, for example, cyclopropylmethoxy, are also included within the scope.

"Halo" or "halogen" refers to fluoro, chloro, bromo and iodo.

"Haloalkyl" refers to an alkyl group wherein the alkyl group is substituted by one or more halo group as described above. The terms "haloalkenyl", "haloalkynyl" and "haloalkoxy" are likewise defined.

"Heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring. The most preferred heteroatom is nitrogen or oxygen.

"Heteroaryl" refers to a monovalent aromatic heterocyclic group which fulfils the Hückel criteria for aromaticity (ie. contains 4n+2π electrons) and preferably has from 2 to 10 carbon atoms and 1 to 4 heteroatoms selected from oxygen, nitrogen, selenium, and sulfur within the ring (and includes oxides of sulfur, selenium and nitrogen). Such heteroaryl groups can have a single ring (eg. pyridyl, pyrrolyl or N-oxides thereof or furyl) or multiple condensed rings (eg. indolizinyl, benzoimidazolyl, coumarinyl, quinolinyl, isoquinolinyl or benzothienyl).

Examples of heterocyclyl and heteroaryl groups include, but are not limited to, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, isothiazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiadiazoles, oxadiazole, oxatriazole, tetrazole, thiazolidine, thiophene, benzo[b]thiophene, morpholino, piperidinyl, pyrrolidine, tetrahydrofuranyl, triazole, and the like.

"Aryl" refers to an unsaturated aromatic carbocyclic group having a single ring (eg. phenyl) or multiple condensed rings (eg. naphthyl or anthryl), preferably having from 6 to 14 carbon atoms. Examples of aryl groups include phenyl, naphthyl and the like.

In this specification "optionally substituted" is taken to mean that a group may or may not be further substituted or fused (so as to form a condensed polycyclic group) with one or more groups selected from hydroxyl, acyl, alkyl, alkoxy, alkenyl, alkenyloxy, alkynyl, alkynyloxy, amino, aminoacyl, thio, arylalkyl, arylalkoxy, aryl, aryloxy, carboxyl, acylamino, cyano, halogen, nitro, phosphono, sulfo, phosphorylamino, phosphinyl, heteroaryl, heteroarylalkyl, heteroaryloxy, heterocyclyl, heterocyclylalkyl, heterocyclyloxy, oxyacyl, oxime, oxime ether, hydrazone, oxyacylamino, oxysulfonylamino, aminoacyloxy, trihalomethyl, trialkylsilyl, pentafluoroethyl, trifluoromethoxy, difluoromethoxy, trifluoromethanethio, trifluoroethenyl, mono- and di-alkylamino, mono- and di-(substituted alkyl)amino, mono- and di-arylamino, mono- and di-heteroarylamino, mono- and di-heterocyclyl amino, and unsymmetric di-substituted amines having different substituents selected from alkyl, aryl, heteroaryl and heterocyclyl, and the like, and may also include a bond to a solid support material, (for example, substituted onto a polymer resin). For instance, an "optionally substituted amino" group may include amino acid and peptide residues.

In some embodiments, Ring A is phenyl and is represented by Formula (II).

In other embodiments, Ring A is pyridinyl and is represented by Formula (III). In an embodiment the compound of formula (III) is a compound of formula (IIIa), (IIIb), or (IIIc):

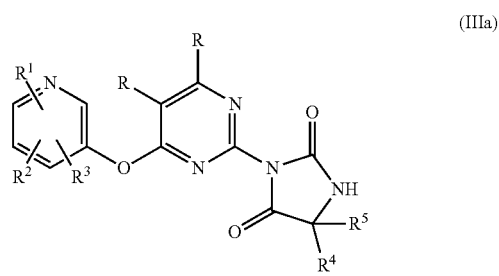

(IIIa)

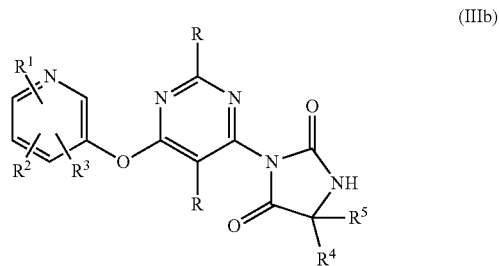

(IIIb)

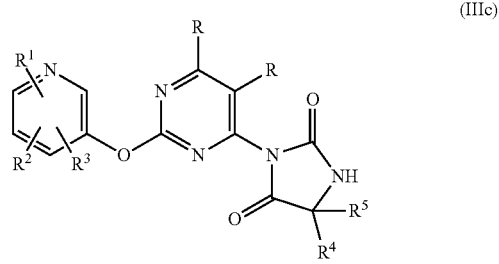

(IIIc)

wherein R and $R^1$ to $R^5$ are as defined above.

In an embodiment, and with reference to formula (IIIa), (IIIb) or (IIIc), both R groups are H.

In an embodiment, and with reference to formula (IIIa), (IIIb) or (IIIc), $R^1$ is $C_1$-$C_5$ alkyl, $R^2$ and $R^3$ are H, and each R is H.

In an embodiment the compound is a compound of formula (IIIb).

In an embodiment the compound is a compound of formula (IIIb) where each R is H.

In an embodiment the compound is a compound of formula (IIIb) where $R^1$ is $C_1$-$C_5$ alkyl and $R^2$ and $R^3$ are H.

In an embodiment the compound is a compound of formula (IIIb) where R is H, and $R^1$ is $C_1$-$C_5$ alkyl and $R^2$ and $R^3$ are H.

In an embodiment the compound of formula (III) is a compound of formula (IIId), (IIIe), or (IIIf):

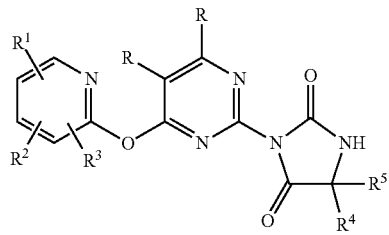
(IIId)

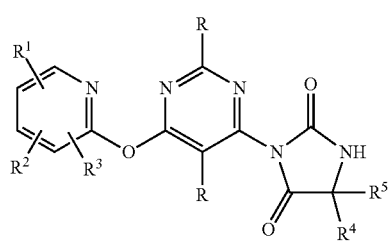
(IIIe)

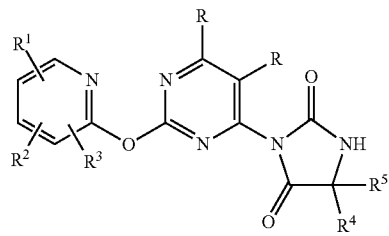
(IIIf)

wherein R and R¹ to R⁵ are as defined above.

In an embodiment the compound of formula (III) is a compound of formula (IIIg), (IIIh), or (IIIi):

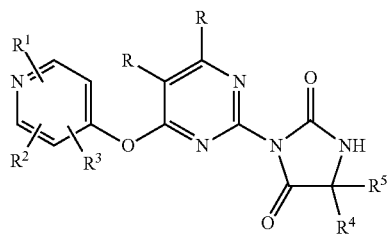
(IIIg)

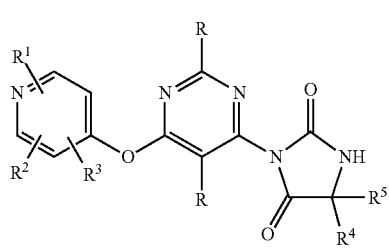
(IIIh)

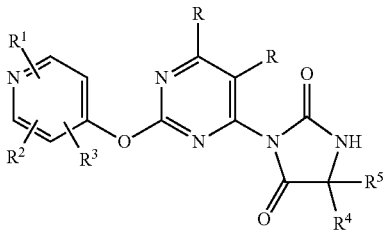
(IIIi)

wherein R and R¹ to R⁵ are as defined above.

In an embodiment the compound of formula (III) is a compound of formula (IIIj), (IIIk), (IIIl), (IIIm), (IIIn), (IIIo), (IIIp), (IIIq) or (IIIr):

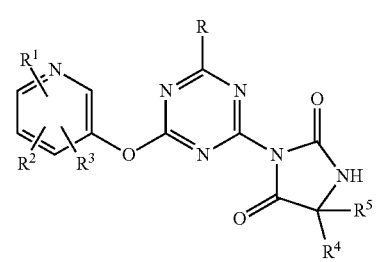
(IIIj)

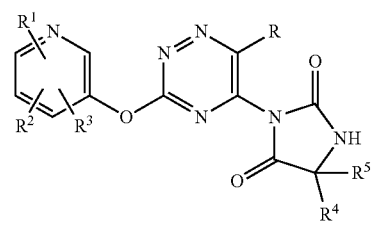
(IIIk)

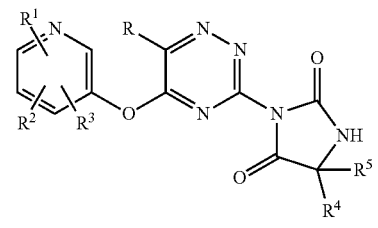
(IIIl)

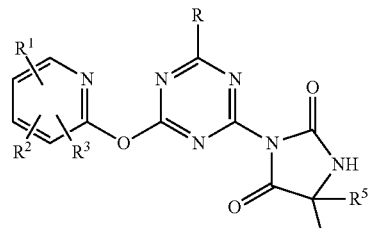
(IIIm)

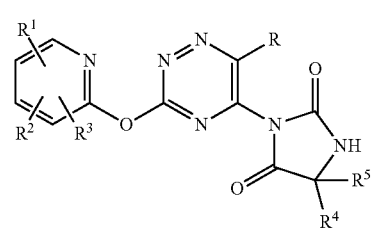
(IIIn)

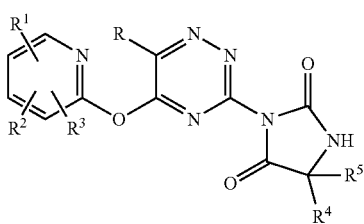
(IIIo)

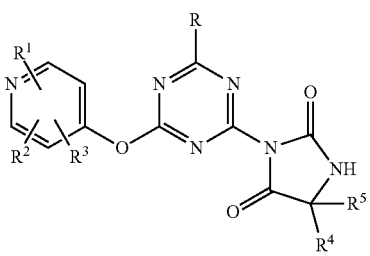
(IIIp)

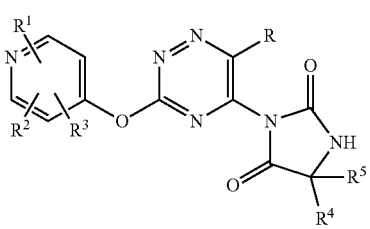
(IIIq)

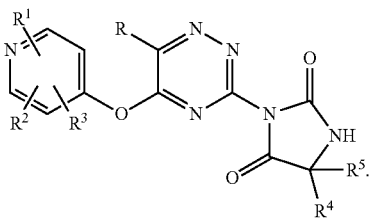
(IIIr)

wherein R and $R^1$ to $R^5$ are as defined above.

$R^2$ and $R^3$ together can represent an optionally substituted 5- or 6-membered O, N or S-containing heterocyclyl. In the context of $R^2$ and $R^3$ being an "optionally substituted" 5-membered O-containing heterocyclyl, the present invention contemplates embodiments where $R^2$ and $R^3$ together are an optionally substituted tetrahydrofuranyl ring. In an embodiment $R^2$ and $R^3$ together are an optionally substituted tetrahydrofuranyl ring wherein the optional substituents are selected from $C_1$-$C_3$ alkyl and $CF_3$. In an embodiment $R^2$ and $R^3$ together represent a moiety of formula (IV):

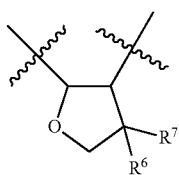
(IV)

wherein $R^6$ and $R^7$ are independently selected from $CH_3$ and $CF_3$.

In an embodiment $R^1$ is $CH_3$.

In an embodiment $R^1$ is $OCH_3$. In other embodiments, $R^1$ is $OCH_2CH_3$. In other embodiments, $R^1$ is cyclopropylmethoxy.

In an embodiment, $R^1$ is F or $CF_3$.

In an embodiment $R^2$ is H or $CH_3$. In another embodiment, $R^2$ is H, F or $CF_3$.

In an embodiment $R^2$ is $OCH_3$. In an embodiment $R^2$ is $OCF_3$.

In an embodiment $R^3$ is H or $CH_3$. In another embodiment, $R^3$ is H, F or $CF_3$.

In an embodiment $R^3$ is $OCH_3$. In an embodiment $R^3$ is $OCF_3$.

In an embodiment $R^2$ and $R^3$ together is an optionally substituted tetrahydrofuranyl ring.

In an embodiment $R^2$ and $R^3$ together is an optionally substituted tetrahydrofuranyl ring of formula (IV) wherein $R^6$ and $R^7$ are independently selected from $CH_3$ and $CF_3$.

In an embodiment $R^4$ is $CH_3$ and $R_5$ is $CH_3$.

In an embodiment $R^4$ is $CH_3$ and $R^5$ is H.

In an embodiment $R^4$ is $CH_2CH_3$ and $R^5$ is H.

In an embodiment $R^4$ is $CH_2CH_3$ and $R^5$ is $CH_3$.

In some embodiments, R is selected from H, halo, $C_1$-$C_3$ haloalkyl, $C_1$-$C_3$ alkoxy or $C_1$-$C_5$ alkyl. In other embodiments, R is selected from H, halo, $C_1$-$C_3$ haloalkyl or $C_1$-$C_5$ alkyl. In other embodiments, R is selected from H, halo or $C_1$-$C_3$ haloalkyl. In other embodiments, R is selected from H, F, Cl, Br or $CF_3$. In other embodiments, R is selected from H, F or $CF_3$.

In certain embodiments, for a compound of formula (I), (II), (III) and subformulae thereof:
$R^1$ represents $OCH_3$ or $CH_3$;
$R^2$ represents $CH_3$ or $OCH_3$;
$R^3$ represents H;
$R^4$ represents $CH_3$ or $CH_2CH_3$; and
$R^5$ is $CH_3$ or H.

In certain embodiments representative

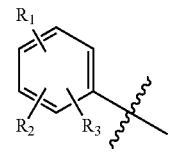

groups include:

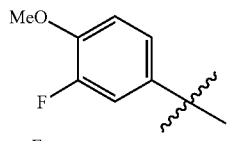 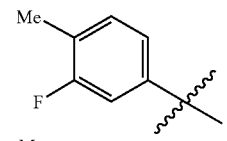

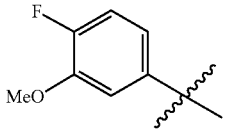 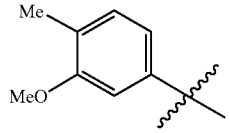

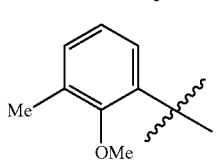 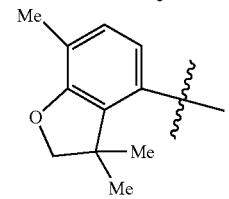

-continued
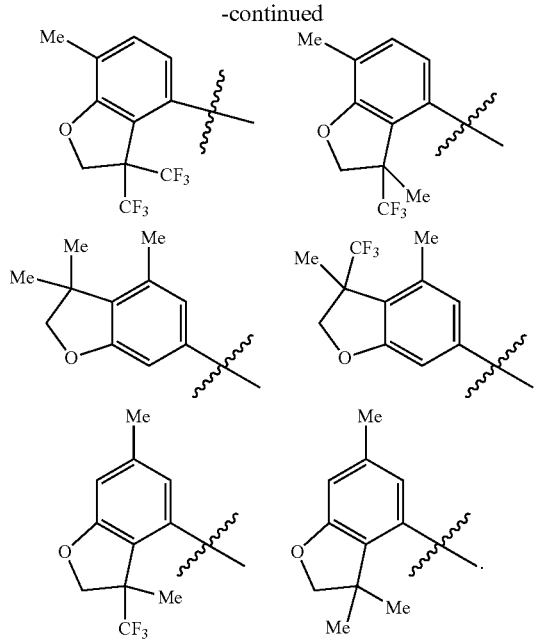
In certain embodiments representative
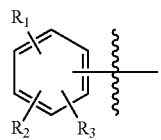
groups include:
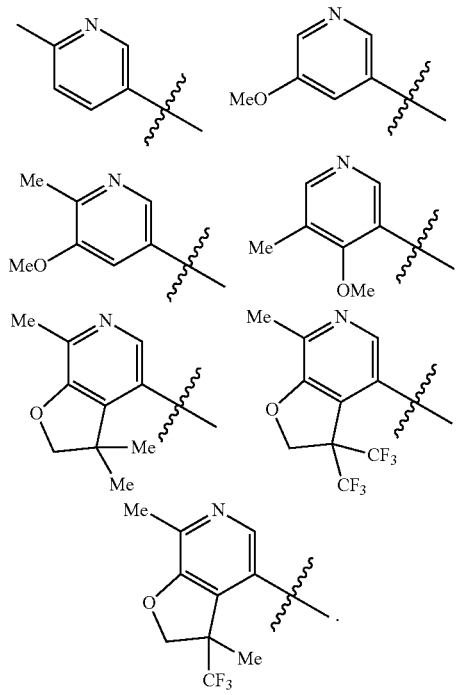
As CR is independently selected, the compound of formula (II) can be a compound of formula (IIa'), (IIa''), (IIa'''), (IIb'), (IIb''), (IIb'''), (IIc'), (IIc'') or (IIc'''):
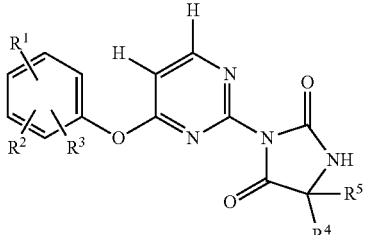
(IIa')
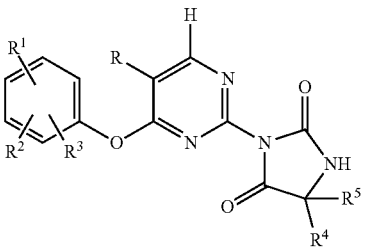
(IIa'')
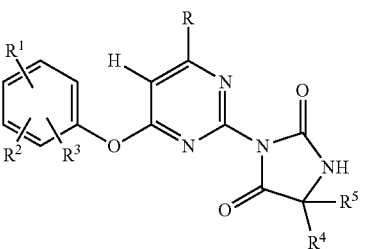
(IIa''')
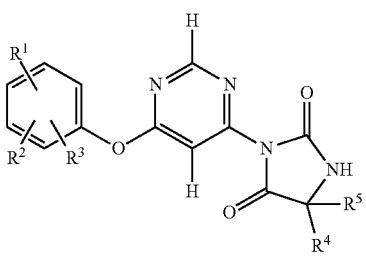
(IIb')
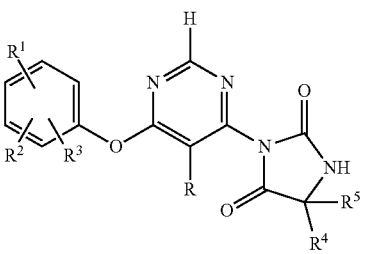
(IIb'')
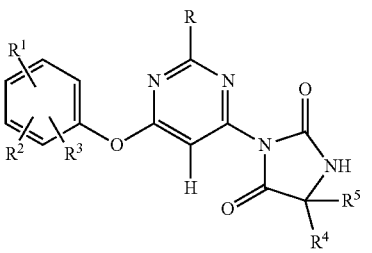
(IIIb''')

-continued

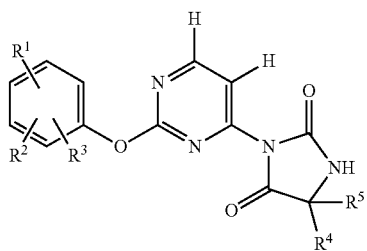
(IIIc')

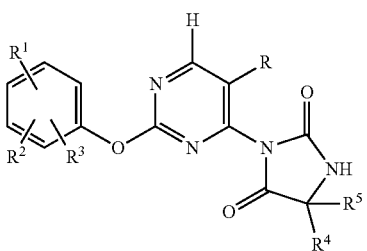
(IIIc'')

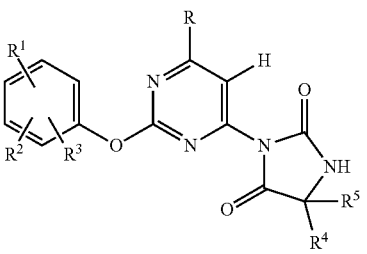
(IIIc''')

wherein R is selected from halo, $C_1$-$C_3$ haloalkyl, $C_1$-$C_3$ alkoxy or $C_1$-$C_5$ alkyl.

In an embodiment the compound of formula (II) is a compound of formula (IId'), (IIe'), or (IIf'):

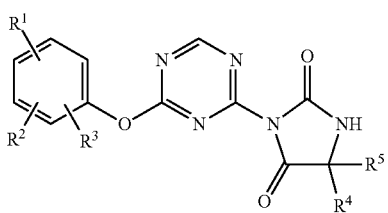
(IId')

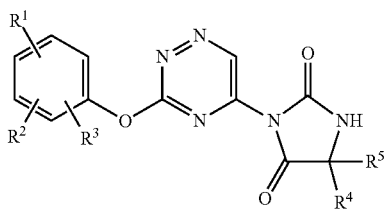
(IIe')

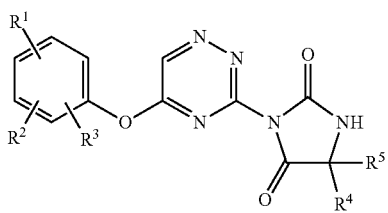
(IIf')

wherein $R^1$ to $R^5$ are as defined above.

Representative compounds of the present invention and compounds which can be used in the methods of the present invention include:

Other representative compounds are:

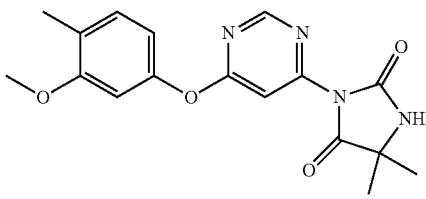

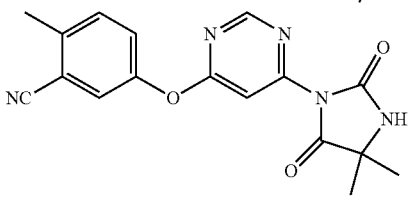

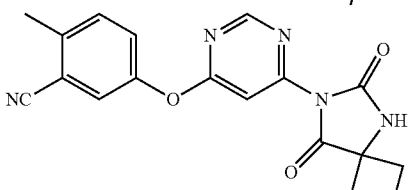

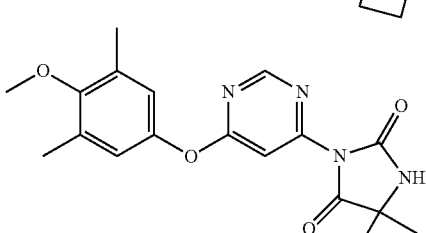

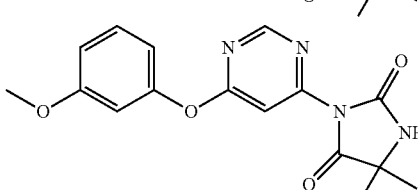

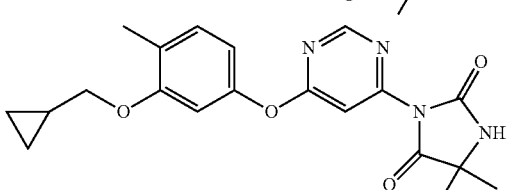

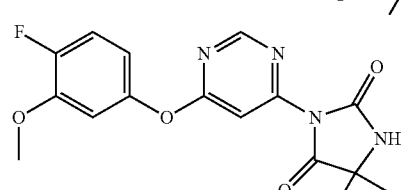

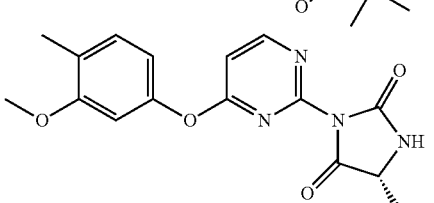

23
-continued
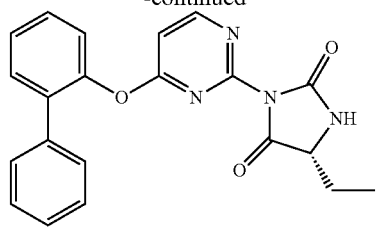
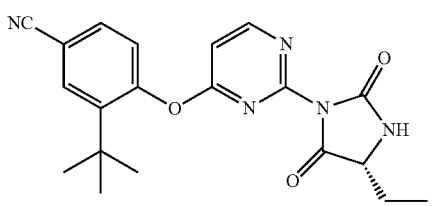
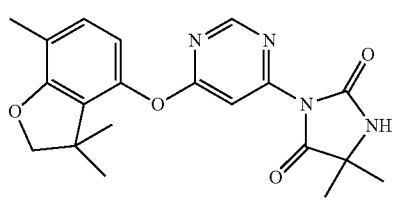
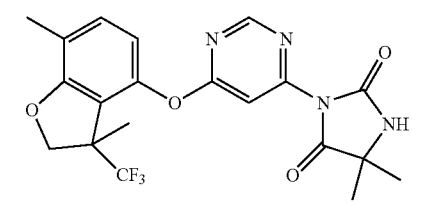
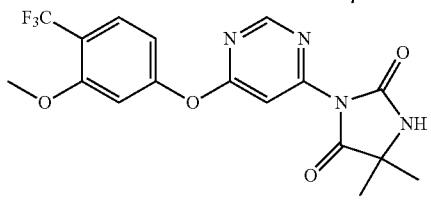
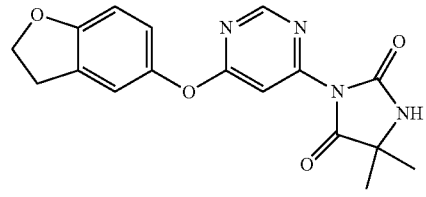
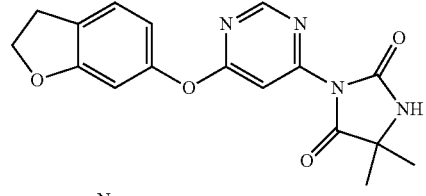
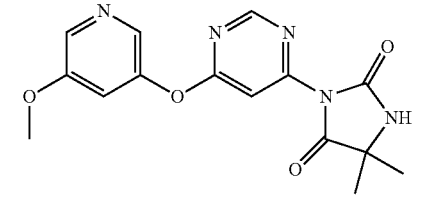
24
-continued
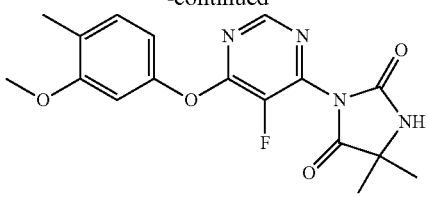
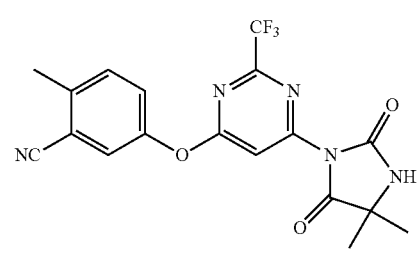
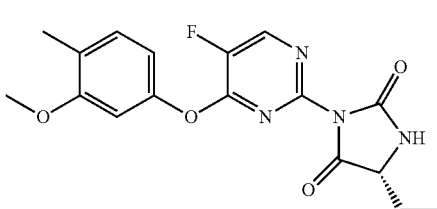
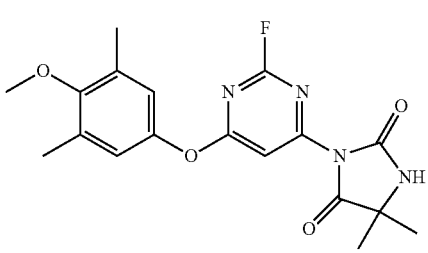
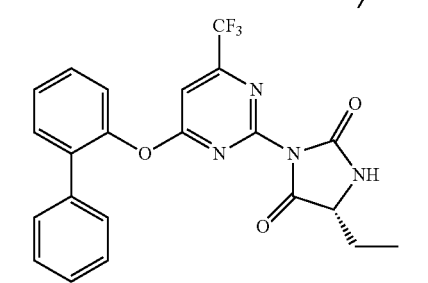
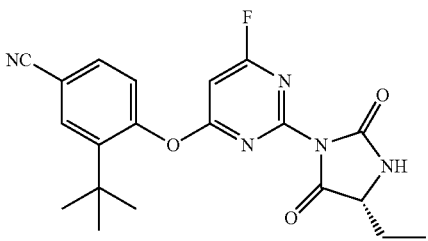
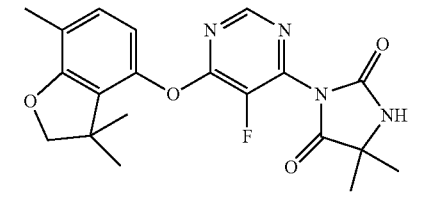

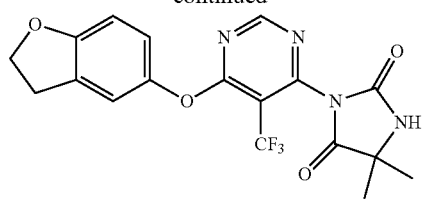
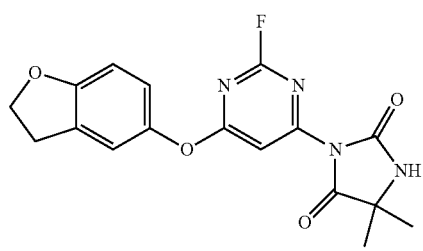
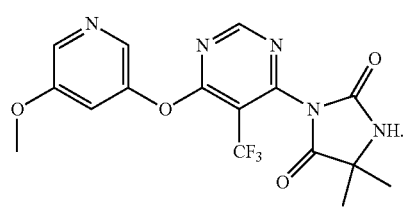
Other representative compounds are:
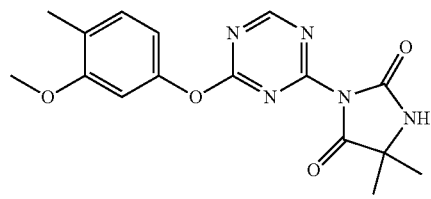
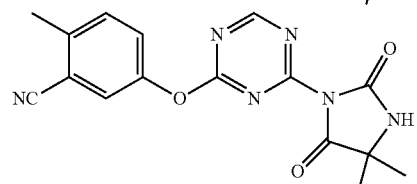
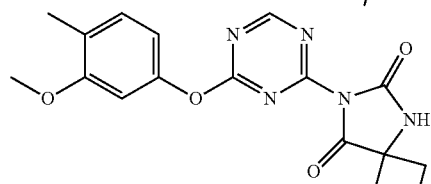
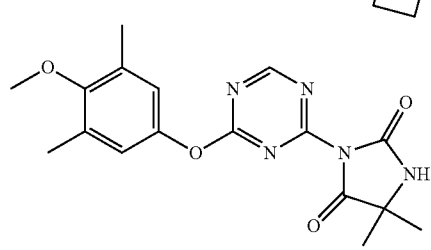
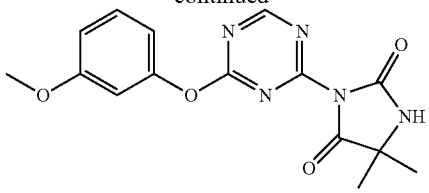
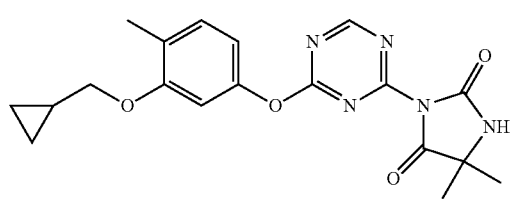
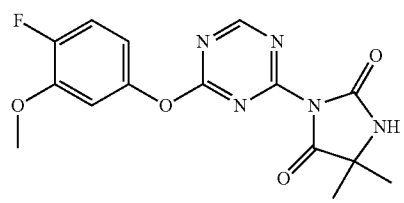
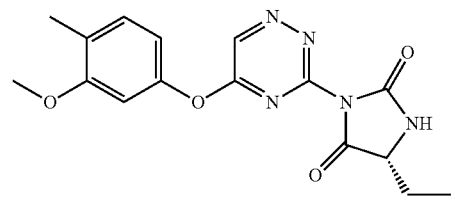
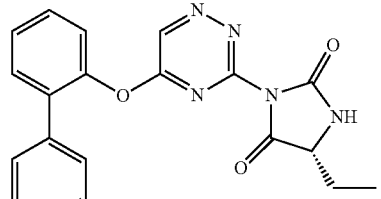
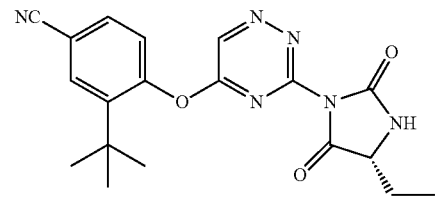
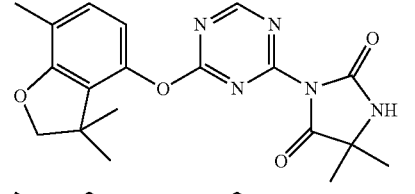
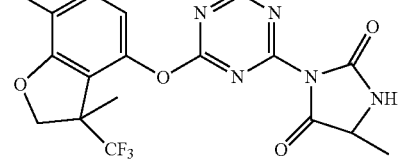

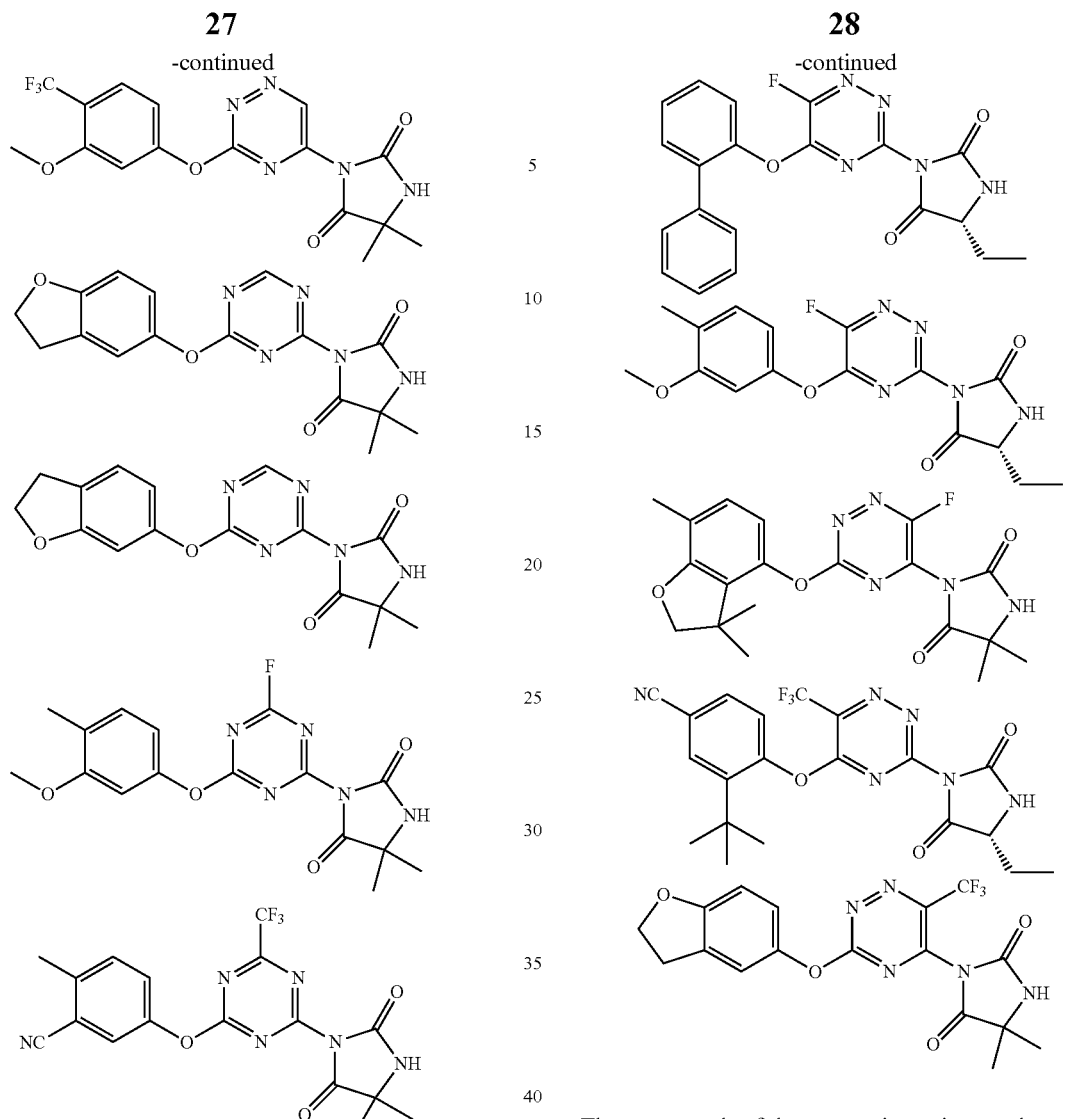
The compounds of the present invention can be prepared according to the General Scheme below:
General Scheme
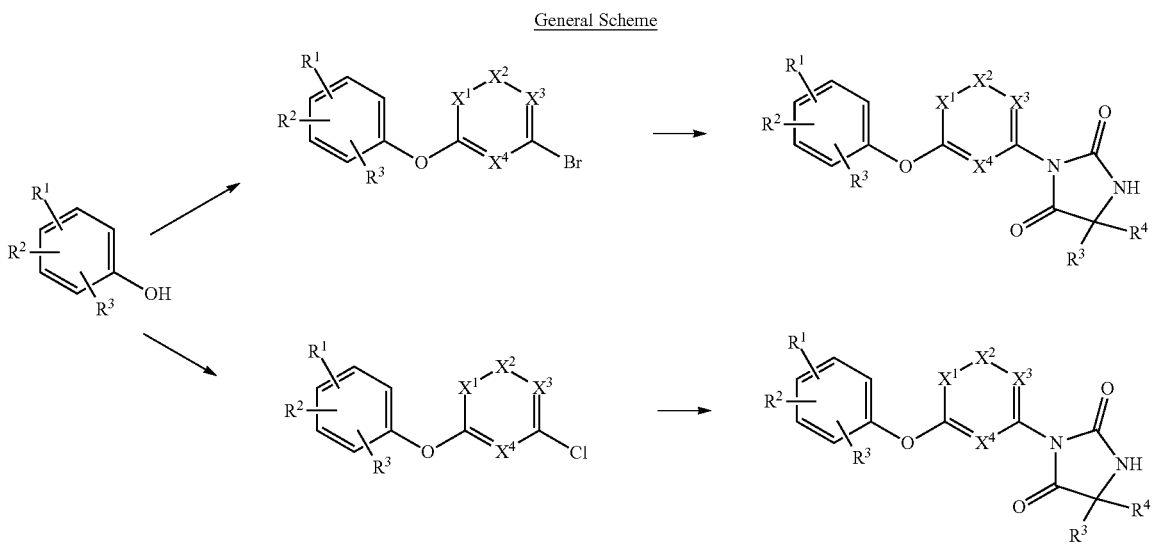

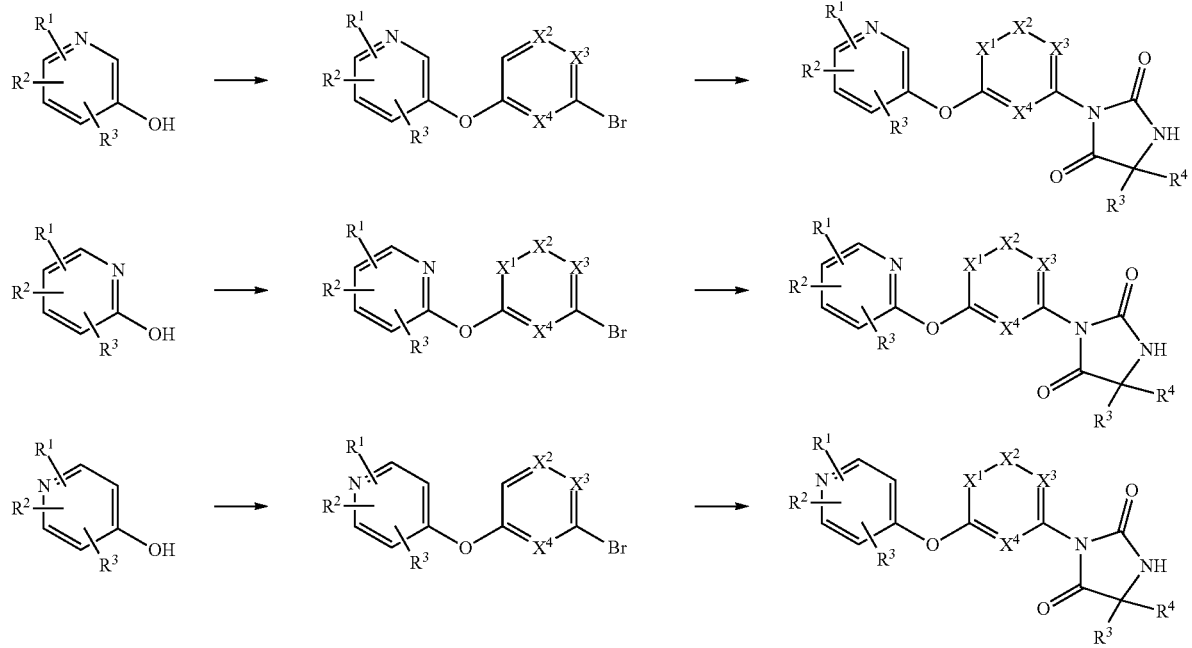

Other compounds of formula (I), (II) and (III) and subformulae thereof can be prepared by the addition, removal or modification of existing substituents. This could be achieved by using standard techniques for functional group interconversion that are well known in the industry, such as those described in "Comprehensive organic transformations: a guide to functional group preparations" by Larock R. C., New York, VCH Publishers, Inc. 1989.

One of ordinary skill in the art will appreciate that the synthetic methods, as described herein, may necessitate a variety of protecting groups. By the term "protecting group", as used herein, it is meant that a particular functional moiety, e.g., O, S, or N, is temporarily blocked so that a reaction can be carried out selectively at another reactive site in a multifunctional compound. Exemplary protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

In studies conducted by the inventors it has been demonstrated that compounds disclosed herein enhance cognition. In certain embodiments, a compound that enhances cognition is a compound that increases by at least 5% (e.g., at least 10%, at least 20%, at least 50%, or more in comparison to a control) in an assay.

Taught herein, therefore, is the use of a compound of formula (I), (II), (III) and their subformulae thereof or an embodiment thereof described herein, or a pharmaceutically acceptable salt thereof, in the manufacture of a medicament for treating or preventing cognitive dysfunction and negative symptoms in a subject in need thereof.

In other embodiments, the present compounds are administered to a subject in need thereof, together with traditional anti-psychotic drugs for a period of about 2-4 weeks, to address the symptoms of schizophrenia, with the option of discontinuing treatment with the present compounds whilst continuing with the traditional therapy. In other embodiments, the subject is treated with both a present compound and one or more traditional medications (administered sequentially or in combination) for the duration of the treatment period.

In some embodiments, a subject according to the methods of the present invention does not suffer from schizophrenia.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of condition, or the amelioration of one or more symptoms (e.g., one or more discernable symptoms) of said condition (i.e., "managing" without "curing" the condition), resulting from the administration of one or more therapies (e.g., one or more therapeutic agents such as a compound or composition of the invention). In specific embodiments, the terms "treat"; "treatment" and "treating" refer to the amelioration of at least one measurable physical parameter of a condition described herein. In other embodiments the terms "treat", "treatment" and "treating" refer to the inhibition of the progression of a condition described herein, either physically by, e.g., stabilization of a discernable symptom or physiologically by, e.g., stabilization of a physical parameter, or both.

The desired therapeutic activity, or effect, will typically depend on the biology underlying the condition being treated, which for these compounds is disruption of cortical gamma oscillations. For example, where a subject with schizophrenia is being treated, the therapeutic effect is a reduction in cognitive impairment and negative symptoms.

The term "preventing" as used herein refers to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure.

The Physician's Desk Reference, a standard text in the field, uses the term "prevent" hundreds of times. As used therein, the terms "prevent", "preventing" and "prevention" with regard to a disorder or disease, refer to averting the cause, effects, symptoms or progression of a disease or disorder prior to the disease or disorder fully manifesting itself.

In certain embodiments, the present compounds of formula (I), (II), (III) and their subformulae thereof or an embodiment thereof described herein, or a pharmaceutically acceptable salt thereof, are administered to said subject sequentially (i.e., before or after) or in combination with an anti-psychotic compound.

In certain embodiments, the present compounds have the further added advantage over traditional therapy in that they exhibit reduced sedative side effects which may adversely affect a patient's quality of life. In certain embodiments, the present compounds are free of measurable sedative side effects.

The compounds enclosed herein are administered to the subject in a treatment effective amount. In some embodiments, a treatment effective amount is a therapeutically effective amount or a prophylactically effective amount. The term "therapeutically effective amount" as used herein means that amount of active compound or pharmaceutical agent that elicits the biological or medicinal response in a tissue, system, animal or human that is being sought by a researcher, veterinarian, medical doctor, or other clinician. The therapeutically effective amount of the compound to be administered will be governed by such considerations, and is the minimum amount necessary to ameliorate, cure, or treat the disease or disorder or one or more of its symptoms. The term "prophylactically effective amount" refers to an amount effective in preventing or substantially lessening the chances of acquiring or in reducing the severity of the cognitive impairment before it is acquired or reducing the severity before the symptoms develop. Roughly, prophylactic measures are divided between primary prophylaxis (to prevent the development of a disease or symptom) and secondary prophylaxis (whereby the disease or symptom has already developed and the patient is protected against worsening of this process).

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, and from about 1 mg/kg to about 25 mg/kg, of subject body weight per day, one or more times a day, to obtain the desired therapeutic effect.

Suitable dosage amounts and dosing regimens can be determined by the attending physician and may depend on the particular condition being treated, the severity of the condition as well as the general age, health and weight of the subject. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The active ingredient may be administered in a single dose or a series of doses. While it is possible for the active ingredient to be administered alone, it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

When "combination therapy" is employed, an effective amount can be achieved using a first amount of a compound of Formula (I), (II), (III) and their subformulae thereof or a pharmaceutically acceptable salt thereof, and a second amount of an additional suitable therapeutic agent.

In certain embodiments, the compound of formula (I), (II), (III) and their subformulae thereof as described herein, or a pharmaceutically acceptable salt thereof, and the additional therapeutic agent are each administered in an effective amount (i.e., each in an amount which would be therapeutically effective if administered alone). In other embodiments, the compound of formula (I), (II), (III) and their subformulae thereof as described herein, or a pharmaceutically acceptable salt thereof, and the additional therapeutic agent are each administered in an amount which alone does not provide a therapeutic effect (a sub-therapeutic dose). In yet other embodiments, the compound of formula (I), (II), (III) and their subformulae thereof as described herein, or a pharmaceutically acceptable salt thereof can be administered in an effective amount, while the additional therapeutic agent is administered in a sub-therapeutic dose. In still other embodiments, the compound of formula (I), (II), (III) and their subformulae thereof as described herein, or a pharmaceutically acceptable salt thereof, can be administered in a sub-therapeutic dose, while the additional therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co-administration also encompasses use of each compound in a sequential manner in either order. When co-administration involves the separate administration of the first amount of a compound of formula (I), (II), (III) and their subformulae thereof as described herein, or a pharmaceutically acceptable salt thereof, and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life, and kinetic profile. For example, a compound of formula (I), (II), (III) and their subformulae thereof as described herein, or a pharmaceutically acceptable salt thereof, and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

Examples of therapeutic agents that may be combined with a compound of this disclosure, either administered separately or in the same pharmaceutical composition, include, but are not limited to, antipsychotics and hypnotics.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

The carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous, and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60], sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., inert diluent, preservative disintegrant (e.g., sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

The active ingredient can be in micro-encapsulated form with one or more excipients. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™ alcohols, oils, modified oils, glycols, polysorbates, cyclodextrins, polymers, and mixtures thereof.

Compositions suitable for topical administration in the mouth include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol, and water. Transdermal patches may also be used to administer the compounds of the invention.

Compositions for rectal administration may be presented as a suppository with a suitable base comprising, for example, cocoa butter, glycerin, gelatine or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described. An injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In certain embodiments, unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The phrase "pharmaceutically acceptable salt," as used herein, refers to pharmaceutically acceptable organic or inorganic salts of a provided compound. For use in medicine, the salts of the provided compounds will be pharmaceutically acceptable salts. Other salts may, however, be useful in the preparation of provided compounds or of their pharmaceutically acceptable salts. Pharmaceutically acceptable salts are well known in the art. For example, Berge et al., describe pharmaceutically acceptable salts in detail in *J. Pharm. Sci.* (1977) 66:1-19, incorporated herein by reference in its entirety. A pharmaceutically acceptable salt involves the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. When multiple charged atoms are present in the parent drug, its pharmaceutically acceptable salts will have multiple counter ions and these can be several instances of the same counter ion or different counter ions. Hence, a pharmaceutically acceptable salt can have one or more charged atoms in the parent compound and/or one or more counter ions.

Pharmaceutically acceptable salts of the compounds described herein include those derived from suitable inorganic and organic acids and bases. In some embodiments, the salts can be prepared in situ during the final isolation and purification of the compounds. In other embodiments the salts can be prepared from the free form of the compound in a separate synthetic step.

When a provided compound is acidic or contains a sufficiently acidic bioisostere, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like. Quarternary ammonium salts such as $N^+(C_{1-4}\text{ alkyl})_4$ are also included.

When a provided compound is basic or contains a sufficiently basic bioisostere, salts may be prepared from pharmaceutically acceptable non-toxic acids, including inorganic and organic acids. Such acids include, but are not limited to, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, carbonic, boric, sulfamic, propionic, butyric, hydroxymaleic, mucic, phenylacetic, sulfanilic, aspartic, edetic, stearic, palmitic, oleic, lauric, ascorbic, valeric, perchloric, malonic, p-toluenesulfonic acid and the like. Particular embodiments include citric, hydrobromic, hydrochloric, maleic, phosphoric, sulfuric and tartaric acids. Other exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, palmoate (i.e., 1,1'-methylene-bis-(2-hydroxy-3-naphthoate)), adipate, alginate, ascorbate, aspartate, cyclopentanepropionate, borate, butyrate, camphorate, digluconate, dodecylsulfate, ethanesulfonate, glucoheptonate, glycerophosphate, hemisulfate, heptanoate, hexanoate, 2-hydroxyethanesulfonate, lactobionate, laurate, lauryl sulphate, malonate, 2-naphthalenesulfonate, nicotinate, pectinate, persulfate, 3-phenylpropionate, picrate, pivalate, propionate, stearate, thiocyanate, undecanoate, and valerate salts.

The preparation of the pharmaceutically acceptable salts described above and other typical pharmaceutically acceptable salts is more fully described by Berge et al., "Pharmaceutical Salts," *J. Pharm. Sci.,* 1977:66:1-19.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

It will be appreciated that any compound that is a prodrug of a compound of formula (I), (II), (III) and their subformulae thereof is also within the scope and spirit of the invention. The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester, such as an acetate or phosphate ester, or where a free amino group is converted into an amide (e.g., α-aminoacid amide). Procedures for esterifying, e.g., acylating, the compounds of the invention are well known in the art and may include treatment of the compound with an appropriate carboxylic acid, anhydride or chloride in the presence of a suitable catalyst or base.

The compounds of the invention may be in crystalline form either as the free compounds or as solvates (e.g., hydrates) and it is intended that both forms are within the scope of the present invention. Methods of solvation are generally known within the art.

It will also be recognised that compounds of the invention may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be prepared by asymmetric synthesis, for example using chiral intermediates, or mixtures may be resolved by conventional methods, e.g., chromatography, or use of a resolving agent.

Furthermore, depending on the substitution pattern the compounds of the present invention may be capable of undergoing tautomerism. Accordingly, all possible tautomers of a compound of the present invention fall within the scope and spirit of the invention.

The synthetic methods and processes described herein to prepare the compounds of the present invention are amenable to solid phase synthetic techniques and/or combinatorial chemistry to produce individual compounds or libraries of compounds.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Certain embodiments of the invention will now be described with reference to the following examples which are intended for the purpose of illustration only and are not intended to limit the scope of the generality hereinbefore described.

EXAMPLES

Abbreviations

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), methoxy (MeO), ethoxy (EtO), trimethylsilyl (TMS), tert-butyloxycarbonyl (Boc), and acetyl (Ac).

For convenience, many chemical compounds are represented using well known abbreviations, including but not limited to, methanol (MeOH), ethanol (EtOH), ether or diethyl ether ($Et_2O$), ethyl acetate (EtOAc), triethylamine (TEA, $Et_3N$), N,N-diisopropyl-N-ethylamine (DIEA), dichloromethane (methylene chloride, DCM), trifluoroacetic acid (TFA), trifluoroethanol (TFE), dimethylformamide (DMF), sodium sulphate ($Na_2SO_4$), tetrahydrofuran (THF), meta-chloroperbenzoic acid (mCPBA), hexamethyldisilazane sodium salt (NaHMDS), O-(7-azabenzotriazol-1-yl)-N,N,N',N'-tetramethyluronium hexafluorophosphate (HATU), dimethylsulfoxide (DMSO), magnesium sulphate ($MgSO_4$), sodium hydrogen carbonate ($NaHCO_3$), tert-butanol (t-BuOH), 1-ethyl-3-(3-dimethylaminopropyl) carbodiimide hydrochloride salt (EDCl·HCl), tetra-n-butylammonium fluoride (TBAF), N,N-diisopropylethylamine (DIPEA), 1-hydroxybenzotriazole (HOBt), hexafluorophosphate benzotriazole teramethyl uronium (HBTU), trans-dichlorobis(triphenylphosphine)palladium(II) ($PdCl_2(PPh_3)_2$), tetrakis(triphenylphosphine)palladium(0) ($Pd(PPh_3)_4$) tris(dibenzylideneacetone) dipalladium(0) ($Pd_2(dba)_3$), tri-t-butyl phosphonium tetrafluoroborate (t-$Bu_3PH·BF_4$), 4,5-bis (diphenylphosphino)-9,9-dimethylxanthene (Xantphos), triphenylphosphine ($PPh_3$), tert-butoxycarbonyl (Boc), diisopropyl azodicarboxylate (DIAD), pyridinium chlorochromate (PCC), borane dimethylsulfide (BMS), titanium isopropoxide ($TiOiPr_4$), sodium triacetoxyborohydride ($NaBH(OAc)_3$), sodium cyanoborohydride ($NaBH_3(CN)$), ammonium chloride ($NH_4Cl$), chloroform ($CHCl_3$), manganese dioxide ($MnO_2$), potassium carbonate ($K_2CO_3$) and 1,2-dichloroethane (DCE), sodium hydride (NaH), dimethylacetamide (DMA), copper(I) oxide ($Cu_2O$), N-methyl-2-pyrrolidone (NMP), cesium carbonate ($Cs_2CO_3$), hydrochloric acid (HC), 2-aminobutyric acid (Abu).

General Experimental

Analytical thin-layer chromatography (TLC) was performed on Merck silica gel 60F254 aluminium-backed plates which were visualized using fluorescence quenching under UV light. Flash chromatography was performed using a Biotage Isolera One and standard cartridges. Size exclusion chromatography was performed using Sephadex LH-20, eluted with a dichloromethane/methanol solution (ratio 75/25). Semi-preparative HPLC purification was performed using a Gilson PLC2020 and a Princeton SPHER-60, C8, 10 µm, 30×150 mm as column.

Intermediate 1-1: 3-methoxy-4-methyl-phenol

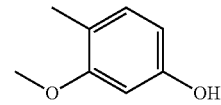

To a solution of 4-hydroxy-2-methoxy-benzaldehyde (1.8 g, 11.8 mmol) in ethanol/acetic acid (50 mL/7.5 mL) was added 10% palladium on activated carbon (500 mg). The mixture was evacuated and back-filled with $H_2$ (×3) and was left under 4 bars of $H_2$, stirring at rt for 18 h. The reaction mixture was filtered through Celite, rinsing with EtOAc before conc. in vacuo. The crude product thus obtained was purified by flash chromatography on silica with a gradient of ethyl acetate:cyclohexane—0:100 to 30:70 to give the title compound as a colorless gum (1.4 g, 85%). $^1$H NMR (300 MHz, DMSO-$d_6$) 9.14 (s, 1H), 6.86 (d, J=8.0 Hz, 1H), 6.33 (d, J=2.2 Hz, 1H), 6.22 (dd, J=2.2 and 8.0 Hz, 1H), 3.70 (s, 3H), 2.00 (s, 3H).

Intermediate 1-2: 4-bromo-6-(3-methoxy-4-methyl-phenoxy)pyrimidine

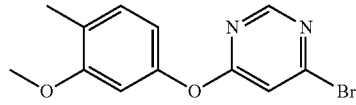 [SMILES: COc1cc(Oc2cc(Br)ncn2)ccc1C]

To a stirred solution of 4,6-dibromopyrimidine (500 mg, 2.1 mmol) and 3-methoxy-4-methyl-phenol (290 mg, 2.1 mmol) in THF (4 mL) at 25° C. was added cesium carbonate (1.37 g, 4.2 mmol). After addition, the mixture was stirred at 25° C. for 4 h. The resulting mixture was diluted with water (10 mL) and extracted with ethyl acetate (3×10 mL). The combined organic extracts were washed with saturated aqueous sodium chloride (10 mL), dried over magnesium sulfate, filtered, and concentrated under reduced pressure to give the title compound as a yellow oil and pure enough to be used as such (600 mg, 97% yield). $^1$H NMR (300 MHz, CHCl₃-d) 8.55 (d, J=0.7 Hz, 1H), 7.19 (d, J=8.0 Hz, 1H), 7.06 (s, 1H), 6.65-6.58 (m, 2H), 3.80 (s, 3H), 2.21 (s, 3H).

Example 1: 3-[6-(3-methoxy-4-methyl-phenoxy)pyrimidin-4-yl]-5,5-dimethyl-imidazolidine-2,4-dione

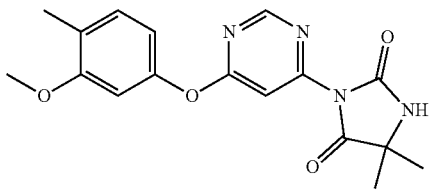

In a sealable vessel, to a stirred solution of 4-bromo-6-(3-methoxy-4-methyl-phenoxy)pyrimidine (400 mg, 1.36 mmol) and 5,5-dimethylimidazolidine-2,4-dione (174 mg, 1.36 mmol) in DMF (8 mL), was added dipotassium carbonate (375 mg, 2.71 mmol) and trans-N,N'-Dimethylcyclohexane-1,2-diamine (39 mg, 0.27 mmol). The reaction was flushed with argon for 10 minutes and then copper iodide (52 mg, 0.27 mmol) was added. The vessel was sealed and stirred at 110° C. for 18 h. The resulting mixture was diluted with water (25 mL) and extracted with ethyl acetate (2×25 mL). The combined organic extracts were concentrated under reduced pressure. The crude product thus obtained was purified sequentially by two flash chromatography on silica with a gradient of ethyl acetate:cyclohexane—0:100 to 100:0 to give after concentration under reduced pressure, trituration in diethyl ether (5 mL) and filtration the title compound as a white solid (72 mg, 15% yield). ¹H NMR (300 MHz, DMSO-d₆) 8.77 (d, J=0.8 Hz, 1H), 8.73 (s, 1H), 7.20 (d, J=8.2 Hz, 1H), 7.12 (d, J=0.8 Hz, 1H), 6.86 (d, J=2.2 Hz, 1H), 6.71 (dd, J=8.0 and 2.2 Hz, 1H), 3.74 (s, 3H), 2.14 (s, 3H), 1.38 (s, 6H). ESIMS m/z [M+H]⁺=343.3.

Intermediate 1-3: (5R)-5-ethyl-5-methyl-imidazolidine-2,4-dione

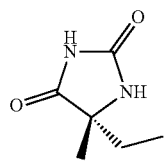

To a suspension of (2R)-2-amino-2-methyl-butanoic acid (1000 mg, 8.5 mmol) in water (30 mL) was added potassium cyanate (900 mg, 11.1 mmol) and the mixture was stirred at 90° C. for 3 h. After the solution was cooled to rt, hydrochloric acid 37% (18 mL) was added carefully and heating continued at 90° C. for 2 h. The solvent was removed in presence of EtOH and toluene under reduced pressure, the white solid was taken in 5:1 DCM/EtOH (12 mL) and filtered. The filtrate was evaporated under reduced pressure to give (5R)-5-ethyl-5-methyl-imidazolidine-2,4-dione (1110 mg, 91% yield) as a white solid and pure enough to be used as such for next step. ¹H NMR (300 MHz, DMSO-d₆) 10.55 (s, 1H), 7.87 (s, 1H), 1.63-1.43 (m, 2H), 1.20 (s, 3H), 0.74 (t, J=8.4 Hz, 3H).

Example 2: (5R)-5-ethyl-3-[6-(3-methoxy-4-methyl-phenoxy)pyrimidin-4-yl]-5-methyl-imidazolidine-2,4-dione

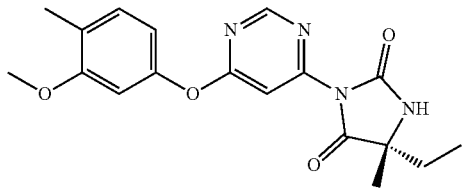 [SMILES: CC[C@@]1(C)NC(=O)N(c2cc(Oc3ccc(C)c(OC)c3)ncn2)C1=O]

Essentially following the procedures described for example 1-1, using (5R)-5-ethyl-5-methyl-imidazolidine-2,4-dione (115 mg, 0.81 mmol) to afford, after two purifications by silica gel chromatography eluting with a gradient of ethyl acetate:cyclohexane—0:100 to 100:0 and a lyophilization using acetonitrile and water, the title compound as a white solid (107 mg, 36% yield). ¹H NMR (300 MHz, DMSO-d₆) 8.76 (d, J=0.8 Hz, 1H), 8.69 (s, 1H), 7.19 (d, J=8.2 Hz, 1H), 7.11 (d, J=0.8 Hz, 1H), 6.86 (d, J=2.2 Hz, 1H), 6.71 (dd, J=8.0 and 2.2 Hz, 1H), 3.74 (s, 3H), 2.14 (s, 3H), 1.80-1.58 (m, 2H), 1.36 (s, 3H), 0.84 (t, J=7.4 Hz, 3H). ESIMS m/z [M+H]⁺=357.4.

Intermediate 1-4: (5S)-5-ethyl-5-methyl-imidazolidine-2,4-dione

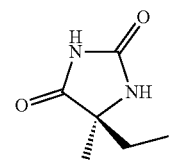

Essentially following the procedures described for intermediate 1-3, using (2S)-2-amino-2-methyl-butanoic acid hydrochloride (1000 mg, 6.5 mmol) to give (5S)-5-ethyl-5-methyl-imidazolidine-2,4-dione (950 mg, 91% yield) as a white solid and pure enough to be used as such for next step. ¹H NMR (300 MHz, DMSO-d₆) 10.55 (s, 1H), 7.87 (s, 1H), 1.63-1.43 (m, 2H), 1.20 (s, 3H), 0.74 (t, J=8.4 Hz, 3H).

Example 3: (5S)-5-ethyl-3-[6-(3-methoxy-4-methyl-phenoxy)pyrimidin-4-yl]-5-methyl-imidazolidine-2,4-dione

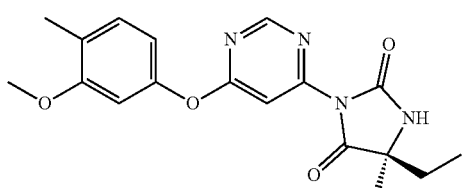

Essentially following the procedures described for example 1-1, using (5S)-5-ethyl-5-methyl-imidazolidine-2,4-dione (146 mg, 1.02 mmol) to afford, after purification by silica gel chromatography eluting with a gradient of ethyl acetate:cyclohexane—0:100 to 100:0 and a lyophilization using acetonitrile and water, the title compound as a white solid (73 mg, 19% yield). $^1$H NMR (300 MHz, DMSO-$d_6$) 8.76 (d, J=0.8 Hz, 1H), 8.69 (s, 1H), 7.19 (d, J=8.2 Hz, 1H), 7.11 (d, J=0.8 Hz, 1H), 6.86 (d, J=2.2 Hz, 1H), 6.71 (dd, J=8.0 and 2.2 Hz, 1H), 3.74 (s, 3H), 2.14 (s, 3H), 1.80-1.58 (m, 2H), 1.36 (s, 3H), 0.83 (t, J=7.4 Hz, 3H). ESIMS m/z [M+H]$^+$=357.4.

Intermediate 1-5: 5,5-diethylimidazolidine-2,4-dione

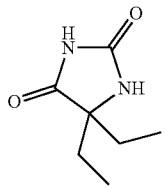

Essentially following the procedures described for intermediate 1-3, using 2-amino-2-ethyl-butanoic acid (500 mg, 3.8 mmol) to give 5,5-diethylimidazolidine-2,4-dione (620 mg, 83% yield) as a yellow oil and pure enough to be used as such for next step. $^1$H NMR (300 MHz, CHCl$_3$-d) 8.44 (s, 1H), 5.88 (s, 1H), 1.92-1.75 (m, 2H), 1.75-1.58 (m, 2H), 0.92 (t, J=7.4 Hz, 6H).

Example 4: 3-[6-(3-methoxy-4-methyl-phenoxy)pyrimidin-4-yl]-5,5-diethyl-imidazolidine-2,4-dione

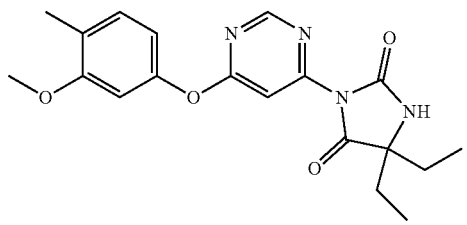 [SMILES: CCC1(CC)NC(=O)N(c2cc(Oc3ccc(C)c(OC)c3)ncn2)C1=O]

Essentially following the procedures described for example 1-1, using 5,5-diethylimidazolidine-2,4-dione (190 mg, 1.20 mmol) to afford, after two purifications by silica gel chromatography eluting with a gradient of ethyl acetate:cyclohexane—0:100 to 100:0 and a lyophilization using acetonitrile and water, the title compound as a white solid (80 mg, 17% yield). $^1$H NMR (300 MHz, DMSO-$d_6$) 8.76 (s, 1H), 8.64 (s, 1H), 7.19 (d, J=8.1 Hz, 1H), 7.11 (s, 1H), 6.86 (d, J=2.2 Hz, 1H), 6.71 (dd, J=8.0 and 2.2 Hz, 1H), 3.74 (s, 3H), 2.14 (s, 3H), 1.80-1.58 (m, 4H), 0.84 (t, J=7.4 Hz, 3H). ESIMS m/z [M+H]$^+$=371.4.

Intermediate 1-6: 5,7-diazaspiro[3.4]octane-6,8-dione

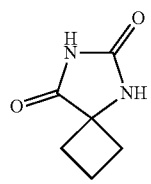

Essentially following the procedures described for intermediate 1-3, using 1-Amino-1-cyclobutanecarboxylic acid (500 mg, 4.3 mmol) to give 5,7-diazaspiro[3.4]octane-6,8-dione (405 mg, 63% yield) as a white solid and pure enough to be used as such for next step. $^1$H NMR (300 MHz, DMSO-$d_6$) 10.50 (s, 1H), 8.29 (s, 1H), 2.37-2.15 (m, 4H), 1.90-1.71 (m, 2H).

Example 5: 7-[6-(3-methoxy-4-methyl-phenoxy)pyrimidin-4-yl]-5,7-diazaspiro[3.4]octane-6,8-dione

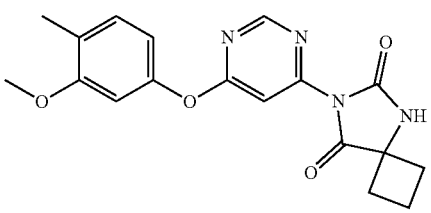 [SMILES: COc1cc(Oc2cc(N3C(=O)NC4(CCC4)C3=O)ncn2)ccc1C]

Essentially following the procedures described for example 1-1, using 5,7-diazaspiro[3.4]octane-6,8-dione (140 mg, 1.0 mmol) to afford, after purification by silica gel chromatography eluting with a gradient of ethyl acetate:cyclohexane—0:100 to 100:0, a semi-preparative purification and a lyophilization using acetonitrile and water, the title compound as a white foam (35 mg, 9% yield). $^1$H NMR (300 MHz, CHCl$_3$-d) 8.83 (s, 1H), 7.17 (d, J=8.0 Hz, 1H), 7.06 (s, 1H), 6.70-6.62 (m, 2H), 6.00 (bs, 1H), 3.81 (s, 3H), 2.80-2.70 (m, 2H), 2.50-2.38 (m, 2H), 2.20 (s, 3H), 2.30-2.15 (m, 1H), 2.00-1.87 (m, 1H). ESIMS m/z [M+H]$^+$=355.4.

Example 6: 3-[6-(3-methoxy-4-methyl-phenoxy)pyrimidin-4-yl]-1,3-diazaspiro[4.4]nonane-2,4-dione

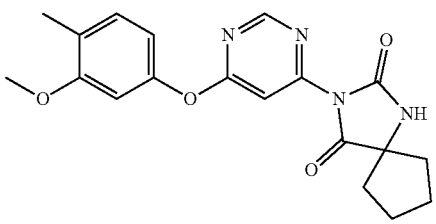 [SMILES: COc1cc(Oc2cc(N3C(=O)NC4(CCCC4)C3=O)ncn2)ccc1C]

Essentially following the procedures described for example 1-1, using 1,3-diazaspiro[4.4]nonane-2,4-dione (105 mg, 0.68 mmol) to afford, after purification by silica gel chromatography eluting with a gradient of ethyl acetate:cyclohexane—0:100 to 100:0, a semi-preparative purification and a lyophilization using methanol and water, the title compound as a white foam (30 mg, 12% yield). $^1$H NMR (300 MHz, DMSO-$d_6$) 8.93 (bs, 1H), 8.76 (d, J=0.9 Hz, 1H), 7.19 (d, J=8.6 Hz, 1H), 7.11 (d, J=0.9 Hz, 1H), 6.86 (d, J=2.2 Hz, 1H), 6.70 (dd, J=2.2 and 8.0 Hz, 1H), 3.75 (s, 3H), 2.14 (s, 3H), 2.10-1.97 (m, 2H), 1.90-1.68 (m, 6H). ESIMS m/z [M+H]$^+$=369.4.

Example 7: 7-[6-(3-methoxy-4-methyl-phenoxy)pyrimidin-4-yl]-1,3-diazaspiro[4.5]decane-2,4-dione

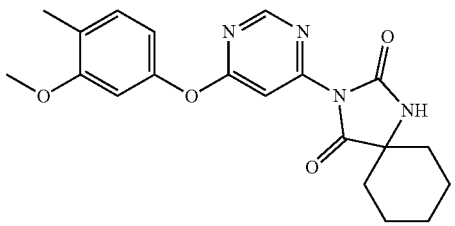 [SMILES: COc1cc(Oc2cc(N3C(=O)NC4(CCCCC4)C3=O)ncn2)ccc1C]

Essentially following the procedures described for example 1-1, using 1,3-diazaspiro[4.5]decane-2,4-dione (103 mg, 0.61 mmol) to afford, after purification by silica gel chromatography eluting with a gradient of ethyl acetate:cyclohexane—0:100 to 100:0 and a lyophilization using methanol and water, the title compound as a white foam (19 mg, 9% yield). $^1$H NMR (300 MHz, DMSO-d$_6$) 9.12 (bs, 1H), 8.76 (d, J=0.8 Hz, 1H), 7.19 (d, J=8.6 Hz, 1H), 7.11 (d, J=0.8 Hz, 1H), 6.86 (d, J=2.2 Hz, 1H), 6.70 (dd, J=2.2 and 8.0 Hz, 1H), 3.75 (s, 3H), 2.14 (s, 3H), 1.78-1.49 (m, 9H), 1.46-1.25 (m, 1H). ESIMS m/z [M+H]$^+$=383.4.

Intermediate 1-7:
(5R)-5-isopropyl-5-methyl-imidazolidine-2,4-dione

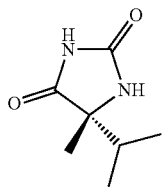

Essentially following the procedures described for intermediate 1-3, using (2R)-2-amino-2,3-dimethyl-butanoic acid (500 mg, 3.8 mmol) to give (5R)-5-isopropyl-5-methyl-imidazolidine-2,4-dione (345 mg, 58% yield) as a white solid and pure enough to be used as such for next step. $^1$H NMR (300 MHz, DMSO-d$_6$) 10.52 (bs, 1H), 7.89 (bs, 1H), 1.79 (sept, J=6.8 Hz, 1H), 1.19 (s, 3H), 0.85 (d, J=6.8 Hz, 3H), 0.74 (d, J=6.8 Hz, 3H).

Example 8: (5R)-5-isopropyl-3-[6-(3-methoxy-4-methyl-phenoxy)pyrimidin-4-yl]-5-methyl-imidazolidine-2,4-dione

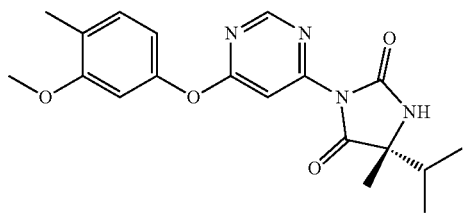 [SMILES: COc1cc(Oc2cc(N3C(=O)N[C@](C)(C(C)C)C3=O)ncn2)ccc1C]

Essentially following the procedures described for example 1-1, using (5R)-5-isopropyl-5-methyl-imidazolidine-2,4-dione (103 mg, 0.66 mmol) to afford, after purification by silica gel chromatography eluting with a gradient of ethyl acetate:cyclohexane—0:100 to 100:0 and a Sephadex exclusion chromatography, the title compound as a white foam (127 mg, 65% yield). $^1$H NMR (300 MHz, DMSO-d$_6$) 8.76 (d, J=0.8 Hz, 1H), 8.72 (bs, 1H), 7.19 (d, J=8.5 Hz, 1H), 7.11 (d, J=0.8 Hz, 1H), 6.86 (d, J=2.2 Hz, 1H), 6.70 (dd, J=2.2 and 8.0 Hz, 1H), 3.74 (s, 3H), 2.13 (s, 3H), 1.94 (sept, J=6.8 Hz, 1H), 1.36 (s, 3H), 0.93 (d, J=6.8 Hz, 3H), 0.84 (d, J=6.8 Hz, 3H). ESIMS m/z [M+H]$^+$=371.3.

Intermediate 1-8:
4-bromo-6-(2-methoxy-phenoxy)pyrimidine

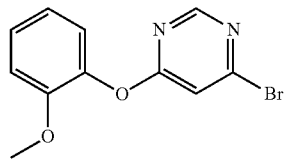 [SMILES: COc1ccccc1Oc1cc(Br)ncn1]

Essentially following the procedures described for intermediate 1-2, using 2-methoxyphenol (156 mg, 1.26 mmol) to afford, after purification by silica gel chromatography eluting with a gradient of ethyl acetate:cyclohexane—0:100 to 30:70, the title compound as a yellow oil (320 mg, 90% yield). $^1$H NMR (300 MHz, CHCl$_3$-d) 8.51 (d, J=0.7 Hz, 1H), 7.32-7.25 (m, 1H), 7.15-7.10 (m, 2H), 7.05-6.98 (m, 2H), 6.92-6.85 (m, 2H), 3.77 (s, 3H). ESIMS m/z [M+H]$^+$=281.4.

Example 9: 3-[6-(2-methoxyphenoxy)pyrimidin-4-yl]-5,5-dimethyl-imidazolidine-2,4-dione

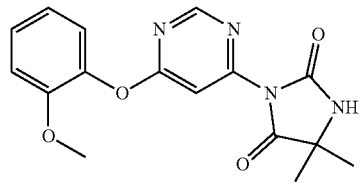 [SMILES: COc1ccccc1Oc1cc(N2C(=O)NC(C)(C)C2=O)ncn1]

Essentially following the procedures described for example 1-1, using 4-bromo-6-(2-methoxy-phenoxy)pyrimidine (320 mg, 1.14 mmol) to afford, after purification by silica gel chromatography eluting with a gradient of ethyl acetate:cyclohexane—0:100 to 100:0, a semi-preparative purification and a lyophilization using acetonitrile and water, the title compound as a white foam (93 mg, 25% yield). $^1$H NMR (300 MHz, DMSO-d$_6$) 8.75 (s, 1H), 8.71 (d, J=0.8 Hz, 1H), 7.31-7.19 (m, 3H), 7.16 (d, J=0.8 Hz, 1H), 7.00 (td, J=7.8 and 1.2 Hz, 1H), 3.70 (s, 3H), 1.38 (s, 6H). ESIMS m/z [M+H]$^+$=329.3.

Intermediate 1-9:
4-bromo-6-(3-methoxy-phenoxy)pyrimidine

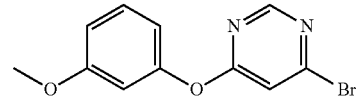 [SMILES: COc1cccc(Oc2cc(Br)ncn2)c1]

Essentially following the procedures described for intermediate 1-2, using 3-methoxyphenol (260 mg, 2.1 mmol) to afford, after purification by silica gel chromatography, eluting with a gradient of ethyl acetate:cyclohexane—0:100 to 30:70, the title compound as a yellow oil (550 mg, 93% yield). ¹H NMR (300 MHz, DMSO-d₆) 8.58 (d, J=0.7 Hz, 1H), 7.48 (d, J=0.7 Hz, 1H), 7.35 (t, J=8.0 Hz, 1H), 6.89-6.75 (m, 3H), 3.74 (s, 3H).

Example 10: 3-[6-(3-methoxyphenoxy)pyrimidin-4-yl]-5,5-dimethyl-imidazolidine-2,4-dione

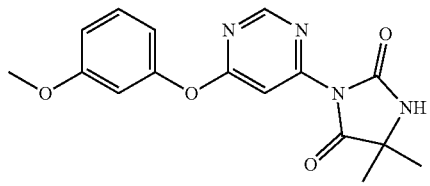

Essentially following the procedures described for example 1-1, using 4-bromo-6-(3-methoxy-phenoxy)pyrimidine (550 mg, 1.95 mmol) to afford, after two purifications by silica gel chromatography eluting with a gradient of ethyl acetate:cyclohexane—0:100 to 100:0, a semi-preparative purification and a lyophilization using acetonitrile and water, the title compound as a white solid (155 mg, 24% yield). ¹H NMR (300 MHz, DMSO-d₆) 8.77 (d, J=0.8 Hz, 1H), 8.75 (s, 1H), 7.36 (t, J=8.7 Hz, 1H), 7.16 (d, J=0.8 Hz, 1H), 6.90-6.78 (m, 3H), 3.74 (s, 3H), 1.38 (s, 6H). ESIMS m/z [M+H]⁺=329.3.

Intermediate 1-10:
4-bromo-6-(4-methoxy-phenoxy)pyrimidine

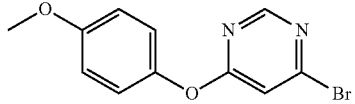 [SMILES: COc1ccc(Oc2cc(Br)ncn2)cc1]

Essentially following the procedures described for intermediate 1-2, using 4-methoxyphenol (156 mg, 1.26 mmol) to afford, after purification by silica gel chromatography, eluting with a gradient of ethyl acetate:cyclohexane—0:100 to 30:70, the title compound as a colorless oil (240 mg, 68% yield). ¹H NMR (300 MHz, CHCl₃-d) 8.53 (d, J=0.7 Hz, 1H), 7.08-7.04 (m, 3H), 6.98-6.93 (m, 2H), 3.83 (s, 3H). ESIMS m/z [M+H]⁺=281.1.

Example 11: 3-[6-(4-methoxyphenoxy)pyrimidin-4-yl]-5,5-dimethyl-imidazolidine-2,4-dione

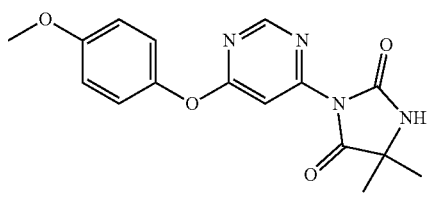

Essentially following the procedures described for example 1-1, using 4-bromo-6-(4-methoxy-phenoxy)pyrimidine (240 mg, 0.85 mmol) to afford, after purification by silica gel chromatography eluting with a gradient of ethyl acetate:cyclohexane—0:100 to 100:0, a semi-preparative purification and a lyophilization using acetonitrile and water, the title compound as a white foam (87 mg, 30% yield). ¹H NMR (300 MHz, DMSO-d₆) 8.74 (d, J 0.8 Hz, 1H), 7.17 (d, J=9.0 Hz, 2H), 7.12 (d, J=0.8 Hz, 1H), 7.00 (d, J=9.0 Hz, 2H), 3.76 (s, 3H), 1.38 (s, 6H). ESIMS m/z [M+H]⁺=329.3.

Intermediate 1-11:
4-bromo-6-(3-fluoro-4-methoxy-phenoxy)pyrimidine

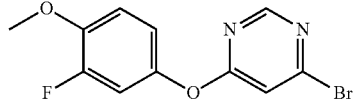 [SMILES: COc1ccc(Oc2cc(Br)ncn2)cc1F]

Essentially following the procedures described for intermediate 1-2, using 3-fluoro-4-methoxyphenol (180 mg, 1.26 mmol) to afford the title compound as an orange solid and pure enough to be used as such (370 mg, 84% yield). ¹H NMR (300 MHz, DMSO-d₆) 8.58 (d, J=0.7 Hz, 1H), 7.52 (d, J=0.7 Hz, 1H), 7.30-7.18 (m, 2H), 7.06-7.00 (m, 1H), 3.84 (s, 3H). ESIMS m/z [M+H]⁺=299.4.

Example 12: 3-[6-(3-fluoro-4-methoxy-phenoxy)pyrimidin-4-yl]-5,5-dimethyl-imidazolidine-2,4-dione

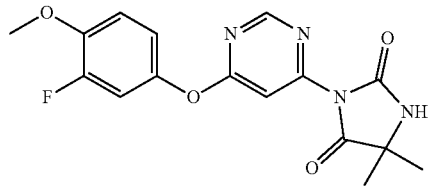

Essentially following the procedures described for example 1-1, using 4-bromo-6-(3-fluoro-4-methoxy-phenoxy)pyrimidine (370 mg, 1.23 mmol) to afford, after purification by silica gel chromatography eluting with a gradient of ethyl acetate:cyclohexane—0:100 to 100:0, the title compound as a white foam (60 mg, 14% yield). ¹H NMR (300 MHz, DMSO-d₆) 8.76 (s, 1H), 8.75 (s, 1H), 7.31 (dd, J=12.0 and 2.8 Hz, 1H), 7.23 (t, J=9.4 Hz, 1H), 7.17 (s, 1H), 7.06 (d, J=9.0 Hz, 1H), 3.85 (s, 3H), 1.38 (s, 6H). ESIMS m/z [M+H]⁺=347.0.

Intermediate 1-12:
4-bromo-6-(4-fluoro-3-methoxy-phenoxy)pyrimidine

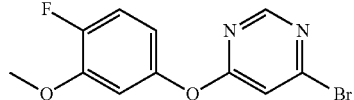 [SMILES: COc1cc(Oc2cc(Br)ncn2)ccc1F]

Essentially following the procedures described for intermediate 1-2, using 4-fluoro-3-methoxyphenol (180 mg, 1.26 mmol) to afford the title compound as an orange solid and pure enough to be used as such (350 mg, 82% yield). $^1$H NMR (300 MHz, DMSO-$d_6$) 8.53 (d, J=0.7 Hz, 1H), 7.51 (d, J=0.7 Hz, 1H), 7.31-7.24 (m, 1H), 7.14-7.10 (m, 1H), 6.85-6.76 (m, 1H), 3.79 (s, 3H). ESIMS m/z [M+H]$^+$=299.3.

Example 13: 3-[6-(3-methoxy-4-fluoro-phenoxy)pyrimidin-4-yl]-5,5-dimethyl-imidazolidine-2,4-dione

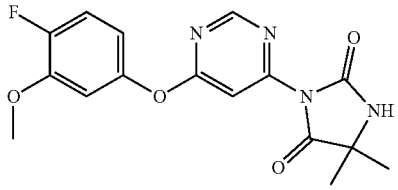 [SMILES: COc1cc(Oc2cc(N3C(=O)NC(C)(C)C3=O)ncn2)ccc1F]

Essentially following the procedures described for example 1-1, using 4-bromo-6-(4-fluoro-3-methoxy-phenoxy)pyrimidine (350 mg, 1.17 mmol) to afford, after purification by silica gel chromatography eluting with a gradient of ethyl acetate:cyclohexane—0:100 to 100:0, the title compound as a white foam (60 mg, 15% yield). $^1$H NMR (300 MHz, DMSO-$d_6$) 8.78 (d, J=0.8 Hz, 1H), 8.75 (s, 1H), 7.31 (dd, J=11.3 and 8.9 Hz, 1H), 7.19-7.14 (m, 2H), 6.85-6.79 (m, 1H), 3.80 (s, 3H), 1.38 (s, 6H). ESIMS m/z [M+H]$^+$=347.0.

Example 14: 3-[6-(4-fluoro-3-methoxy-phenoxy)pyrimidin-4-yl]-1,3-diazaspiro[4.4]nonane-2,4-dione

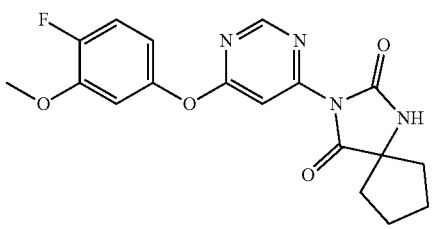 [SMILES: COc1cc(Oc2cc(N3C(=O)NC4(CCCC4)C3=O)ncn2)ccc1F]

Essentially following the procedures described for example 1-1, using 4-bromo-6-(4-fluoro-3-methoxy-phenoxy)pyrimidine (200 mg, 0.67 mmol) and 1,3-diazaspiro[4.4]nonane-2,4-dione (124 mg, 0.80 mmol) to afford, after purification by silica gel chromatography eluting with a gradient of ethyl acetate:cyclohexane—0:100 to 100:0, the title compound as a white solid (81 mg, 31% yield). $^1$H NMR (300 MHz, DMSO-$d_6$) 8.93 (bs, 1H), 8.77 (d, J=0.9 Hz, 1H), 7.29 (dd, J=8.8 and 11.3 Hz, 1H), 7.18 (s, 1H), 7.16 (dd, J=2.8 and 7.4 Hz, 1H), 6.86-6.77 (m, 1H), 3.80 (s, 3H), 2.12-1.99 (m, 2H), 1.90-1.71 (m, 6H). ESIMS m/z [M+H]$^+$=373.3.

Example 15: 3-[6-(4-fluoro-3-methoxy-phenoxy)pyrimidin-4-yl]-1,3-diazaspiro[4.5]decane-2,4-dione

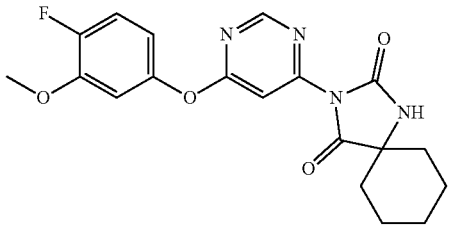 [SMILES: COc1cc(Oc2cc(N3C(=O)NC4(CCCCC4)C3=O)ncn2)ccc1F]

Essentially following the procedures described for example 1-1, using 4-bromo-6-(4-fluoro-3-methoxy-phenoxy)pyrimidine (200 mg, 0.67 mmol) and 1,3-diazaspiro[4.5]decane-2,4-dione (135 mg, 0.80 mmol) to afford, after purification by silica gel chromatography eluting with a gradient of ethyl acetate:cyclohexane—0:100 to 100:0 and a lyophilization using methanol and water, the title compound as a white foam (39 mg, 15% yield). $^1$H NMR (300 MHz, DMSO-$d_6$) 9.14 (bs, 1H), 8.77 (d, J=0.9 Hz, 1H), 7.29 (dd, J=8.8 and 11.3 Hz, 1H), 7.18 (s, 1H), 7.16 (dd, J=2.8 and 7.4 Hz, 1H), 6.86-6.77 (m, 1H), 3.80 (s, 3H), 1.78-1.49 (m, 9H), 1.46-1.25 (m, 1H). ESIMS m/z [M+H]$^+$=387.4.

Intermediate 1-12:
4-bromo-6-(3-fluoro-4-methyl-phenoxy)pyrimidine

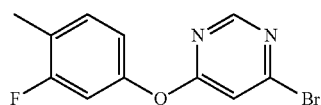

Essentially following the procedures described for intermediate 2, using 3-fluoro-4-methylphenol (160 mg, 1.26 mmol) to afford the title compound as a yellow oil and pure enough to be used as such (380 mg, quantitative yield). $^1$H NMR (300 MHz, DMSO-$d_6$) 8.58 (d, J=0.7 Hz, 1H), 7.55 (d, J=0.7 Hz, 1H), 7.35 (t, J=8.7 Hz, 1H), 7.16 (dd, J=2.3 and 10.5 Hz, 1H), 6.99 (dd, J=2.1 and 8.2 Hz, 1H), 2.22 (s, 3H). ESIMS m/z [M+H]$^+$=283.0.

Example 16: 3-[6-(3-fluoro-4-methyl-phenoxy)pyrimidin-4-yl]-5,5-dimethyl-imidazolidine-2,4-dione

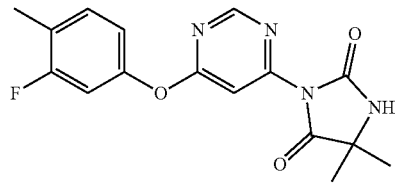

Essentially following the procedures described for example 1-1, using 4-bromo-6-(3-fluoro-4-methyl-phenoxy)pyrimidine (380 mg, 1.34 mmol) to afford, after purification by silica gel chromatography eluting with a gradient of ethyl acetate:cyclohexane—0:100 to 100:0, a semi-preparative purification and a lyophilization using acetonitrile and water, the title compound as a white powder (30 mg, 7% yield). ¹H NMR (300 MHz, DMSO-d₆) 8.76 (bs, 2H), 7.37 (t, J=8.4 Hz, 1H), 7.22-7.19 (m, 2H), 7.02 (d, J=8.4 Hz, 2H), 2.24 (s, 3H), 1.38 (s, 6H). ESIMS m/z [M+H]⁺=331.3.

Intermediate 1-13: 4-bromo-6-(3-methyl-5-methoxy-phenoxy)pyrimidine

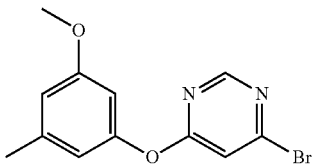 [SMILES: COc1cc(C)cc(Oc2cc(Br)ncn2)c1]

Essentially following the procedures described for intermediate 1-2, using 3-methyl-5-methoxyphenol (175 mg, 1.26 mmol) to afford, after purification by silica gel chromatography, eluting with a gradient of ethyl acetate:cyclohexane—0:100 to 40:60, the title compound as a colorless oil (390 mg, quantitative yield). ¹H NMR (300 MHz, DMSO-d₆) 8.58 (d, J=0.7 Hz, 1H), 7.45 (d, J=0.7 Hz, 1H), 6.70-6.60 (m, 3H), 3.71 (s, 3H), 2.27 (s, 3H). ESIMS m/z [M+H]⁺=295.3.

Example 17: 3-[6-(3-methyl-5-methoxy-phenoxy)pyrimidin-4-yl]-5,5-dimethyl-imidazolidine-2,4-dione

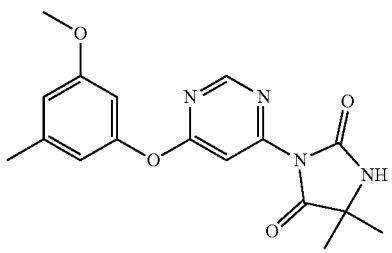

Essentially following the procedures described for example 1-1, using 4-bromo-6-(3-methyl-5-methoxy-phenoxy)pyrimidine (390 mg, 1.32 mmol) to afford, after two purifications by silica gel chromatography eluting with a gradient of ethyl acetate:cyclohexane—0:100 to 100:0, a semi-preparative purification and a lyophilization using acetonitrile and water, the title compound as a white powder (45 mg, 10% yield). ¹H NMR (300 MHz, DMSO-d₆) 8.77 (d, J=0.8 Hz, 1H), 8.75 (s, 1H), 7.14 (d, J=0.8 Hz, 1H), 6.70 (s, 1H), 6.65-6.63 (m, 2H), 3.72 (s, 3H), 2.27 (s, 3H), 1.38 (s, 6H). ESIMS m/z [M+H]⁺=343.4.

Intermediate 1-14: 4-bromo-6-(2-methyl-5-methoxy-phenoxy)pyrimidine

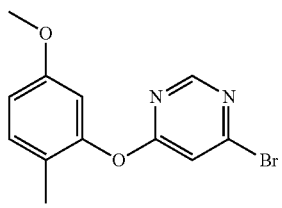 [SMILES: COc1ccc(C)c(Oc2cc(Br)ncn2)c1]

Essentially following the procedures described for intermediate 1-2, using 2-methyl-5-methoxyphenol (175 mg, 1.26 mmol) to afford, after purification by silica gel chromatography, eluting with a gradient of ethyl acetate:cyclohexane—0:100 to 40:60, the title compound as a colorless oil (240 mg, 84% yield). ¹H NMR (300 MHz, DMSO-d₆) 8.56 (d, J=0.7 Hz, 1H), 7.49 (d, J=0.7 Hz, 1H), 7.22 (d, J=8.3 Hz, 1H), 6.83-6.76 (m, 2H), 3.70 (s, 3H), 1.96 (s, 3H). ESIMS m/z [M+H]⁺=295.3.

Example 18: 3-[6-(2-methyl-5-methoxy-phenoxy)pyrimidin-4-yl]-5,5-dimethyl-imidazolidine-2,4-dione

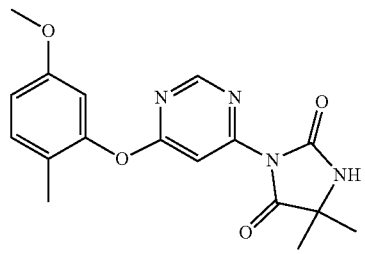 [SMILES: COc1ccc(C)c(Oc2cc(N3C(=O)NC(C)(C)C3=O)ncn2)c1]

Essentially following the procedures described for example 1-1, using 4-bromo-6-(2-methyl-5-methoxy-phenoxy)pyrimidine (310 mg, 1.06 mmol) to afford, after purification by silica gel chromatography eluting with a gradient of ethyl acetate:cyclohexane—0:100 to 100:0, and a lyophilization using acetonitrile and water, the title compound as a white powder (30 mg, 8% yield). ¹H NMR (300 MHz, DMSO-d₆) 8.75 (s, 2H), 7.24 (d, J=7.7 Hz, 1H), 7.14 (d, J=0.8 Hz, 1H), 6.83-6.79 (m, 2H), 3.70 (s, 3H), 1.98 (s, 3H), 1.38 (s, 6H). ESIMS m/z [M+H]⁺=343.0.

Intermediate 1-15: 2-methoxy-3-methyl-benzaldehyde and 2,3-dimethoxy-benzaldehyde

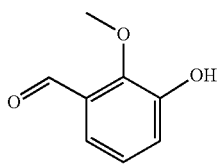 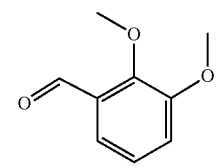

To a stirred solution of 2,3-dihydroxybenzaldehyde (2.0 g, 14.48 mmol) in DMF (25 mL) was added potassium carbonate (2.2 g, 15.90 mmol). The mixture was stirred 30 minutes at room temperature and iodomethane (1.0 mL, 15.90 mmol) was added dropwise. The resulting solution was stirred at room temperature for 18 h. The mixture was hydrolyzed with a saturated aqueous solution of NH₄Cl, extracted using ethyl acetate, the organics were washed with brine, dried over MgSO₄ and concentrated in vacuo before purification by silica gel flash chromatography eluting with a gradient of cyclohexane:ethyl acetate—100:0 to 75:25 to give as the first eluting compound 2,3-dimethoxy-benzaldehyde as a colorless gum (450 mg, 19% yield) and as the last eluting compound 2-methoxy-3-methyl-benzaldehyde as a white solid (1.27 g, 57% yield). 2,3-dimethoxy-benzaldehyde: ¹H NMR (300 MHz, CHCl₃-d) 10.43 (s, 1H), 7.45-

7.38 (m, 1H), 7.18-7.10 (m, 2H), 3.98 (s, 3H), 3.91 (s, 3H). 2-methoxy-3-methyl-benzaldehyde: $^1$H NMR (300 MHz, CHCl$_3$-d) 10.26 (s, 1H), 7.45-7.38 (dd, J=1.8 and 7.6 Hz, 1H), 7.26-7.10 (m, 2H), 5.79 (s, 1H), 3.97 (s, 3H).

Intermediate 1-16: 2-methoxy-3-methyl-phenol

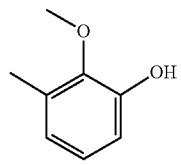

Essentially following the procedures described for intermediate 1-1, using 2-methoxy-3-methylbenzaldehyde (1.27 g, 8.34 mmol) to afford, after purification by silica gel flash chromatography eluting with a gradient of cyclohexane:ethyl acetate-100:0 to 80:20, the title compound as a colorless oil (975 mg, 84% yield). $^1$H NMR (300 MHz, CHCl$_3$-d) 6.91 (app. t, J=7.8 Hz, 1H), 6.80 (dd, J=1.6 and 8.0 Hz, 1H), 6.69 (dd, J=0.7 and 7.5 Hz, 1H), 5.62 (bs, 1H), 3.80 (s, 3H), 2.30 (s, 3H).

Intermediate 1-17: 4-bromo-6-(2-methoxy-3-methyl-phenoxy)pyrimidine

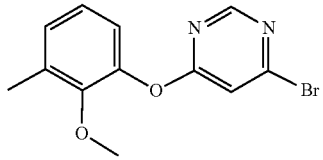 [SMILES: COc1c(C)cccc1Oc1cc(Br)ncn1]

Essentially following the procedures described for intermediate 1-2, using 2-methoxy-3-methyl-phenol (300 mg, 2.17 mmol) to afford the title compound as a yellow oil and pure enough to be used as such (550 mg, 85% yield). $^1$H NMR (300 MHz, DMSO-d$_6$) 8.56 (d, J=0.7 Hz, 1H), 7.57 (d, J=0.7 Hz, 1H), 7.15-7.10 (m, 1H), 7.09-7.05 (m, 2H), 3.70 (s, 3H), 1.96 (s, 3H). ESIMS m/z [M+H]$^+$=295.2.

Example 19: 3-[6-(2-methoxy-3-methyl-phenoxy)pyrimidin-4-yl]-5,5-dimethyl-imidazolidine-2,4-dione

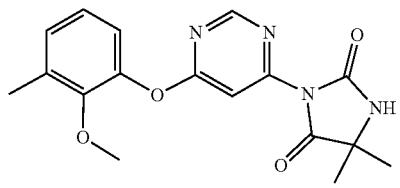

Essentially following the procedures described for example 1-1, using 4-bromo-6-(2-methoxy-3-methyl-phenoxy)pyrimidine (345 mg, 1.17 mmol) to afford, after purification by silica gel chromatography eluting with a gradient of ethyl acetate:cyclohexane—0:100 to 100:0, a semi-preparative purification, a size exclusion chromatography and a lyophilization using acetonitrile and water, the title compound as a white powder (16 mg, 5% yield). $^1$H NMR (300 MHz, DMSO-d$_6$) 8.76 (s, 1H), 8.74 (d, J=0.9 Hz, 1H), 7.22 (d, J=0.9 Hz, 1H), 7.15-7.07 (m, 3H), 3.61 (s, 3H), 2.24 (s, 3H), 1.39 (s, 6H). ESIMS m/z [M+H]$^+$=343.3.

Intermediate 1-18: 4-bromo-6-(3-methyl-4-methoxy-phenoxy)pyrimidine

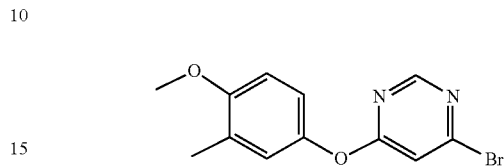

Essentially following the procedures described for intermediate 1-2, using 3-methyl-4-methoxy-phenol (300 mg, 2.17 mmol) to afford the title compound as a yellow oil and pure enough to be used as such (610 mg, 95% yield). $^1$H NMR (300 MHz, DMSO-d$_6$) 8.56 (d, J=0.7 Hz, 1H), 7.40 (d, J=0.7 Hz, 1H), 7.02-6.93 (m, 3H), 3.78 (s, 3H), 2.13 (s, 3H). ESIMS m/z [M+H]$^+$=295.2.

Example 20: 3-[6-(3-methyl-4-methoxy-phenoxy)pyrimidin-4-yl]-5,5-dimethyl-imidazolidine-2,4-dione

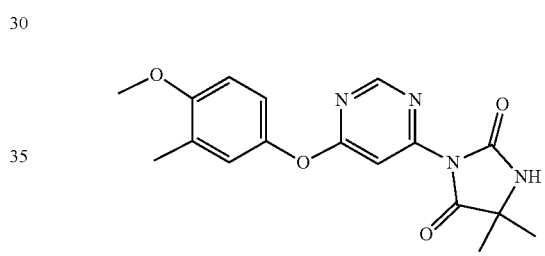

Essentially following the procedures described for example 1-1, using 4-bromo-6-(3-methyl-4-methoxy-phenoxy)pyrimidine (300 mg, 1.01 mmol) to afford, after purification by silica gel chromatography eluting with a gradient of ethyl acetate:cyclohexane—0:100 to 100:0, a size exclusion chromatography and a lyophilization using acetonitrile and water, the title compound as a white powder (99 mg, 28% yield). $^1$H NMR (300 MHz, DMSO-d$_6$) 8.75 (s, 1H), 8.73 (s, 1H), 7.10 (s, 1H), 7.05-6.95 (m, 3H), 3.79 (s, 3H), 2.14 (s, 3H), 1.38 (s, 6H). ESIMS m/z [M+H]$^+$=343.3.

Intermediate 1-19: 4-bromo-6-(2-methoxy-4-methyl-phenoxy)pyrimidine

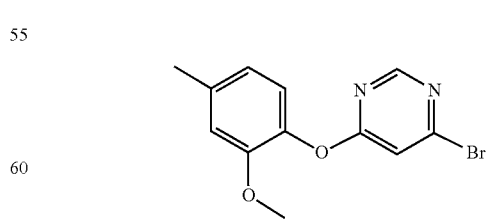

Essentially following the procedures described for intermediate 1-2, using 2-methoxy-4-methyl-phenol (175 mg, 1.26 mmol) to afford, after purification by silica gel chromatography eluting with a gradient of ethyl acetate:cyclohexane—0:100 to 20:80 the title compound as a white powder (350 mg, 94% yield). $^1$H NMR (300 MHz, CDCl$_3$-d) 8.50 (s, 1H), 7.09 (s, 1H), 6.99 (d, J=7.8 Hz, 1H), 6.88-6.75 (m, 2H), 3.75 (s, 3H), 2.38 (s, 3H).

Example 21: 3-[6-(2-methoxy-4-methyl-phenoxy)pyrimidin-4-yl]-5,5-dimethyl-imidazolidine-2,4-dione

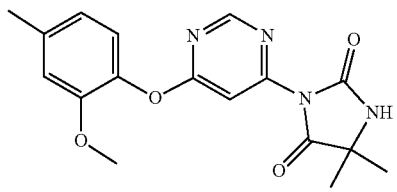

Essentially following the procedures described for example 1-1, using 4-bromo-6-(2-methoxy-4-methyl-phenoxy)pyrimidine (350 mg, 1.19 mmol) to afford, after purification by silica gel chromatography eluting with a gradient of ethyl acetate:cyclohexane—0:100 to 100:0 and a lyophilization using acetonitrile and water, the title compound as a white powder (136 mg, 33% yield). $^1$H NMR (300 MHz, DMSO-d$_6$) 8.72 (s, 1H), 8.70 (d, J=0.9 Hz, 1H), 7.11 (d, J=0.9 Hz, 1H), 7.08 (d, J=8.1 Hz, 1H), 7.00 (d, J=1.5 Hz, 1H), 6.790 (dd, J=1.2 and 8.1 Hz, 1H), 3.68 (s, 3H), 2.33 (s, 3H), 1.38 (s, 6H). ESIMS m/z [M+H]$^+$=343.2.

Intermediate 1-20: 5-hydroxy-2-methyl-benzonitrile

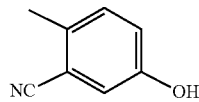

To a stirred solution of 5-Amino-2-methylbenzonitrile (4.00 g, 30.27 mmol) in 33% sulfuric acid (45 mL) was added a solution of sodium nitrite (2.09 g, 30.27 mmol) in water (15 mL) at 5° C. The temperature was kept below 5° C. In a separated flask, concentrated sulfuric acid (30 mL) was added cautiously to a stirred solution of sodium sulfate (21.50 g, 151.33 mmol) in water (15 mL). The slurry was heated to reflux. The prepared diazonium salt was added dropwise to the refluxing mixture and the reflux was continued for 2 hours. The mixture was cooled slowly to room temperature. The mixture was extracted with ethyl acetate (2×100 mL) and the combined extracts were washed with water (2×150 mL). The organic layer was extracted with aqueous 10% NaOH solution (2×100 mL). The alkaline extract was acidified with conc. HCl and extracted with EtOAc (2×100 mL). The combined organic layers were dried over MgSO$_4$, filtered and the solvent was evaporated in vacuo to afford the title compound as a red solid and pure enough to be used as such (2400 mg, 60% yield). $^1$H NMR (300 MHz, CHCl$_3$-d) 9.46 (bs, 1H), 7.16 (d, J=8.4 Hz, 1H), 7.06 (d, J=2.7 Hz, 1H), 6.97 (dd, J=8.4 and 2.7 Hz, 1H), 2.45 (s, 3H).

Intermediate 1-21: 5-(6-bromopyrimidin-4-yl)oxy-2-methyl-benzonitrile

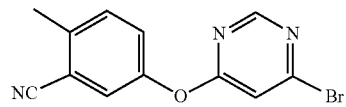 [SMILES: Cc1ccc(Oc2cc(Br)ncn2)cc1C#N]

Essentially following the procedures described for intermediate 1-2, using intermediate 1-17 (1.0 g, 7.51 mmol) to afford, after purification by silica gel chromatography, eluting with a gradient of dichloromethane:cyclohexane—0:100 to 100:0, the title compound as a yellow solid (970 mg, 45% yield). $^1$H NMR (300 MHz, CHCl$_3$-d) 8.51 (d, J=0.7 Hz, 1H), 7.41-7.37 (m, 2H), 7.30-7.25 (m, 1H), 7.19 (d, J=1.0 Hz, 1H), 2.58 (s, 3H).

Example 22: 5-[6-(4,4-dimethyl-2,5-dioxo-imidazolidin-1-yl)pyrimidin-4-yl]oxy-2-methyl-benzonitrile

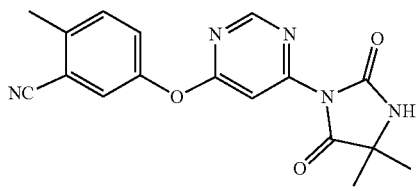 [SMILES: Cc1ccc(Oc2cc(N3C(=O)NC(C)(C)C3=O)ncn2)cc1C#N]

Essentially following the procedures described for example 1-1, using 5-(6-bromopyrimidin-4-yl)oxy-2-methyl-benzonitrile (970 mg, 3.34 mmol) to afford, after purification by silica gel chromatography eluting with a gradient of ethyl acetate:cyclohexane—0:100 to 100:0, a semi-preparative purification and a lyophilization using acetonitrile and water, the title compound as a white powder (180 mg, 16% yield). $^1$H NMR (300 MHz, DMSO-d$_6$) 8.80 (d, J=0.9 Hz, 1H), 7.85 (s, 1H), 7.58-7.56 (m, 2H), 7.30 (d, J=0.9 Hz, 1H), 2.52 (s, 3H), 1.42 (s, 6H). ESIMS m/z [M+H]$^+$=338.3.

Intermediate 1-22: 4-bromo-6-[(3-pyridyl)-oxy]pyrimidine

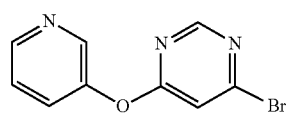 [SMILES: Brc1cc(Oc2cccnc2)ncn1]

Essentially following the procedures described for intermediate 1-2, using 3-hydroxypyridine (120 mg, 1.26 mmol) to afford, after purification by silica gel chromatography, eluting with a gradient of ethyl acetate:cyclohexane—0:100 to 50:50, the title compound as a yellow oil (230 mg, 72% yield). $^1$H NMR (300 MHz, DMSO-d$_6$) 8.58 (d, J=0.7 Hz, 1H), 8.54-8.49 (m, 2H), 7.78-7.73 (m, 1H), 7.69 (d, J=0.8 Hz, 1H), 7.51 (dd, J=8.4 and 2.7 Hz, 1H).

Example 23: 5,5-dimethyl-3-[6-(3-pyridyloxy)pyrimidin-4-yl]imidazolidine-2,4-dione

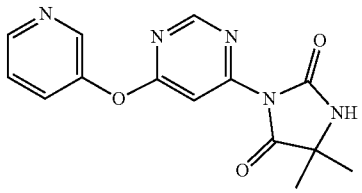 [SMILES: CC1(C)NC(=O)N(c2cc(Oc3cccnc3)ncn2)C1=O]

Essentially following the procedures described for example 1-1, using 4-bromo-6-[(3-pyridyl)-oxy]pyrimidine (230 mg, 0.89 mmol) to afford, after two purifications by silica gel chromatography (first eluting with a gradient of ethyl acetate:cyclohexane—0:100 to 100:0; second eluting with a gradient of methanol:dichloromethane—0:100 to 90:10), a size exclusion chromatography and a lyophilization using acetonitrile and water, the title compound as a white powder (35 mg, 13% yield). $^1$H NMR (300 MHz, DMSO-$d_6$) 8.78 (bs, 1H), 8.77 (s, 1H), 8.57 (d, J=2.7 Hz, 1H), 8.52 (dd, J=4.7 and 1.1 Hz, 1H), 7.81-7.77 (m, 1H), 7.53 (dd, J=8.4 and 4.7 Hz, 1H), 7.31 (s, 1H), 1.40 (s, 6H). ESIMS m/z [M+H]$^+$=300.0.

Intermediate 1-23: 4-bromo-6-[(6-methyl-3-pyridyl)-oxy]pyrimidine

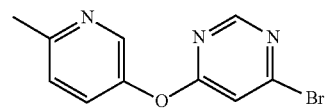

Essentially following the procedures described for intermediate 1-2, using 3-hydroxy-6-methyl-pyridine (140 mg, 1.26 mmol) to afford, after purification by silica gel chromatography, eluting with a gradient of ethyl acetate:cyclohexane—0:100 to 80:20, the title compound as a yellow oil (290 mg, 86% yield). $^1$H NMR (300 MHz, DMSO-$d_6$) 8.57 (d, J=0.7 Hz, 1H), 8.36 (d, J=2.7 Hz, 1H), 7.64 (d, J=0.7 Hz, 1H), 7.61 (dd, J=8.4 and 2.7 Hz, 1H), 7.34 (d, J=8.4 Hz, 1H), 2.48 (s, 3H).

Example 24: 5,5-dimethyl-3-[6-[(6-methyl-3-pyridyl)oxy]pyrimidin-4-yl]imidazolidine-2,4-dione

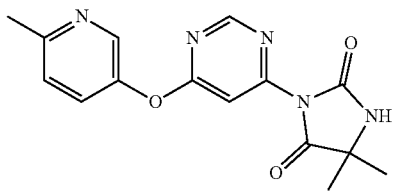

Essentially following the procedures described for example 1-1, using 4-bromo-6-[(6-methyl-3-pyridyl)-oxy]pyrimidine (290 mg, 1.09 mmol) to afford, after purification by silica gel chromatography eluting with a gradient of ethyl acetate:cyclohexane—0:100 to 100:0, a semi-preparative purification, a size exclusion chromatography and a lyophilization using acetonitrile and water, the title compound as a white powder (35 mg, 10% yield). $^1$H NMR (300 MHz, DMSO-$d_6$) 8.77 (bs, 1H), 8.76 (d, J=0.8 Hz, 1H), 8.39 (d, J=2.8 Hz, 1H), 7.65 (dd, J=8.4 and 2.8 Hz, 1H), 7.36 (d, J=8.4 Hz, 1H), 7.27 (d, J=0.8 Hz, 1H), 2.48 (s, 3H), 1.39 (s, 6H). ESIMS m/z [M+H]$^+$=314.3.

Intermediate 1-24: 4-bromo-6-[(5-methoxy-3-pyridyl)-oxy]pyrimidine

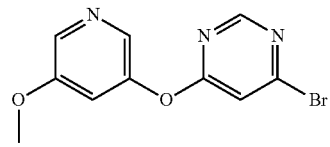 [SMILES: COc1cncc(Oc2cc(Br)ncn2)c1]

Essentially following the procedures described for intermediate 1-2, using 3-hydroxy-5-methoxy-pyridine (160 mg, 1.26 mmol) to afford, after purification by silica gel chromatography, eluting with a gradient of ethyl acetate:cyclohexane—0:100 to 60:40, the title compound as a yellow oil (250 mg, 70% yield). $^1$H NMR (300 MHz, CHCl$_3$-d) 8.52 (d, J=0.7 Hz, 1H), 8.25 (d, J=2.5 Hz, 1H), 8.11 (d, J=2.1 Hz, 1H), 7.19 (d, J=0.7 Hz, 1H), 7.04 (t, J=2.4 Hz, 1H), 3.87 (s, 3H). ESIMS m/z [M+H]$^+$=282.0.

Example 25: 5,5-dimethyl-3-[6-[(5-methoxy-3-pyridyl)oxy]pyrimidin-4-yl]imidazolidine-2,4-dione

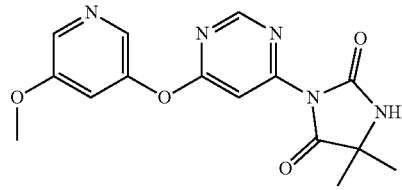 [SMILES: COc1cncc(Oc2cc(N3C(=O)NC(C)(C)C3=O)ncn2)c1]

Essentially following the procedures described for example 1-1, using 4-bromo-6-[(5-methoxy-3-pyridyl)-oxy]pyrimidine (250 mg, 0.90 mmol) to afford, after purification by silica gel chromatography eluting with a gradient of methanol:dichloromethane—0:100 to 90:10, a semi-preparative purification and a lyophilization using acetonitrile and water, the title compound as a white powder (37 mg, 13% yield). $^1$H NMR (300 MHz, DMSO-$d_6$) 8.79-8.77 (m, 2H), 8.26 (d, J=2.5 Hz, 1H), 8.16 (d, J=2.1 Hz, 1H), 7.48 (t, J=2.3 Hz, 1H), 7.29 (s, 1H), 3.82 (s, 3H), 1.39 (s, 6H). ESIMS m/z [M+H]$^+$=330.2.

Intermediate 1-25: 4-bromo-6-(2-methyl-phenoxy)pyrimidine

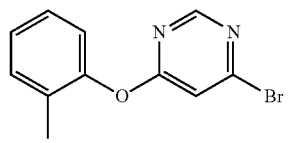

Essentially following the procedures described for intermediate 1-2, using o-cresol (136 mg, 1.26 mmol) to afford, after purification by silica gel chromatography eluting with a gradient of ethyl acetate:cyclohexane—0:100 to 20:80, the title compound as a colorless oil (270 mg, 81% yield). $^1$H NMR (300 MHz, CHCl$_3$-d) 8.53 (d, J=0.7 Hz, 1H), 7.36-7.19 (m, 3H), 7.16-7.00 (m, 2H), 2.14 (s, 3H).

Example 26: 3-[6-(2-methylphenoxy)pyrimidin-4-yl]-5,5-dimethyl-imidazolidine-2,4-dione

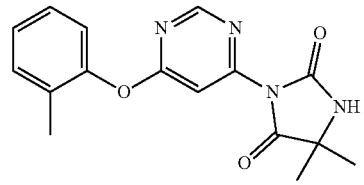 [SMILES: Cc1ccccc1Oc1cc(N2C(=O)NC(C)(C)C2=O)ncn1]

Essentially following the procedures described for example 1-1, using 4-bromo-6-(2-methyl-phenoxy)pyrimidine (270 mg, 1.02 mmol) to afford, after two purifications by silica gel chromatography eluting with a gradient of ethyl acetate:cyclohexane—0:100 to 80:20, and a Sephadex exclusion chromatography, the title compound as a white powder (65 mg, 20% yield). $^1$H NMR (300 MHz, DMSO-d$_6$) 8.76-8.71 (m, 2H), 7.37-7.11 (m, 5H), 2.08 (s, 3H), 1.38 (s, 6H). ESIMS m/z [M+H]$^+$=313.2.

Intermediate 1-26: 4-bromo-6-(3-methyl-phenoxy)pyrimidine

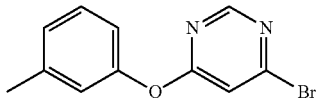

Essentially following the procedures described for intermediate 1-2, using m-cresol (136 mg, 1.26 mmol) to afford, after purification by silica gel chromatography, eluting with a gradient of ethyl acetate:cyclohexane—0:100 to 30:70, the title compound as a yellow oil (260 mg, 78% yield). $^1$H NMR (300 MHz, CHCl$_3$-d) 8.54 (d, J=0.7 Hz, 1H), 7.33 (t, J=7.4 Hz, 1H), 7.12 (d, J=7.4 Hz, 1H), 7.07 (d, J=0.7 Hz, 1H), 6.97-6.88 (m, 2H), 2.39 (s, 3H).

Example 27: 3-[6-(3-methylphenoxy)pyrimidin-4-yl]-5,5-dimethyl-imidazolidine-2,4-dione

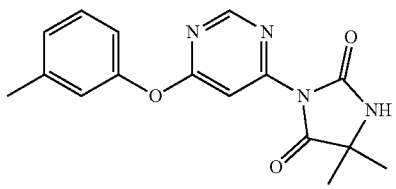

Essentially following the procedures described for example 1-1, using 4-bromo-6-(3-methyl-phenoxy)pyrimidine (260 mg, 0.98 mmol) to afford, after two purifications by silica gel chromatography eluting with a gradient of ethyl acetate:cyclohexane—0:100 to 80:20, and a lyophilization using acetonitrile and water, the title compound as a white solid (85 mg, 28% yield). $^1$H NMR (300 MHz, DMSO-d$_6$) 8.81-8.72 (m, 2H), 7.34 (t, J=7.8 Hz, 1H), 7.16 (s, 1H), 7.14-6.97 (m, 3H), 2.32 (s, 3H), 1.38 (s, 6H). ESIMS m/z [M+H]$^+$=313.2.

Intermediate 1-27: 4-bromo-6-(4-methyl-phenoxy)pyrimidine

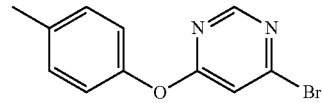

Essentially following the procedures described or intermediate 1-2, using p-cresol (136 mg, 1.26 mmol) to afford, after purification by silica gel chromatography, eluting with a gradient of ethyl acetate:cyclohexane—0:100 to 20:80, the title compound as a colorless oil (325 mg, 97% yield). $^1$H NMR (300 MHz, CHCl$_3$-d) 8.53 (d, J=0.7 Hz, 1H), 7.30-7.18 (m, 2H), 7.10-6.96 (m, 3H), 2.38 (s, 3H).

Example 28: 3-[6-(4-methylphenoxy)pyrimidin-4-yl]-5,5-dimethyl-imidazolidine-2,4-dione

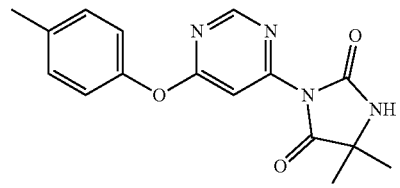

Essentially following the procedures described for example 1-1, using 4-bromo-6-(4-methyl-phenoxy)pyrimidine (325 mg, 1.23 mmol) to afford, after two purifications by silica gel chromatography eluting with a gradient of ethyl acetate:cyclohexane—0:100 to 60:40, and a Sephadex exclusion chromatography, the title compound as a white powder (124 mg, 32% yield). $^1$H NMR (300 MHz, DMSO-d$_6$) 8.74 (s, 1H), 7.26 (d, J=8.4 Hz, 2H), 7.18-7.08 (m, 3H), 2.32 (s, 3H), 1.38 (s, 6H). ESIMS m/z [M+H]$^+$=313.1.

Intermediate 1-28: 4-bromo-6-(3,4-dimethyl-phenoxy)pyrimidine

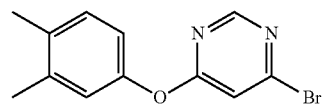 [SMILES: Cc1ccc(Oc2cc(Br)ncn2)cc1C]

Essentially following the procedures described for intermediate 1-2, using 3,4-dimethylphenol (154 mg, 1.26 mmol) to afford, after purification by silica gel chromatography, eluting with a gradient of ethyl acetate:cyclohexane—0:100 to 30:70, the title compound as a colorless oil (300 mg, 85% yield). $^1$H NMR (300 MHz, CHCl$_3$-d) 8.53 (d, J=0.7 Hz, 1H), 7.19 (d, J=8.2 Hz, 1H), 7.05 (s, 1H), 6.90 (d, J=2.3 Hz, 1H), 6.85 (dd, J=2.5 and 8.1 Hz, 1H), 2.27 (s, 6H).

Example 29: 3-[6-(3,4-dimethylphenoxy)pyrimidin-4-yl]-5,5-dimethyl-imidazolidine-2,4-dione

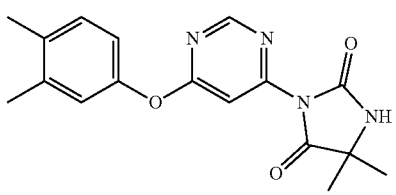

Essentially following the procedures described for example 1-1, using 4-bromo-6-(3,4-dimethyl-phenoxy)pyrimidine (300 mg, 1.07 mmol) to afford, after purification by silica gel chromatography eluting with a gradient of ethyl acetate:cyclohexane—0:100 to 70:30, a semi-preparative purification and a lyophilization using acetonitrile and water, the title compound as a white powder (62 mg, 17% yield). $^1$H NMR (300 MHz, DMSO-$d_6$) 8.74 (d, J=0.7 Hz, 1H), 8.73 (bs, 1H), 7.20 (d, J=8.1 Hz, 1H), 7.12 (d, J=0.7 Hz, 1H), 7.02 (d, J=2.5 Hz, 1H), 6.94 (dd, J=2.5 and 8.1 Hz, 1H), 2.22 (s, 6H), 1.38 (s, 6H). ESIMS m/z [M+H]$^+$=327.2.

Intermediate 1-29: 4-bromo-6-(3-ethyl-4-methyl-phenoxy)pyrimidine

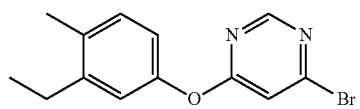 [SMILES: CCc1cc(Oc2cc(Br)ncn2)ccc1C]

Essentially following the procedures described for intermediate 1-2, using 3-ethyl-4-methylphenol (550 mg, 4.04 mmol) to afford, after purification by silica gel chromatography, eluting with a gradient of ethyl acetate:cyclohexane—0:100 to 30:70, the title compound as a colorless oil (1.12 g, 95% yield). $^1$H NMR (300 MHz, CHCl$_3$-d) 8.55 (d, J=0.8 Hz, 1H), 7.43 (d, J=0.8 Hz, 1H), 7.19 (d, J=8.2 Hz, 1H), 6.98 (d, J=2.4 Hz, 1H), 6.92 (dd, J=2.4 and 8.2 Hz, 1H), 2.56 (q, J=7.5 Hz, 2H), 2.25 (s, 3H), 1.12 (dd, J=7.5 Hz, 3H).

Example 30: 3-[6-(3-ethyl-4-methylphenoxy)pyrimidin-4-yl]-5,5-dimethyl-imidazolidine-2,4-dione

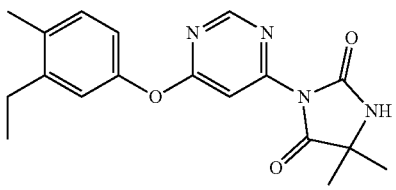

Essentially following the procedures described for example 1-1, using 4-bromo-6-(3-ethyl-4-methyl-phenoxy)pyrimidine (500 mg, 1.71 mmol) to afford, after purification by silica gel chromatography eluting with a gradient of ethyl acetate:cyclohexane—0:100 to 75:25 and a lyophilization using acetonitrile and water, the title compound as a white powder (106 mg, 18% yield). $^1$H NMR (300 MHz, DMSO-$d_6$) 8.77 (s, 1H), 8.76 (bs, 1H), 7.23 (d, J=8.2 Hz, 1H), 7.14 (s, 1H), 7.02 (d, J=2.4 Hz, 1H), 6.97 (dd, J=2.4 and 8.2 Hz, 1H), 2.59 (q, J=7.5 Hz, 2H), 2.28 (s, 3H), 1.15 (dd, J=7.5 Hz, 3H). ESIMS m/z [M+H]$^+$=341.3.

Intermediate 1-30: 4-bromo-6-indan-5-yloxy-pyrimidine

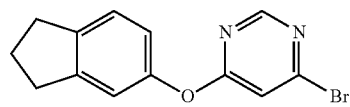 [SMILES: Brc1cc(Oc2ccc3c(c2)CCC3)ncn1]

Essentially following the procedures described for intermediate 1-2, using 5-hydroxyindan (170 mg, 1.26 mmol) to afford, after purification by silica gel chromatography, eluting with a gradient of ethyl acetate:cyclohexane—0:100 to 30:70 and a Sephadex exclusion chromatography, the title compound as a colorless oil (220 mg, 60% yield). $^1$H NMR (300 MHz, CHCl$_3$-d) 8.77 (bs, 1H), 8.54 (d, J=0.7 Hz, 1H), 7.26 (d, J=8.0 Hz, 1H), 7.07 (d, J=0.7 Hz, 1H), 6.97 (d, J=2.2 Hz, 1H), 6.87 (dd, J=2.2 and 8.0 Hz, 1H), 2.93 (dd, J=7.3 and 12.8 Hz, 4H), 2.13 (quint, J=7.4 Hz, 2H).

Example 31: 3-(6-indan-5-yloxypyrimidin-4-yl)-5,5-dimethyl-imidazolidine-2,4-dione

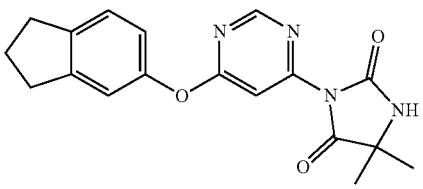 [SMILES: CC1(C)NC(=O)N(c2cc(Oc3ccc4c(c3)CCC4)ncn2)C1=O]

Essentially following the procedures described for example 1-1, using 4-bromo-6-indan-5-yloxy-pyrimidine (220 mg, 0.76 mmol) to afford, after purification by silica gel chromatography eluting with a gradient of ethyl acetate:cyclohexane—0:100 to 75:25 and a lyophilization using methanol and water, the title compound as a white powder (126 mg, 48% yield). $^1$H NMR (300 MHz, DMSO-$d_6$) 8.74 (bs, 2H), 7.27 (d, J=8.1 Hz, 1H), 7.13 (d, J=0.8 Hz, 1H), 7.08 (d, J=1.8 Hz, 1H), 6.95 (dd, J=1.8 and 8.1 Hz, 1H), 2.92-2.82 (m, 4H), 2.04 (quint, J=7.4 Hz, 2H), 1.38 (s, 6H). ESIMS m/z [M+H]$^+$=339.3.

Intermediate 1-31: 4-bromo-6-indan-4-yloxy-pyrimidine

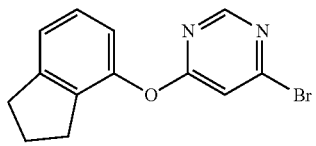 [SMILES: Brc1cc(Oc2cccc3c2CCC3)ncn1]

Essentially following the procedures described for intermediate 1-2, using 4-hydroxyindan (170 mg, 1.26 mmol) to afford, after purification by silica gel chromatography, eluting with a gradient of ethyl acetate:cyclohexane—0:100 to 30:70, the title compound as a colorless oil (360 mg, 98% yield). ESIMS m/z [M+H]$^+$=291.2-293.2.

Example 32: 3-(6-indan-4-yloxypyrimidin-4-yl)-5,5-dimethyl-imidazolidine-2,4-dione

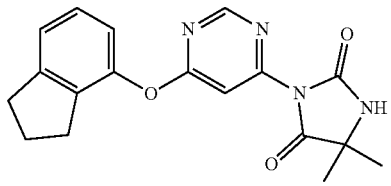 [SMILES: CC1(C)NC(=O)N(c2cc(Oc3cccc4c3CCC4)ncn2)C1=O]

Essentially following the procedures described for example 1-1, using 4-bromo-6-indan-4-yloxy-pyrimidine (360 mg, 1.24 mmol) to afford, after purification by silica gel chromatography eluting with a gradient of ethyl acetate:cyclohexane—0:100 to 100:0, a semi-preparative purification and a lyophilization using methanol and water, the title compound as a white powder (106 mg, 25% yield). $^1$H NMR (300 MHz, DMSO-d$_6$) 8.75 (bs, 2H), 7.30-7.15 (m, 2H), 7.15 (d, J=0.9 Hz, 1H), 6.98 (d, J=6.8 Hz, 1H), 2.92 (t, J=7.4 Hz, 2H), 2.62 (t, J=7.4 Hz, 2H), 1.99 (quint, J=7.4 Hz, 2H), 1.38 (s, 6H). ESIMS m/z [M+H]$^+$=339.3.

Intermediate 1-32: 4-bromo-6-chroman-7-yloxy-pyrimidine

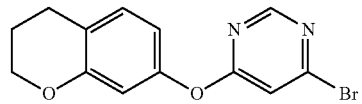 [SMILES: Brc1cc(Oc2ccc3c(c2)OCCC3)ncn1]

Essentially following the procedures described for intermediate 1-2, using chroman-7-ol (150 mg, 1.26 mmol) to afford, after purification by silica gel chromatography, eluting with a gradient of ethyl acetate:cyclohexane—0:100 to 15:85, the title compound as a colorless oil (310 mg, 80% yield). ESIMS m/z [M+H]$^+$=307.1-309.1.

Example 33: 3-(6-chroman-7-yloxypyrimidin-4-yl)-5,5-dimethyl-imidazolidine-2,4-dione

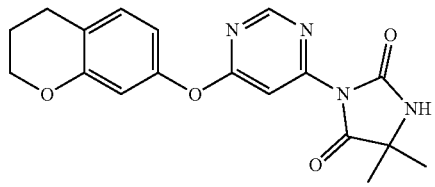 [SMILES: CC1(C)NC(=O)N(c2cc(Oc3ccc4c(c3)OCCC4)ncn2)C1=O]

Essentially following the procedures described for example 1-1, using 4-bromo-6-chroman-7-yloxy-pyrimidine (310 mg, 1.01 mmol) to afford, after purification by silica gel chromatography eluting with a gradient of ethyl acetate:cyclohexane—0:100 to 100:0, a Sephadex exclusion chromatography and a lyophilization using acetonitrile and water, the title compound as a white powder (71 mg, 20% yield). $^1$H NMR (300 MHz, DMSO-d$_6$) 8.75 (d, J=0.8 Hz, 1H), 8.74 (bs, 1H), 7.15-7.08 (m, 2H), 6.67 (dd, J=2.4 and 8.2 Hz, 1H), 6.62 (d, J=2.4 Hz, 1H), 4.17-4.09 (m, 2H), 2.78-2.69 (m, 2H), 1.97-1.86 (m, 2H), 1.38 (s, 6H). ESIMS m/z [M+H]$^+$=355.3.

Intermediate 1-33: 4-(benzofuran-6-yloxy)-6-bromo-pyrimidine

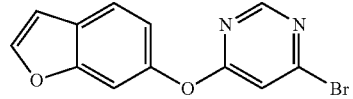 [SMILES: Brc1cc(Oc2ccc3ccoc3c2)ncn1]

Essentially following the procedures described for intermediate 1-2, using benzofuran-6-ol (120 mg, 0.90 mmol) to afford, after purification by silica gel chromatography, eluting with a gradient of ethyl acetate:cyclohexane—0:100 to 60:40, the title compound as a colorless oil (190 mg, 73% yield). $^1$H NMR (300 MHz, CHCl$_3$-d) 8.54 (d, J=0.8 Hz, 1H), 7.67 (d, J=2.2 Hz, 1H), 7.64 (d, J=8.4 Hz, 1H), 7.34-7.32 (m, 1H), 7.11 (d, J=0.8 Hz, 1H), 7.04 (dd, J=2.1 and 8.4 Hz, 1H), 6.81 (dd, J=0.8 and 2.2 Hz, 1H).

Example 34: 3-[6-(benzofuran-6-yloxy)pyrimidin-4-yl]-5,5-dimethyl-imidazolidine-2,4-dione

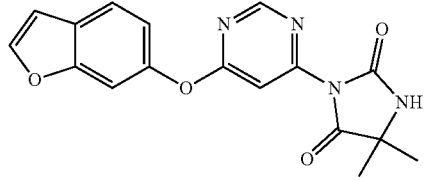 [SMILES: CC1(C)NC(=O)N(c2cc(Oc3ccc4ccoc4c3)ncn2)C1=O]

Essentially following the procedures described for example 1-1, using 4-(benzofuran-6-yloxy)-6-bromo-pyrimidine (190 mg, 0.65 mmol) to afford, after purification by silica gel chromatography eluting with a gradient of ethyl acetate:dichloromethane—0:100 to 75:25, a semi-preparative purification and a lyophilization using methanol and water, the title compound as a white foam (60 mg, 27% yield). $^1$H NMR (300 MHz, DMSO-d$_6$) 8.76 (d, J=0.8 Hz, 1H), 8.74 (bs, 1H), 8.05 (d, J=2.2 Hz, 1H), 7.72 (d, J=8.4 Hz, 1H), 7.61 (d, J=1.3 Hz, 1H), 7.18 (d, J=0.8 Hz, 1H), 7.15 (dd, J=2.1 and 8.4 Hz, 1H), 7.00 (dd, J=0.8 and 2.1 Hz, 1H), 1.38 (s, 6H). ESIMS m/z [M+H]$^+$=339.3.

Intermediate 1-34: 4-methoxy-3,5-dimethyl-phenol

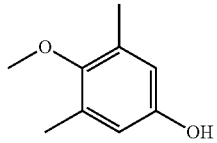

To a solution of 4-methoxy-3,5-dimethyl-benzaldehyde (2.0 g, 12.18 mmol) in DCM (24 mL) under argon, was added at 0° C. mCPBA (3.82 g, 17.05 mmol, purity=77%).

The resulting suspension was stirred for 5 min at 0° C., allowed to warm to room temperature and stirred for 2 h. The resulting suspension was washed with 10% aqueous Na₂SO₃. The organic layer was dried over MgSO₄, filtered and concentrated in vacuo. The crude residue was dissolved in 10:1 MeOH:6M HCl (44 mL), and stirred overnight at RT. The orange solution was concentrated in vacuo, poured into AcOEt (50 mL), and washed with sat. aq. NaHCO₃ to remove benzoic acid, then washed with brine, dried over MgSO₄, filtered, and concentrated in vacuo. The crude material was purified by silica gel chromatography, eluting with a gradient of ethyl acetate:cyclohexane—0:100 to 20:80, the title compound as an off-with solid (685 mg, 37% yield). ¹H NMR (300 MHz, DMSO-d₆) 8.88 (s, 1H), 6.36 (s, 2H), 3.52 (s, 3H), 2.09 (s, 6H).

Intermediate 1-35: 4-bromo-6-(4-methoxy-3,5-dimethyl-phenoxy)pyrimidine

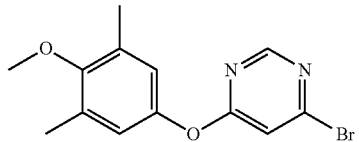 [SMILES: COc1c(C)cc(Oc2cc(Br)ncn2)cc1C]

Essentially following the procedures described for intermediate 1-2, using 4-methoxy-3,5-dimethyl-phenol (255 mg, 1.68 mmol) to afford, after purification by silica gel chromatography, eluting with a gradient of ethyl acetate:cyclohexane—0:100 to 20:80, the title compound as a white solid (500 mg, 96% yield). ¹H NMR (300 MHz, DMSO-d₆) 8.57 (s, 1H), 7.45 (s, 1H), 6.88 (s, 2H), 3.65 (s, 3H), 2.20 (s, 6H).

Example 35: 3-[6-(4-methoxy-3,5-dimethyl-phenoxy)pyrimidin-4-yl]-5,5-dimethyl-imidazolidine-2,4-dione

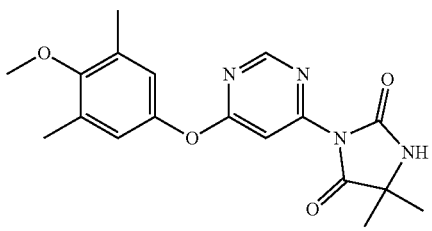

Essentially following the procedures described for example 1-1, using 4-bromo-6-(4-methoxy-3,5-dimethyl-phenoxy)pyrimidine (500 mg, 1.62 mmol) to afford, after purification by silica gel chromatography eluting with a gradient of ethyl acetate:cyclohexane—0:100 to 100:0, and a Sephadex exclusion chromatography, the title compound as a white solid (125 mg, 21% yield). ¹H NMR (300 MHz, CHCl₃-d) 8.83 (s, 1H), 7.07 (s, 1H), 6.80 (s, 2H), 5.88 (bs, 1H), 3.74 (s, 3H), 2.30 (s, 6H), 1.57 (s, 6H). ESIMS m/z [M+H]⁺=357.4.

Intermediate 1-36: 5-(6-bromopyrimidin-4-yl)oxy-2-methyl-phenol

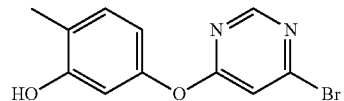 [SMILES: Cc1ccc(Oc2cc(Br)ncn2)cc1O]

To a solution of 4-bromo-6-(3-methoxy-4-methyl-phenoxy)pyrimidine, intermediate 1-2, (500 mg, 1.7 mmol) in DCM (15 mL) at −70° C., boron tribromide 1.0M in CH₂Cl₂ (1.7 mL, 1.7 mmol) was added. The mixture was allowed to warm to room temperature, stirred for 1 h, heated to 40° C. and stirred for 18 h. An extra amount of boron tribromide 1.0M in CH₂Cl₂ (1.5 mL) was added at 0° C. and the mixture was stirred 24 h at 40° C. The mixture was poured onto ice, made basic with NaOH (1N) and extracted with EtOAc (3×30 mL).

The combined organic extracts were dried over magnesium sulfate, filtered, and concentrated under reduced pressure. The residue was purified by silica gel chromatography eluting with a gradient of ethyl acetate:cyclohexane—0:100 to 60:40 to afford the title compounds as yellow oil (250 mg, 53% yield). ¹H NMR (300 MHz, CHCl₃-d) 8.53 (s, 1H), 7.14 (d, J=8.1 Hz, 1H), 6.55 (dd, J=8.1 and 2.3 Hz, 1H), 6.50 (d, J=2.3 Hz, 1H), 2.20 (s, 3H).

Intermediate 1-37: 4-bromo-6-(3-ethoxy-4-methyl-phenoxy)pyrimidine

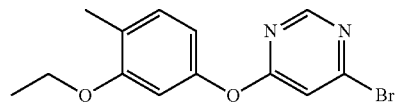 [SMILES: CCOc1cc(Oc2cc(Br)ncn2)ccc1C]

To a solution of 5-(6-bromopyrimidin-4-yl)oxy-2-methyl-phenol (125 mg, 0.44 mmol) and potassium carbonate (123 mg, 0.89 mmol) in DMF (3 mL), was added Iodoethane (139 mg, 0.89 mmol). The mixture was stirred at room temperature for 18 h and then diluted with water (100 mL), extracted with EtOAc (3×20 mL). The combined organic extracts were washed with NaCl (100 mL), dried over magnesium sulfate, filtered, and concentrated under reduced pressure to afford, after purification by silica gel chromatography eluting with a gradient of ethyl acetate:cyclohexane—0:100 to 50:50 to afford the title compounds as a colorless oil (120 mg, 88% yield). ¹H NMR (300 MHz, CHCl₃-d) 8.54 (d, J=0.7 Hz, 1H), 7.17 (d, J=8.0 Hz, 1H), 7.04 (d, J=0.7 Hz, 1H), 6.65-6.55 (m, 2H), 3.98 (q, J=7.0 Hz, 2H), 2.22 (s, 3H), 1.23 (t, J=7.0 Hz, 3H).

Example 36: 3-[6-(3-ethoxy-4-methyl-phenoxy)pyrimidin-4-yl]-5,5-dimethyl-imidazolidine-2,4-dione

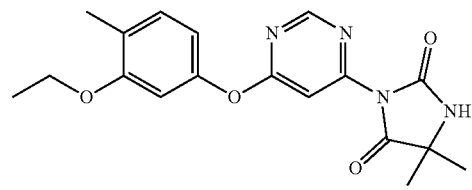 [SMILES: CCOc1cc(Oc2cc(N3C(=O)NC(C)(C)C3=O)ncn2)ccc1C]

Essentially following the procedures described for example 1-1, using 4-bromo-6-(3-ethoxy-4-methyl-phenoxy)pyrimidine (120 mg, 0.39 mmol) to afford, after purification by silica gel chromatography eluting with a gradient of ethyl acetate:cyclohexane—0:100 to 100:0, and a lyophilization using acetonitrile and water, the title compound as a white powder (60 mg, 42% yield). $^1$H NMR (300 MHz, DMSO-d$_6$) 8.76 (s, 1H), 8.73 (bs, 1H), 7.19 (d, J=8.2 Hz, 1H), 7.10 (s, 1H), 6.83 (d, J=2.2 Hz, 1H), 6.68 (dd, J=8.2 and 2.2 Hz, 1H), 3.99 (q, J=7.0 Hz, 2H), 2.13 (s, 3H), 1.37 (s, 6H), 1.30 (t, J=7.0 Hz, 3H). ESIMS m/z [M+H]$^+$=357.3.

Intermediate 1-38: 4-bromo-6-[3-(cyclopropyl-methoxy)-4-methyl-phenoxy]pyrimidine

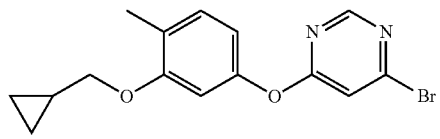 [SMILES: Cc1ccc(Oc2cc(Br)ncn2)cc1OCC1CC1]

Essentially following the procedures described for intermediate 1-28, using iodomethyl(cyclopropane) (160 mg, 0.89 mmol) to afford, after purification by silica gel chromatography eluting with a gradient of ethyl acetate:cyclohexane—0:100 to 50:50, the title compound as a colorless oil (80 mg, 54% yield). $^1$H NMR (300 MHz, CHCl$_3$-d) 8.54 (s, 1H), 7.17 (d, J=8.0 Hz, 1H), 7.04 (s, 1H), 6.61 (dd, J=8.0 and 2.2 Hz, 1H), 6.54 (d, J=2.2 Hz, 1H), 3.77 (d, J=6.7 Hz, 2H), 2.25 (s, 3H), 1.30-1.22 (m, 1H), 0.67-0.58 (m, 2H), 0.39-0.30 (m, 2H).

Example 37: 3-[6-[3-(cyclopropylmethoxy)-4-methyl-phenoxy]pyrimidin-4-yl]-5,5-dimethyl-imidazolidine-2,4-dione

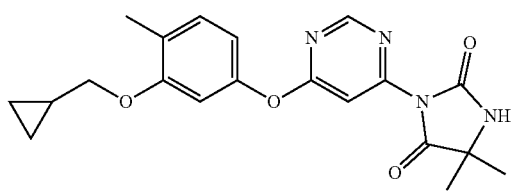 [SMILES: Cc1ccc(Oc2cc(N3C(=O)NC(C)(C)C3=O)ncn2)cc1OCC1CC1]

Essentially following the procedures described for example 1-1, using 4-bromo-6-[3-(cyclopropylmethoxy)-4-methyl-phenoxy]pyrimidine (80 mg, 0.24 mmol) to afford, after purification by silica gel chromatography eluting with a gradient of ethyl acetate:cyclohexane—0:100 to 100:0, a Sephadex exclusion chromatography and a lyophilization using acetonitrile and water, the title compound as a white powder (20 mg, 20% yield). $^1$H NMR (300 MHz, DMSO-d$_6$) 8.76 (s, 1H), 8.73 (bs, 1H), 7.19 (d, J=8.1 Hz, 1H), 7.10 (s, 1H), 6.81 (d, J=2.1 Hz, 1H), 6.68 (dd, J=8.1 and 2.1 Hz, 1H), 3.78 (d, J=6.8 Hz, 2H), 2.16 (s, 3H), 1.37 (s, 6H), 1.29-1.17 (m, 1H), 0.56-0.50 (m, 2H), 0.37-0.28 (m, 2H). ESIMS m/z [M+H]+=383.4.

Intermediate 1-39: 4-bromo-6-(3-isopropoxy-4-methyl-phenoxy)pyrimidine

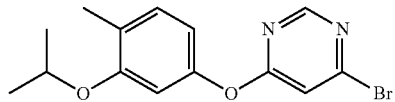 [SMILES: Cc1ccc(Oc2cc(Br)ncn2)cc1OC(C)C]

Essentially following the procedures described for intermediate 1-28, using 2-iodopropane (170 mg, 1.0 mmol) to afford, after purification by silica gel chromatography eluting with a gradient of ethyl acetate:cyclohexane—0:100 to 60:40, the title compound as a colorless oil (75 mg, 47% yield). $^1$H NMR (300 MHz, CHCl$_3$-d) 8.55 (d, J=0.7 Hz, 1H), 7.17 (d, J=8.2 Hz, 1H), 7.05 (d, J=0.7 Hz, 1H), 6.65-6.55 (m, 2H), 4.46 (sept, J=6.0 Hz, 1H), 2.20 (s, 3H), 1.33 (d, J=6.0 Hz, 6H).

Example 38: 3-[6-(3-isopropoxy-4-methyl-phenoxy)pyrimidin-4-yl]-5,5-dimethyl-imidazolidine-2,4-dione

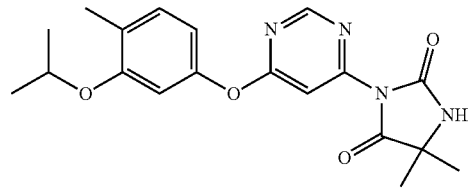 [SMILES: Cc1ccc(Oc2cc(N3C(=O)NC(C)(C)C3=O)ncn2)cc1OC(C)C]

Essentially following the procedures described for example 1-1, using 4-bromo-6-(3-isopropoxy-4-methyl-phenoxy)pyrimidine (75 mg, 0.23 mmol) to afford, after purification by silica gel chromatography eluting with a gradient of ethyl acetate:cyclohexane—0:100 to 100:0, a semi-preparative purification and a lyophilization using acetonitrile and water, the title compound as a white foam (24 mg, 27% yield). $^1$H NMR (300 MHz, DMSO-d$_6$) 8.76 (s, 1H), 8.73 (bs, 1H), 7.19 (d, J=8.1 Hz, 1H), 7.10 (s, 1H), 6.87 (d, J=2.1 Hz, 1H), 6.67 (dd, J=8.1 and 2.1 Hz, 1H), 4.46 (sept, J=6.0 Hz, 1H), 2.21 (s, 3H), 1.37 (s, 6H), 1.23 (d, J=6.0 Hz, 6H). ESIMS m/z [M+H]+=371.3.

Intermediate 1-40: 4-bromo-6-(3-isobutoxy-4-methyl-phenoxy)pyrimidine

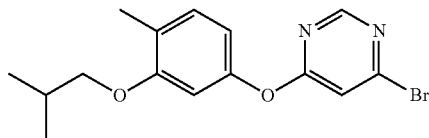 [SMILES: Cc1ccc(Oc2cc(Br)ncn2)cc1OCC(C)C]

Essentially following the procedures described for intermediate 1-28, using 1-iodo-2-methylpropane (185 mg, 1.0 mmol) to afford, after purification by silica gel chromatography eluting with a gradient of ethyl acetate:cyclohexane—0:100 to 80:20, the title compound as a colorless oil (62 mg, 35% yield). $^1$H NMR (300 MHz, CHCl$_3$-d) 8.55 (d, J=0.7 Hz, 1H), 7.17 (d, J=8.0 Hz, 1H), 7.05 (d, J=0.7 Hz, 1H), 6.60

(dd, J=8.0 and 2.0 Hz, 1H), 6.56 (d, J=2.0 Hz, 1H), 3.67 (d, J=6.4 Hz, 1H), 2.24 (s, 3H), 2.22-2.02 (m, 1H), 1.03 (d, J=6.4 Hz, 6H).

Example 39: 3-[6-(3-isobutoxy-4-methyl-phenoxy)pyrimidin-4-yl]-5,5-dimethyl-imidazolidine-2,4-dione

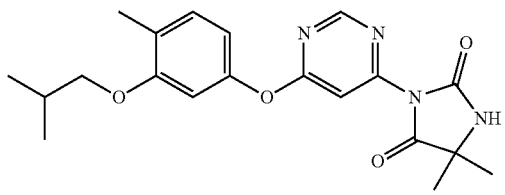 [SMILES: Cc1ccc(Oc2cc(N3C(=O)NC(C)(C)C3=O)ncn2)cc1OCC(C)C]

Essentially following the procedures described for example 1-1, using 4-bromo-6-(3-isobutoxy-4-methyl-phenoxy)pyrimidine (60 mg, 0.18 mmol) to afford, after purification by silica gel chromatography eluting with a gradient of ethyl acetate:cyclohexane—0:100 to 100:0, and a lyophilization using acetonitrile and water, the title compound as a white foam (18 mg, 25% yield). $^1$H NMR (300 MHz, DMSO-$d_6$) 8.76 (s, 1H), 8.73 (bs, 1H), 7.19 (d, J=8.1 Hz, 1H), 7.10 (s, 1H), 6.83 (d, J=2.2 Hz, 1H), 6.68 (dd, J=8.1 and 2.2 Hz, 1H), 3.70 (d, J=6.4 Hz, 1H), 2.15 (s, 3H), 2.10-1.94 (m, 1H), 1.37 (s, 6H), 0.96 (d, J=6.4 Hz, 6H). ESIMS m/z [M+H]+=385.3.

Intermediate 1-41:
2-(2,6-dimethoxyphenyl)propan-2-ol

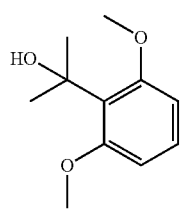

To a solution of 1-(2,6-dimethoxyphenyl)ethanone (5.0 g, 27.75 mmol) in THF (50 mL) was added methylmagnesium bromide 3M in THF (37. mL, 111.0 mmol) dropwise at 0° C. The reaction mixture was stirred for 16 h at room temperature. The mixture was quenched at 0° C. with a saturated aqueous solution of NH$_4$Cl and extracted with AcOEt (3×50 mL). The organic layers were washed with water and brine, dried over Na$_2$SO$_4$, filtered, and concentrated. The residue was purified by silica gel chromatography eluting with a gradient of ethyl acetate:cyclohexane—0:100 to 80:20 to afford the title compound as a yellow oil (4.4 g, 76% yield). $^1$H NMR (300 MHz, DMSO-$d_6$) 7.15 (t, J=8.4 Hz, 1H), 6.68 (d, J=8.4 Hz, 2H), 5.42 (s, 1H), 3.76 (s, 6H), 1.50 (s, 6H).

Intermediate 1-42:
2-isopropyl-1,3-dimethoxy-benzene

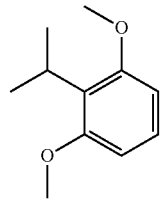

A mixture of 2-(2,6-dimethoxyphenyl)propan-2-ol (4.4 g, 21.17 mmol), Pd on carbon (50 mg, 0.47 mmol), and concentrated sulfuric acid (10 drops) in ethyl acetate (60 mL) was shaken in a Parr hydrogenator for 18 h under 3 bars of hydrogen. Then the reaction mixture was filtered through Celite, and the solvent was evaporated. The residue was dissolved in ether and washed with a saturated aqueous solution of Na$_2$CO$_3$. The ether layer was dried over MgSO$_4$, filtered and concentrated in vacuo. The residue was purified by silica gel chromatography eluting with a gradient of ethyl acetate:cyclohexane—0:100 to 100:0 to afford the title compound as a colorless oil (3.6 g, 95% yield). $^1$H NMR (300 MHz, DMSO-$d_6$) 7.07 (t, J=8.4 Hz, 1H), 6.57 (d, J=8.4 Hz, 2H), 3.72 (s, 6H), 3.49 (sept, J=7.1 Hz, 1H), 1.18 (d, J=7.1 Hz, 6H).

Intermediate 1-43: 2-isopropyl-3-methoxy-phenol and 2-isopropylbenzene-1,3-diol

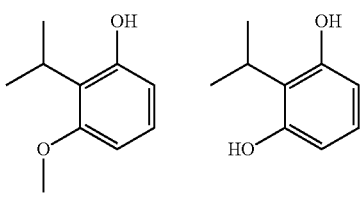

To a solution of 2-isopropyl-1,3-dimethoxy-benzene (3.41 g, 18.9 mmol) in DCM (50 mL) at −78° C. was added Boron tribromide 1.0M in DCM (14.19 mL, 14.19 mmol). The solution was stirred at −78° C. for 5 h, warmed to room temperature and stirred for an additional 18 h. The reaction mixture was cooled to 0° C., quenched with a saturated aqueous solution of NaHCO$_3$, the organic layer was separated, dried over MgSO$_4$, and concentrated. The residue was purified by silica gel chromatography eluting with a gradient of ethyl acetate:cyclohexane—0:100 to 100:0 to afford the first eluting product, 2-isopropyl-3-methoxy-phenol (1.79 g, 37% yield) as a beige solid. $^1$H NMR (300 MHz, CHCl$_3$-d) 6.99 (t, J=8.2 Hz, 1H), 6.47 (d, J=8.2 Hz, 1H), 6.37 (d, J=8.2 Hz, 1H), 4.69 (bs, 1H), 3.79 (s, 3H), 3.50 (sept, J=7.1 Hz, 1H), 1.32 (d, J=7.1 Hz, 6H). The second eluting product, 2-isopropylbenzene-1,3-diol (1.09 g, 37% yield) was obtained as a yellow solid. $^1$H NMR (300 MHz, CHCl$_3$-d) 6.87 (t, J=8.0 Hz, 1H), 6.32 (d, J=8.0 Hz, 2H), 4.82 (bs, 2H), 3.46 (sept, J=7.1 Hz, 1H), 1.36 (d, J=7.1 Hz, 6H).

Intermediate 1-44: 4-bromo-6-(2-isopropyl-3-methoxy-phenoxy)pyrimidine

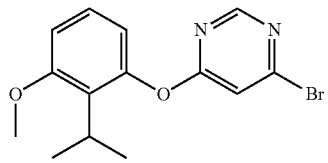 [SMILES: COc1cccc(Oc2cc(Br)ncn2)c1C(C)C]

Essentially following the procedures described for intermediate 1-2, using 2-isopropyl-3-methoxy-phenol (280 mg, 1.7 mmol) to afford, after purification by silica gel chromatography eluting with a gradient of ethyl acetate:cyclohexane—0:100 to 70:30, the title compound as a colorless oil (550 mg, 91% yield). $^1$H NMR (300 MHz, DMSO-$d_6$) 8.57 (d, J=0.7 Hz, 1H), 7.50 (d, J=0.7 Hz, 1H), 7.20 (t, J=8.2 Hz, 1H), 6.90 (d, J=8.2 Hz, 1H), 6.68 (d, J=8.2 Hz, 1H), 3.80 (s, 3H), 3.17 (sept, J=7.0 Hz, 1H), 1.12 (d, J=7.0 Hz, 6H).

Example 40: 3-[6-(2-isopropyl-3-methoxy-phenoxy)pyrimidin-4-yl]-5,5-dimethyl-imidazolidine-2,4-dione

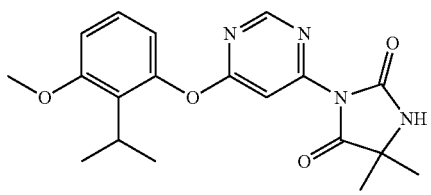

Essentially following the procedures described for example 1-1, using 4-bromo-6-(2-isopropyl-3-methoxy-phenoxy)pyrimidine (550 mg, 1.7 mmol) to afford, after purification by silica gel chromatography eluting with a gradient of ethyl acetate:cyclohexane—0:100 to 100:0, a Sephadex exclusion chromatography and a lyophilization using acetonitrile and water, the title compound as a white foam (350 mg, 55% yield). $^1$H NMR (300 MHz, DMSO-$d_6$) 8.76 (d, J=0.8 Hz, 1H), 8.74 (s, 1H), 7.22 (t, J=8.2 Hz, 1H), 7.12 (d, J=0.8 Hz, 1H), 6.92 (d, J=8.2 Hz, 1H), 6.70 (d, J=8.2 Hz, 1H), 3.81 (s, 3H), 3.19 (sept, J=7.0 Hz, 1H), 1.38 (s, 6H), 1.14 (d, J=7.0 Hz, 6H). ESIMS m/z [M+H]+=371.4.

Intermediate 1-45: 4-chloro-3-methoxy-phenol

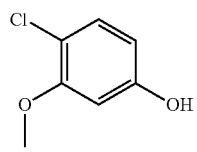

To a stirred solution of 4-chlororesorcinol (4.0 g, 27.67 mmol) in acetone (100 mL) was added potassium carbonate (7.40 g, 53.50 mmol). The mixture was stirred 30 minutes at room temperature and iodomethane (1.72 mL, 27.67 mmol) was added dropwise. The resulting solution was stirred at reflux for 18 h. The mixture was concentrated in vacuo before, hydrolyzed with a saturated aqueous solution of NH$_4$Cl, extracted using ethyl acetate, the organics were washed with brine, dried over MgSO$_4$ and concentrated in vacuo before purification by silica gel flash chromatography eluting with a gradient of cyclohexane:ethyl acetate-100:0 to 80:20 to give the title compound as a beige solid (2.0 g, 46% yield). ESIMS m/z [M+H]+=159.0.

Intermediate 1-46: 4-bromo-6-(4-chloro-3-methoxy-phenoxy)pyrimidine

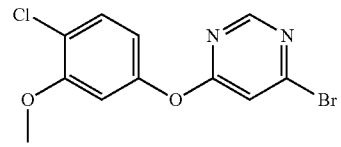 [SMILES: COc1cc(Oc2cc(Br)ncn2)ccc1Cl]

Essentially following the procedures described for intermediate 1-2, using 4-chloro-3-methoxy-phenol (410 mg, 2.59 mmol) to afford, after purification by silica gel chromatography eluting with a gradient of ethyl acetate:cyclohexane—0:100 to 50:50, the title compound as a colorless gum (760 mg, 93% yield). $^1$H NMR (300 MHz, DMSO-$d_6$) 8.60 (d, J=0.7 Hz, 1H), 7.54 (d, J=0.7 Hz, 1H), 7.48 (d, J=8.6 Hz, 1H), 7.11 (d, J=2.6 Hz, 1H), 6.83 (dd, J=2.6 and 8.6 Hz, 1H), 3.81 (s, 3H).

Example 41: 3-[6-(4-chloro-3-methoxy-phenoxy)pyrimidin-4-yl]-5,5-dimethyl-imidazolidine-2,4-dione

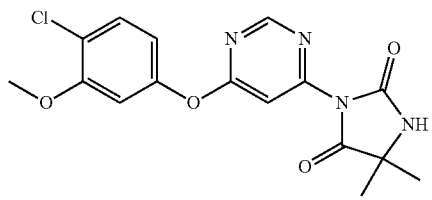

Essentially following the procedures described for example 1-1, using 4-bromo-6-(4-chloro-3-methoxy-phenoxy)pyrimidine (335 mg, 1.06 mmol) to afford, after purification by silica gel chromatography eluting with a gradient of ethyl acetate:cyclohexane—0:100 to 75:25 and a lyophilization using acetonitrile and water, the title compound as a white foam (127 mg, 33% yield). $^1$H NMR (300 MHz, DMSO-$d_6$) 8.78 (d, J=0.9 Hz, 1H), 8.75 (bs, 1H), 7.50 (d, J=8.6 Hz, 1H), 7.20 (d, J=0.9 Hz, 1H), 7.15 (d, J=2.6 Hz, 1H), 6.87 (dd, J=2.6 and 8.6 Hz, 1H), 3.88 (s, 3H), 1.38 (s, 6H). ESIMS m/z [M+H]+=363.3.

Intermediate 1-47: 4-bromo-6-[3-methoxy-4-(trifluoromethyl)phenoxy]pyrimidine

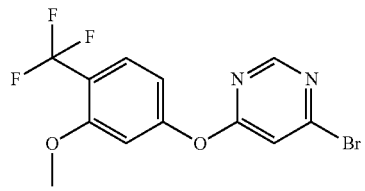 [SMILES: COc1cc(Oc2cc(Br)ncn2)ccc1C(F)(F)F]

Essentially following the procedures described for intermediate 1-2, using 3-methoxy-4-(trifluoromethyl)phenol (300 mg, 1.56 mmol) to afford, after purification by silica gel chromatography eluting with a gradient of ethyl acetate:cyclohexane—0:100 to 40:60, the title compound as a white solid (445 mg, 81% yield). ESIMS m/z [M+H]+=348.9-350.9.

Example 42: 3-[6-[3-methoxy-4-(trifluoromethyl)phenoxy]pyrimidin-4-yl]-5,5-dimethyl-imidazolidine-2,4-dione

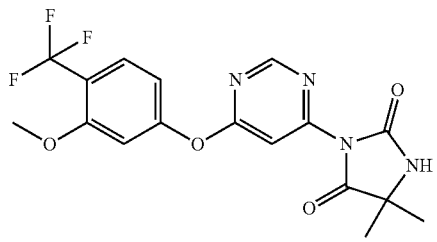

Essentially following the procedures described for example 1-1, using 4-bromo-6-[3-methoxy-4-(trifluoromethyl)phenoxy]pyrimidine (445 mg, 1.27 mmol) to afford, after purification by silica gel chromatography eluting with a gradient of ethyl acetate:cyclohexane—0:100 to 100:0, the title compound as a white solid (300 mg, 57% yield). $^1$H NMR (300 MHz, DMSO-$d_6$) 8.80 (d, J=0.9 Hz, 1H), 8.77 (bs, 1H), 7.70 (d, J=8.6 Hz, 1H), 7.29 (d, J=0.9 Hz, 1H), 7.26 (d, J=1.7 Hz, 1H), 7.00 (dd, J=1.8 and 8.6 Hz, 1H), 3.86 (s, 3H), 1.39 (s, 6H). ESIMS m/z [M+H]+=397.3.

Intermediate 1-48: 4-bromo-6-[3-fluoro-4-(trifluoromethyl)phenoxy]pyrimidine

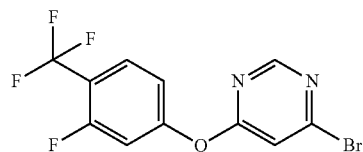 [SMILES: Fc1cc(Oc2cc(Br)ncn2)ccc1C(F)(F)F]

Essentially following the procedures described for intermediate 1-2, using 3-fluoro-4-(trifluoromethyl)phenol (300 mg, 1.67 mmol) to afford, after purification by silica gel chromatography eluting with a gradient of ethyl acetate:cyclohexane—0:100 to 60:40, the title compound as a colorless oil (490 mg, 87% yield). ESIMS m/z [M+H]+=337.1-339.1.

Example 43: 3-[6-[3-fluoro-4-(trifluoromethyl)phenoxy]pyrimidin-4-yl]-5,5-dimethyl-imidazolidine-2,4-dione

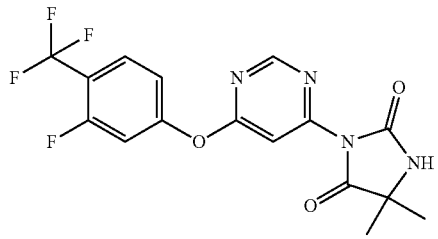 [SMILES: CC1(C)NC(=O)N(c2cc(Oc3ccc(C(F)(F)F)c(F)c3)ncn2)C1=O]

Essentially following the procedures described for example 1-1, using 4-bromo-6-[3-fluoro-4-(trifluoromethyl)phenoxy]pyrimidine (490 mg, 1.45 mmol) to afford, after purification by silica gel chromatography eluting with a gradient of ethyl acetate:cyclohexane—0:100 to 100:0 followed by a filtration in diethyl ether, the title compound as a white solid (105 mg, 18% yield). $^1$H NMR (300 MHz, DMSO-$d_6$) 8.81 (s, 1H), 8.79 (bs, 1H), 7.90 (app. t, J=8.6 Hz, 1H), 7.69 (dd, J=1.8 and 11.7 Hz, 1H), 7.38 (d, J=9.9 Hz, 1H), 7.35 (s, 1H), 1.40 (s, 6H). ESIMS m/z [M+H]+=385.3.

Intermediate 1-49: 4-(hydroxymethyl)-3-(trifluoromethoxy)phenol

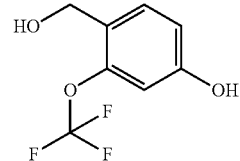

Essentially following the procedures described for intermediate 1-1, using 4-hydroxy-2-(trifluoromethyl)benzaldehyde (500 mg, 2.43 mmol) to afford, after purification by silica gel flash chromatography eluting with a gradient of cyclohexane:ethyl acetate-100:0 to 50:50, the title compound as a white powder (475 mg, 94% yield). $^1$H NMR (300 MHz, CHCl$_3$-d) 7.37 (d, J=9.0 Hz, 1H), 6.80-6.74 (m, 2H), 5.01 (bs, 1H), 4.68 (s, 2H). ESIMS m/z [M–H$_2$O]+= 190.9.

Intermediate 1-50: [4-(6-bromopyrimidin-4-yl)oxy-2-(trifluoromethoxy)phenyl]methanol

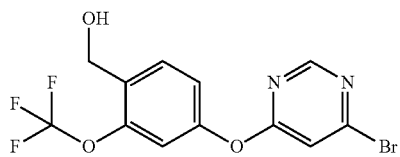 [SMILES: OCc1ccc(Oc2cc(Br)ncn2)cc1OC(F)(F)F]

Essentially following the procedures described or intermediate 1-2, using 4-(hydroxymethyl)-3-(trifluoromethoxy)phenol (200 mg, 0.96 mmol) to afford the title compound as a colorless oil and pure enough to be used as such (310 mg, 88% yield). $^1$H NMR (300 MHz, DMSO-$d_6$) 8.60 (d, J=0.7

Hz, 1H), 7.70-7.60 (m, 2H), 7.36-7.28 (m, 2H), 5.43 (t, J=5.8 Hz, 1H), 4.57 (d, J=5.8 Hz, 2H). ESIMS m/z [M+H]+=364.9-366.9.

Intermediate 1-51: 3-[6-[4-(hydroxymethyl)-3-(trifluoromethoxy)phenoxy]pyrimidin-4-yl]-5,5-dimethyl-imidazolidine-2,4-dione

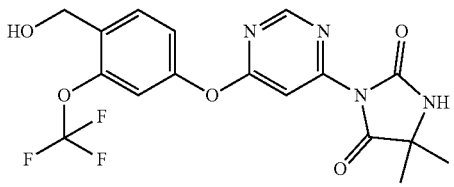 [SMILES: CC1(C)NC(=O)N(c2cc(Oc3ccc(CO)c(OC(F)(F)F)c3)ncn2)C1=O]

Essentially following the procedures described for example 1-1, using [4-(6-bromopyrimidin-4-yl)oxy-2-(trifluoromethoxy)phenyl]methanol (310 mg, 0.85 mmol) to afford, after purification by silica gel chromatography eluting with a gradient of ethyl acetate:cyclohexane—0:100 to 100:0 and then a gradient of methanol:ethyl acetate-0:100 to 10:90, the title compound as a white powder (150 mg, 43% yield). $^1$H NMR (300 MHz, DMSO-d$_6$) 8.78 (s, 1H), 7.64 (d, J=8.5 Hz, 1H), 7.20-7.08 (m, 3H), 6.38 (bs, 1H), 4.79 (s, 2H), 2.20 (bs, 1H), 1.57 (s, 6H). ESIMS m/z [M+H]+=413.3.

Intermediate 1-52: 3-[6-[4-(chloromethyl)-3-(trifluoromethoxy)phenoxy]pyrimidin-4-yl]-5,5-dimethyl-imidazolidine-2,4-dione

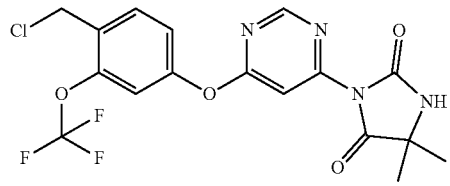 [SMILES: CC1(C)NC(=O)N(c2cc(Oc3ccc(CCl)c(OC(F)(F)F)c3)ncn2)C1=O]

A solution of 3-[6-[4-(hydroxymethyl)-3-(trifluoromethoxy)phenoxy]pyrimidin-4-yl]-5,5-dimethyl-imidazolidine-2,4-dione (150 mg, 0.36 mmol) in SOCl$_2$ (2 mL) was stirred at room temperature with 2 drops of DMF for 4 h. The solvents were removed under reduced pressure, the resulting mixture was diluted with water (50 mL), extracted with ethyl acetate (3×20 mL), the combined organic extracts were dried over magnesium sulfate, filtered, and concentrated under reduced pressure to afford, after purification by silica gel chromatography eluting with a gradient of ethyl acetate:cyclohexane—0:100 to 100:0 and then a gradient of methanol:ethyl acetate-0:100 to 10:90, the title compound as a white solid (90 mg, 55% yield). $^1$H NMR (300 MHz, DMSO-d$_6$) 8.78 (s, 1H), 7.75 (d, J=8.6 Hz, 1H), 7.47 (bs, 1H), 7.37 (dd, J=2.3 and 8.4 Hz, 1H), 7.30 (s, 1H), 4.81 (s, 2H), 1.40 (s, 6H). ESIMS m/z [M+H]+=430.9-432.9.

Example 44: 3-[6-[4-methyl-3-(trifluoromethoxy)phenoxy]pyrimidin-4-yl]-5,5-dimethyl-imidazolidine-2,4-dione

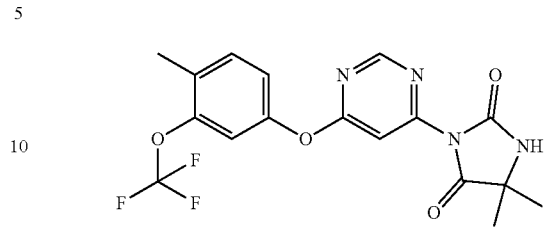

Essentially following the procedures described for example 1-1, using 3-[6-[4-(chloromethyl)-3-(trifluoromethoxy)phenoxy]pyrimidin-4-yl]-5,5-dimethyl-imidazolidine-2,4-dione (70 mg, 0.16 mmol) in ethanol (20 mL) to afford, after purification by silica gel chromatography eluting with a gradient of ethyl acetate:cyclohexane—0:100 to 100:0, the title compound as a white solid (49 mg, 75% yield). $^1$H NMR (300 MHz, DMSO-d$_6$) 8.77 (s, 1H), 7.48 (d, J=8.4 Hz, 1H), 7.35 (bs, 1H), 7.28-7.20 (m, 2H), 2.28 (s, 3H), 1.39 (s, 6H). ESIMS m/z [M+H]+=397.3.

Intermediate 1-53: (2,2-difluoro-1,3-benzodioxol-5-yl)boronic Acid

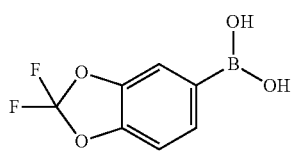 [SMILES: OB(O)c1ccc2c(c1)OC(F)(F)O2]

n-Butyl lithium 2.5M in hexane (11.36 mL, 28.40 mmol) was added dropwise to a stirred solution of 5-bromo-2,2-difluoro-1,3-benzodioxole (5.0 g, 21.10 mmol) and triisopropyl borate (6.3 g, 33.50 mmol) in THF (60 mL) at −78° C. under nitrogen. The resulting solution was stirred at −78° C. for 1 h and at room temperature for 3 h. The mixture was hydrolyzed with a saturated aqueous solution of ammonium chloride (20 mL), stirred 30 minutes, an aqueous solution of 3N HCl (20 mL) was then added and the mixture was extracted with Et$_2$O. The organics were washed with brine, dried over MgSO$_4$ and concentrated in vacuo to afford the title compound as a yellow oil which was used directly for next step.

Intermediate 1-54: 2,2-difluoro-1,3-benzodioxol-5-ol

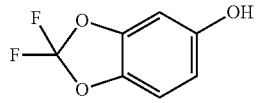 [SMILES: Oc1ccc2c(c1)OC(F)(F)O2]

Hydrogen peroxide 30% in water (40 mL) was added dropwise to a stirred solution of crude intermediate 1-10 in THF (100 mL) at room temperature. The resulting solution was stirred 20 h and carefully hydrolyzed with a saturated aqueous solution of Na$_2$S$_2$O$_3$ (50 mL). The mixture was extracted with ethylacetate (3×50 mL), the organics were washed with brine, dried over MgSO₄ and concentrated in vacuo to afford, after purification by silica gel flash chromatography eluting with a gradient of cyclohexane:ethyl acetate—100:0 to 50:50, the title compound as a yellow oil (3.2 g, 80% yield). $^1$H NMR (300 MHz, CHCl$_3$-d) 9.77 (s, 1H), 7.14 (d, J=8.8 Hz, 1H), 6.76 (d, J=2.4 Hz, 1H), 6.51 (dd, J=2.4 and 8.8 Hz, 1H).

Intermediate 1-55: 4-bromo-6-[(2,2-difluoro-1,3-benzodioxol-5-yl)oxy]pyrimidine

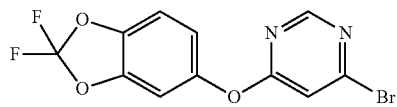 [SMILES: FC1(F)Oc2ccc(Oc3cc(Br)ncn3)cc2O1]

Essentially following the procedures described for intermediate 1-2, using 2,2-difluoro-1,3-benzodioxol-5-ol (300 mg, 1.72 mmol) to afford, after purification by silica gel flash chromatography eluting with a gradient of cyclohexane:ethyl acetate-100:0 to 70:30, the title compound as a white solid (560 mg, 96% yield). ESIMS m/z [M+H]⁺= 331.3-333.1.

Example 45: 3-[6-[(2,2-difluoro-1,3-benzodioxol-5-yl)oxy]pyrimidin-4-yl]-5,5-dimethyl-imidazolidine-2,4-dione

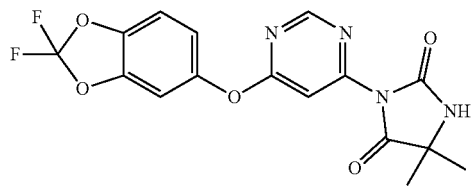 [SMILES: CC1(C)NC(=O)N(c2cc(Oc3ccc4c(c3)OC(F)(F)O4)ncn2)C1=O]

Essentially following the procedures described for example 1-1, using 4-bromo-6-[(2,2-difluoro-1,3-benzodioxol-5-yl)oxy]pyrimidine (200 mg, 0.60 mmol) to afford, after purification by silica gel chromatography eluting with a gradient of ethyl acetate:cyclohexane—0:100 to 100:0 and a semi-preparative purification, the title compound as a white solid (28 mg, 12% yield). $^1$H NMR (300 MHz, DMSO-d₆) 8.78 (d, J=0.8 Hz, 1H), 8.76 (bs, 1H), 7.57 (d, J=2.4 Hz, 1H), 7.50 (d, J=8.7 Hz, 1H), 7.25 (d, J=0.8 Hz, 1H), 7.13 (dd, J=2.4 and 8.7 Hz, 1H), 1.39 (s, 6H). ESIMS m/z [M+H]⁺=379.2.

Example 46: 3-[6-[(2,2-difluoro-1,3-benzodioxol-5-yl)oxy]pyrimidin-4-yl]-1,3-diazaspiro[4.5]decane-2,4-dione

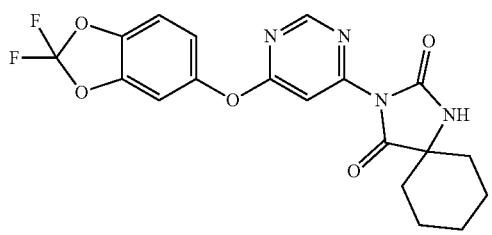 [SMILES: O=C1NC2(CCCCC2)C(=O)N1c1cc(Oc2ccc3c(c2)OC(F)(F)O3)ncn1]

Essentially following the procedures described for example 1-1, using 4-bromo-6-[(2,2-difluoro-1,3-benzodioxol-5-yl)oxy]pyrimidine (160 mg, 0.48 mmol) and 1,3-diazaspiro[4.5]decane-2,4-dione (98 mg, 0.58 mmol) to afford, after purification by silica gel chromatography eluting with a gradient of ethyl acetate:cyclohexane—0:100 to 100:0 and a lyophilization using acetonitrile and water, the title compound as a white foam (39 mg, 18% yield). $^1$H NMR (300 MHz, DMSO-d₆) 9.16 (bs, 1H), 8.77 (d, J=0.9 Hz, 1H), 7.56 (d, J=2.4 Hz, 1H), 7.50 (d, J=8.7 Hz, 1H), 7.24 (d, J=0.8 Hz, 1H), 7.13 (dd, J=2.4 and 8.7 Hz, 1H), 1.78-1.51 (m, 9H), 1.39-1.28 (m, 1H). ESIMS m/z [M+H]⁺=419.2.

Intermediate 1-56: 4-methylbenzene-1,3-diol

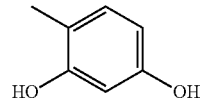

To a solution of 2,4-dihydroxy benzaldehyde (5.0 g, 36.2 mmol) and sodium cyanoborohydride (7.2 g, 114.58 mmol) in tetrahydrofuran (200 mL), an aqueous 1M HCl solution (110 mL, 110 mmol) was added dropwise. The reaction mixture was stirred at 20° C. for 18 hours. The reaction mixture was quenched with water (300 mL) and the organics were extracted with diethyl ether (3×100 mL). The organic phase was dried over magnesium sulfate, filtered, and the solvent was evaporated in vacuo to afford the title compound as a white solid (4.5 g, 100% yield). $^1$H NMR (MeOH-d₄) 6.81 (d, J=8.0 Hz, 1H), 6.25 (dd, J=3.0 and 6.7 Hz, 1H), 6.17 (dd, J=2.4 and 8.0 Hz, 1H), 2.05 (s, 3H).

Intermediate 1-57: 2,4-bis(methoxymethoxy)-1-methyl-benzene

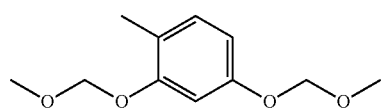

To a solution of 4-methylbenzene-1,4-diol (4.5, 36.2 mmol) in dry dimethylformamide (30 mL) at 0° C., sodium hydride (60% dispersion in oil, 4.34 g, 108.6 mmol) was added portionwise and the reaction mixture was stirred at 0° C. for 15 minutes. Chloromethyl methyl ether (8.25 mL, 108.6 mmol) was quickly added and the reaction mixture was stirred at 0° C. for 1 hour, while the temperature was allowed to reach room temperature. The reaction was quenched with brine (40 mL) and the organics were extracted with ethyl acetate (3×100 mL). The organic layer was washed with brine (50 mL) and water (40 mL). The organic layer was dried over magnesium sulfate, filtered and the solvent was evaporated in vacuo. The residue was purified by silica gel chromatography eluting with a gradient of ethyl acetate:cyclohexane—0:100 to 10:90, to afford the title compound as a colorless oil (4.0 g, 53% yield). [M+H]⁺ 213.0

Intermediate 1-58: ethyl 2-[2,6-bis(methoxymethoxy)-3-methyl-phenyl]-2-oxo-acetate

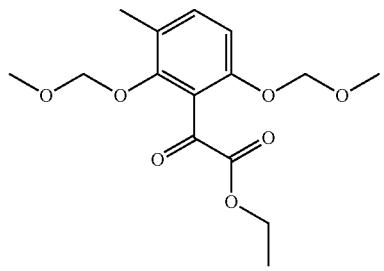

To a solution of 2,4-bis(methoxymethoxy)-1-methyl-benzene (5.5 g, 25.9 mmol) in dry THF (50 mL) at 20° C., n-butyllithium 2.5 M in hexanes (12.4 ml, 31.1 mmol) was added dropwise and the reaction mixture was stirred at room temperature for 30 minutes. The mixture was cooled to −78° C. and it was added via cannulation to a solution of ethyl chlorooxoacetate (4.35 ml, 38.8 mmol) in THF (10 mL) at −78° C. After addition, the reaction mixture was stirred at −78° C. for 2 hours. The reaction was quenched with water (50 mL) and diluted in brine (50 mL). The organics were extracted with diethyl ether (3×30 mL). The combined organic phases were dried over magnesium sulfate, filtered and the solvent was evaporated in vacuo. The residue was purified by silica gel chromatography eluting with a gradient of ethyl acetate:cyclohexane—0:100 to 50:50, to afford the title compound as yellow oil (5.6 g, 70% yield). [M+Na]$^+$ 335.0

Intermediate 1-59: ethyl 2-[2,6-bis(methoxymethoxy)-3-methyl-phenyl]prop-2-enoate

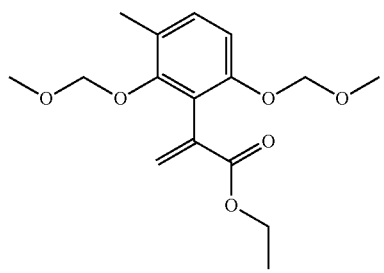

To a solution of ethyl 2-[2,6-bis(methoxymethoxy)-3-methyl-phenyl]-2-oxo-acetate (4.8 g, 15.4 mmol) in THF (50 mL), triphenylmethylphosphonium bromide (6.6 g, 18.4 mmol) was added. The reaction mixture was cooled to 0° C. and potassium tert-butoxide (2.1 g, 18.5 mmol) in solution in THF (100 mL) was added dropwise. The reaction mixture was stirred at 0° C. for 30 minutes and at room temperature for 18 hours. The reaction mixture was then hydrolyzed in water (150 mL) and the organics were extracted with diethyl ether (2×100 mL). The combined organic phases were dried over magnesium sulfate, filtered and the solvent was evaporated in vacuo. The residue was purified by silica gel chromatography eluting with a gradient of ethyl acetate:cyclohexane—0:100 to 30:70, to afford the title compound as colorless oil (3.0 g, 62% yield). [M+Na]$^+$333.0

Intermediate 1-60: ethyl 1-[2,6-bis(methoxymethoxy)-3-methyl-phenyl]cyclopropanecarboxylate

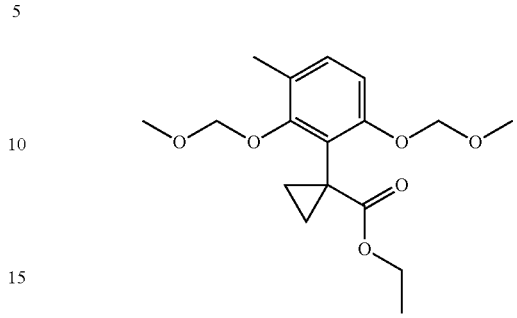

To a solution of trimethylsulfoxonium iodide (4.1 g, 18.6 mmol) in DMSO (15 mL), NaH 60% dispersion in oil (660 mg, 16.5 mmol) was added portionwise and the reaction mixture was stirred at 20° C. for 1 hour. Ethyl 2-[2,6-bis(methoxymethoxy)-3-methyl-phenyl]prop-2-enoate (3.2 g, 10.3 mmol) in solution in DMSO (5 mL) was then added and the reaction mixture was stirred at room temperature for 3 hours. The reaction mixture was quenched with aqueous saturated ammonium chloride solution (50 mL), diluted in water (150 mL) and the organics were extracted with ethyl acetate (2×100 mL). The organic layer was washed with water, dried over magnesium sulfate, filtered and the solvent was evaporated in vacuo. The residue was purified by silica gel chromatography eluting with a gradient of ethyl acetate:cyclohexane—0:100 to 20:80, to afford the title compound as colorless oil (2.5 g, 74% yield). [M+Na]$^+$347.0

Intermediate 1-61: 2-[1-(hydroxymethyl)cyclopropyl]-3-(methoxymethoxy)-6-methyl-phenol

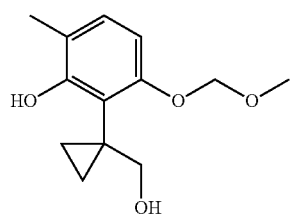

Ethyl 1-[2,6-bis(methoxymethoxy)-3-methyl-phenyl]cyclopropanecarboxylate (1.2 g, 3.6 mmol) was dissolved in ethanol (35 mL). An aqueous 6M hydrochloric acid solution (1.5 mL, 8.9 mmol) was added and the mixture was heated up to 50° C. for 18 hours. The solvent was carefully evaporated in vacuo. The dry residue was dissolved in dry tetrahydrofuran (35 mL). The solution was cooled to 0° C. and sodium hydride (60% dispersion in oil, 298 mg, 7.5 mmol) was added protionwise. The mixture was stirred at 0° C. for 45 minutes then chloromethyl methyl ether (324 μL, 4.3 mmol) was added at 0° C. The reaction mixture was stirred at 0° C. for 2 hours and was quenched with water (30 mL). A solution of aqueous M hydrochloric acid was added until pH=1. The organics were extracted with ethyl acetate (2×25 mL) and the combined organic phases were dried over magnesium sulfate. After filtration, the solvent was evaporated in vacuo. The residue was solubilized in dry tetrahydrofuran (35 mL) and a 1M lithium aluminum hydride in tetrahydrofuran (4.6 mL, 4.6 mmol) was slowly added at room temperature. The mixture was heated up to 50° C. under stirring for 3 hours. The reaction mixture was quenched with water at 0° C. An aqueous 1M hydrochloric acid solution was added until acid pH. The organics were extracted with diethyl ether (3×50 mL) and the combined organic layers were dried over magnesium sulfate, filtered and the solvent was evaporated in vacuo. The residue was purified by silica gel chromatography eluting with a gradient of ethyl acetate:cyclohexane—0:100 to 30:70, to afford the title compound as colorless oil (465 mg, 55% yield). [M+H]$^+$ 238.9

Intermediate 1-62: 4-(methoxymethoxy)-7-methyl-spiro[2H-benzofuran-3,1'-cyclopropane]

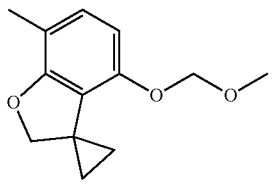

Triphenylphosphine (1.1 g, 4.2 mmol) was added to a solution of 2-[1-(hydroxymethyl)cyclopropyl]-3-(methoxymethoxy)-6-methyl-phenol (844 mg, 3.5 mmol) in solution in dry tetrahydrofuran (50 mL). After complete dissolution of triphenylphosphine, diisopropyl azodicarboxylate (764 µL, 3.8 mmol) was added dropwise and the reaction mixture was stirred at room temperature for 1 hour. The reaction mixture was concentrated in vacuo and the residue was purified by silica gel chromatography eluting with a gradient of ethyl acetate:cyclohexane—0:100 to 20:80, to afford the title compound as pale yellow oil (545 mg, 70% yield). [M+H]$^+$ 220.9

Intermediate 1-63: 7-methylspiro[2H-benzofuran-3,1'-cyclopropane]-4-ol

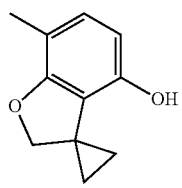

An aqueous 6N hydrochloric acid solution (1.4 mL, 8.7 mmol) was added to a solution of 4-(methoxymethoxy)-7-methyl-spiro[2H-benzofuran-3,1'-cyclopropane] (545 mg, 2.5 mmol) in ethanol (30 mL) and the reaction mixture was heated up to 50° C. under stirring for 18 hours. The solvent was evaporated in vacuo to afford the title compound as a crude (433 mg, 99% yield) which was used directly. $^1$H NMR (DMSO-d$_6$) 8.99 (s, 1H), 6.60 (d, J=8.1 Hz, 1H), 6.12 (d, J=8.1 Hz, 1H), 4.32 (s, 2H), 1.98 (s, 3H), 1.38 (dd, J=3.9 and 6.4 Hz, 2H), 0.76 (dd, J=3.8 and 6.2 Hz, 2H).

Intermediate 1-64: 4-bromo-6-(7-methylspiro[2H-benzofuran-3,1'-cyclopropane]-4-yl)oxy-pyrimidine

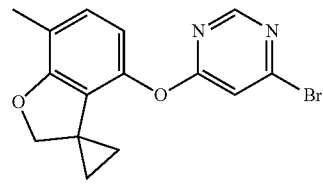 [SMILES: Cc1ccc(Oc2cc(Br)ncn2)c2c1OCC21CC1]

Essentially following the procedures described for intermediate 1-2, using 7-methylspiro[2H-benzofuran-3,1'-cyclopropane]-4-ol (200 mg, 1.14 mmol) to afford, after purification by silica gel chromatography eluting with a gradient of ethyl acetate:cyclohexane—0:100 to 20:80, the title compound as a white solid (250 mg, 66% yield). ESIMS m/z [M+H]+=333.5-335.5.

Example 47: 5,5-dimethyl-3-[6-(7-methylspiro[2H-benzofuran-3,1'-cyclopropane]-4-yl)oxypyrimidin-4-yl]imidazolidine-2,4-dione

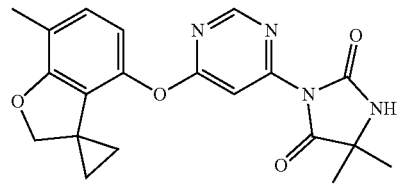

Essentially following the procedures described for example 1-1, using 4-bromo-6-(7-methylspiro[2H-benzofuran-3,1'-cyclopropane]-4-yl)oxy-pyrimidine (120 mg, 0.36 mmol) to afford, after purification by silica gel chromatography eluting with a gradient of ethyl acetate:cyclohexane—0:100 to 100:0 and a Sephadex exclusion chromatography, the title compound as a white foam (35 mg, 24% yield). $^1$H NMR (300 MHz, DMSO-d$_6$) 8.77 (s, 1H), 8.75 (s, 1H), 7.12 (s, 1H), 6.95 (d, J=8.3 Hz, 1H), 6.52 (d, J=8.3 Hz, 1H), 4.43 (s, 2H), 2.13 (s, 3H), 1.38 (s, 6H), 1.06-0.98 (m, 2H), 0.92-0.85 (m, 2H). ESIMS m/z [M+H]+=381.3.

Intermediate 1-65: 2-bromo-4-(3-methoxy-4-methyl-phenoxy)pyrimidine

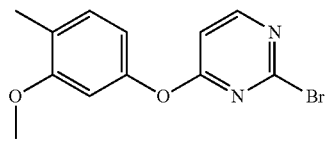 [SMILES: COc1cc(Oc2ccnc(Br)n2)ccc1C]

Essentially following the procedures described for intermediate 1-2, using 2,4-dibromopyrimidine (482 mg, 2.03 mmol) to afford, after purification by silica gel chromatography eluting with a gradient of ethyl acetate:cyclohexane—0:100 to 50:50, the title compound as a white solid (440 mg, 74% yield). ESIMS m/z [M+H]+=294.9-251.9.

Example 48: (5R)-5-ethyl-3-[4-(3-methoxy-4-methyl-phenoxy)pyrimidin-2-yl]-5-methyl-imidazolidine-2,4-dione

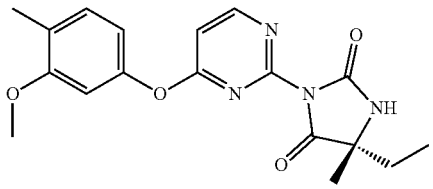 [SMILES: CC[C@@]1(C)NC(=O)N(c2nccc(Oc3ccc(C)c(OC)c3)n2)C1=O]

Essentially following the procedures described for example 1-1, using 2-bromo-4-(3-methoxy-4-methyl-phenoxy)pyrimidine (295 mg, 1.00 mmol) and (5R)-5-ethyl-5-methyl-imidazolidine-2,4-dione (intermediate 1-3, 142 mg, 1.00 mmol) to afford, after purification by silica gel chromatography eluting with a gradient of ethyl acetate:cyclohexane—0:100 to 100:0 and a lyophilisation using acetonitrile and water, the title compound as a white solid (82 mg, 22% yield). $^1$H NMR (300 MHz, DMSO-$d_6$) 8.75 (d, J=5.8 Hz, 1H), 8.56 (bs, 1H), 7.19 (d, J=8.1 Hz, 1H), 7.04 (d, J=5.8 Hz, 1H), 6.90 (d, J=2.2 Hz, 1H), 6.73 (dd, J=2.2 and 8.1 Hz, 1H), 3.75 (s, 3H), 2.13 (s, 3H), 1.80-1.55 (m, 2H), 1.33 (s, 3H), 0.81 (t, J=7.4 Hz, 3H). ESIMS m/z [M+H]+=357.3.

Example 49: 3-[4-(3-methoxy-4-methyl-phenoxy)pyrimidin-2-yl]-1,3-diazaspiro[4.4]nonane-2,4-dione

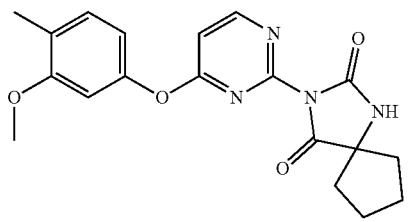 [SMILES: COc1cc(Oc2ccnc(N3C(=O)NC4(CCCC4)C3=O)n2)ccc1C]

Essentially following the procedures described for example 1-1, using 2-bromo-4-(3-methoxy-4-methyl-phenoxy)pyrimidine (200 mg, 0.68 mmol) and 1,3-diazaspiro[4.4]nonane-2,4-dione (105 mg, 0.68 mmol) to afford, after purification by silica gel chromatography eluting with a gradient of ethyl acetate:cyclohexane—0:100 to 70:30, the title compound as a white solid (50 mg, 20% yield). $^1$H NMR (300 MHz, DMSO-$d_6$) 8.85 (bs, 1H), 8.75 (d, J=5.8 Hz, 1H), 7.20 (d, J=8.1 Hz, 1H), 7.06 (d, J=5.8 Hz, 1H), 6.90 (d, J=2.2 Hz, 1H), 6.72 (dd, J=2.2 and 8.1 Hz, 1H), 3.76 (s, 3H), 2.13 (s, 3H), 2.08-1.93 (m, 2H), 1.89-1.69 (m, 6H). ESIMS m/z [M+H]+=369.3.

Example 50: 3-[4-(3-methoxy-4-methyl-phenoxy)pyrimidin-2-yl]-1,3-diazaspiro[4.5]decane-2,4-dione

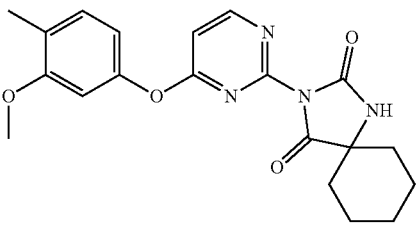 [SMILES: COc1cc(Oc2ccnc(N3C(=O)NC4(CCCCC4)C3=O)n2)ccc1C]

Essentially following the procedures described for example 1-1, using 2-bromo-4-(3-methoxy-4-methyl-phenoxy)pyrimidine (300 mg, 1.02 mmol) and 1,3-diazaspiro[4.5]decane-2,4-dione (171 mg, 1.02 mmol) to afford, after purification by silica gel chromatography eluting with a gradient of ethyl acetate:cyclohexane—0:100 to 100:0, the title compound as a white foam (127 mg, 31% yield). $^1$H NMR (300 MHz, DMSO-$d_6$) 9.06 (bs, 1H), 8.75 (d, J=5.8 Hz, 1H), 7.20 (d, J=8.1 Hz, 1H), 7.04 (d, J=5.8 Hz, 1H), 6.90 (d, J=2.2 Hz, 1H), 6.73 (dd, J=2.2 and 8.1 Hz, 1H), 3.76 (s, 3H), 2.13 (s, 3H), 1.79-1.49 (m, 9H), 1.39-1.22 (m, 1H). ESIMS m/z [M+H]+=383.3.

Intermediate 1-66: 2-bromo-5-fluoro-4-(3-methoxy-4-methyl-phenoxy)pyrimidine

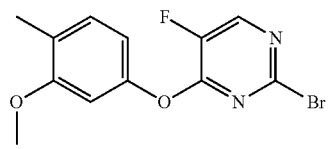 [SMILES: COc1cc(Oc2nc(Br)ncc2F)ccc1C]

To a stirred solution of 4,6-dibromo-5-fluoropyrimidine (200 mg, 0.78 mmol) and 3-methoxy-4-methyl-phenol (120 mg, 0.86 mmol) in DMF (4 mL) at 25° C. was added potassium carbonate (325 mg, 2.35 mmol). After addition, the mixture was stirred at 25° C. for 18 h and 4,6-dibromo-5-fluoropyrimidine (100 mg, 0.39 mmol) was added. The mixture was stirred at 25° C. for 1 h, diluted with water (10 mL) and extracted with ethyl acetate (3×10 mL). The combined organic extracts were washed with saturated aqueous sodium chloride (10 mL), dried over magnesium sulfate, filtered, and concentrated under reduced pressure to afford, after purification by silica gel chromatography eluting with a gradient of ethyl acetate:cyclohexane—0:100 to 10:90, the title compound as a white solid (178 mg, 73% yield). ESIMS m/z [M+H]+=312.9-314.9.

Example 51: 3-[5-fluoro-4-(3-methoxy-4-methyl-phenoxy)pyrimidin-2-yl]-5,5-dimethyl-imidazolidine-2,4-dione

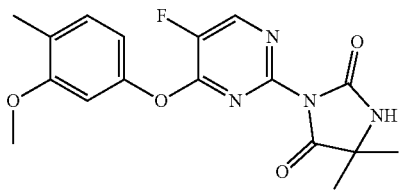

Essentially following the procedures described for example 1-1, using 2-bromo-5-fluoro-4-(3-methoxy-4-methyl-phenoxy)pyrimidine (174 mg, 0.56 mmol) to afford, after purification by silica gel chromatography eluting with a gradient of ethyl acetate:cyclohexane—0:100 to 50:50 and a Sephadex exclusion chromatography, the title compound as a colorless cristallized oil (46 mg, 22% yield). $^1$H NMR (300 MHz, DMSO-$d_6$) 8.94 (d, J=2.4 Hz, 1H), 8.66 (bs, 1H), 7.19 (d, J=8.1 Hz, 1H), 6.98 (d, J=2.1 Hz, 1H), 6.79 (dd, J=2.1 and 8.1 Hz, 1H), 3.78 (s, 3H), 2.14 (s, 3H), 1.34 (s, 6H). ESIMS m/z [M+H]+=361.3.

Example 52: (5R)-5-ethyl-3-[5-fluoro-4-(3-methoxy-4-methyl-phenoxy)pyrimidin-2-yl]-5-methyl-imidazolidine-2,4-dione

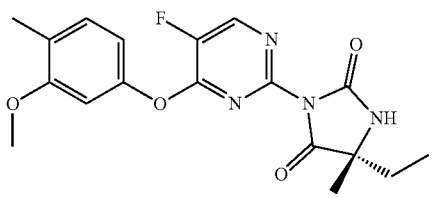 [SMILES: CC[C@@]1(C)NC(=O)N(c2ncc(F)c(Oc3ccc(C)c(OC)c3)n2)C1=O]

Essentially following the procedures described for example 1-1, using 2-bromo-5-fluoro-4-(3-methoxy-4-methyl-phenoxy)pyrimidine (230 mg, 0.74 mmol) and (5R)-5-ethyl-5-methyl-imidazolidine-2,4-dione (intermediate 1-3, 105 mg, 0.74 mmol) to afford, after purification by silica gel chromatography eluting with a gradient of ethyl acetate:cyclohexane—0:100 to 50:50, the title compound as a pale brown foam (92 mg, 31% yield). $^1$H NMR (300 MHz, DMSO-$d_6$) 8.94 (d, J=2.5 Hz, 1H), 8.57 (bs, 1H), 7.19 (d, J=8.1 Hz, 1H), 6.98 (d, J=2.2 Hz, 1H), 6.79 (dd, J=2.2 and 8.1 Hz, 1H), 3.77 (s, 3H), 2.14 (s, 3H), 1.80-1.53 (m, 2H), 1.32 (s, 3H), 0.78 (t, J=7.4 Hz, 3H). ESIMS m/z [M+H]+=375.3.

Intermediate 1-67: 2-chloro-6-(3-methoxy-4-methyl-phenoxy)pyrazine

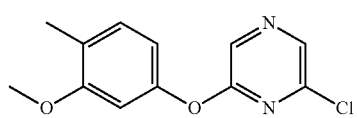 [SMILES: COc1cc(Oc2cncc(Cl)n2)ccc1C]

To a stirred solution of 2,6-dichloropyrazine (500 mg, 3.36 mmol) and 3-methoxy-4-methyl-phenol (460 mg, 3.36 mmol) in DMF (5 mL) at 25° C. was added potassium carbonate (930 g, 6.7 mmol). After addition, the mixture was stirred at 80° C. for 3 h. The resulting mixture was diluted with water (10 mL), extracted with ethyl acetate (3×10 mL), the combined organic extracts were washed with saturated aqueous sodium chloride (10 mL), dried over magnesium sulfate, filtered, and concentrated under reduced pressure to give the title compound as a white solid and pure enough to be used as such (835 mg, 99% yield). $^1$H NMR (300 MHz, DMSO-$d_6$) 8.47 (d, J=1.9 Hz, 2H), 7.18 (d, J=8.1 Hz, 1H), 6.86 (d, J=2.2 Hz, 1H), 6.70 (dd, J=8.1 and 2.2 Hz, 1H), 3.74 (s, 3H), 2.13 (s, 3H).

Example 53: 3-[6-(3-methoxy-4-methyl-phenoxy)pyrazin-2-yl]-5,5-dimethyl-imidazolidine-2,4-dione

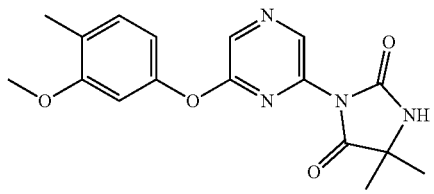

Essentially following the procedures described for example 1-1, using 2-chloro-6-(3-methoxy-4-methyl-phenoxy)pyrazine (500 mg, 2.0 mmol) to afford, after purification by silica gel chromatography eluting with a gradient of ethyl acetate:cyclohexane—0:100 to 100:0, the title compound as a white foam (370 mg, 54% yield). $^1$H NMR (300 MHz, DMSO-$d_6$) 8.72 (s, 1H), 8.47 (s, 2H), 7.16 (d, J=8.4 Hz, 1H), 6.89 (d, J=2.2 Hz, 1H), 6.70 (dd, J=8.4 and 2.2 Hz, 1H), 3.75 (s, 3H), 2.12 (s, 3H), 1.37 (s, 6H). ESIMS m/z [M+H]$^+$=343.3.

Intermediate 1-68: 2-chloro-6-(4-fluoro-3-methoxy-phenoxy)pyrazine

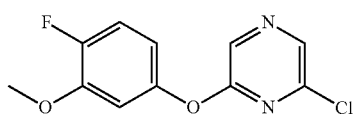

Essentially following the procedures described for intermediate 1-65, using 4-fluoro-3-methoxy-phenol (143 mg, 1.01 mmol) to afford, after purification by silica gel chromatography eluting with a gradient of ethyl acetate:cyclohexane—0:100 to 30:70, the title compound as a white solid (120 mg, 47% yield). ESIMS m/z [M+H]$^+$=255.2.

Example 54: 3-[6-(4-fluoro-3-methoxy-phenoxy)pyrazin-2-yl]-5,5-dimethyl-imidazolidine-2,4-dione

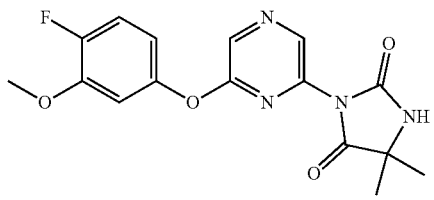

Essentially following the procedures described or example 1-1, using 2-chloro-6-(4-fluoro-3-methoxy-phenoxy)pyrazine (120 mg, 0.47 mmol) to afford, after purification by silica gel chromatography eluting with a gradient of ethyl acetate:cyclohexane—0:100 to 60:40 and a lyophilization using acetonitrile and water, the title compound as a white foam (105 mg, 62% yield). $^1$H NMR (300 MHz, DMSO-$d_6$) 8.73 (s, 1H), 8.53-8.47 (m, 2H), 7.26 (dd, J=8.8 and 11.2 Hz, 1H), 7.17 (dd, J=2.8 and 7.4 Hz, 1H), 6.85-6.76 (m, 1H), 3.80 (s, 3H), 1.37 (s, 6H). ESIMS m/z [M+H]$^+$= 347.3.

Intermediate 2-1:
6-(3-methoxy-4-methyl-phenoxy)pyrimidin-4-amine

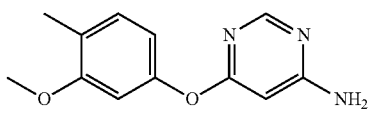 [SMILES: COc1cc(Oc2cc(N)ncn2)ccc1C]

To a solution of 3-methoxy-4-methyl-phenol (280 mg, 2.0 mmol), 2-amino-4-chloropyrimidine (310 mg, 2.4 mmol) in DMF (4 mL) was added $Cs_2CO_3$ (3.26 g, 10.0 mmol). The mixture allowed to stir for 4 h at 100° C. and 18 h at room temperature. The mixture was diluted with EtOAc, washed with $H_2O$ and brine, dried over $MgSO_4$ and conc. in vacuo to afford, after purification by silica gel chromatography, eluting with a gradient of ethyl acetate:cyclohexane—0:100 to 100:0, the title compound as a yellow oil (260 mg, 56% yield). $^1$H NMR (300 MHz, CHCl$_3$-d) 8.29 (s, 1H), 7.13 (d, J=8.2 Hz, 1H), 6.65-6.58 (m, 2H), 5.80 (d, J=0.8 Hz, 1H), 5.06 (bs, 2H), 3.79 (s, 3H), 2.20 (s, 3H).

Intermediate 2-2: tert-butyl N-[(1R)-1-[[6-(3-methoxy-4-methyl-phenoxy)pyrimidin-4-yl]carbamoyl]propyl]carbamate

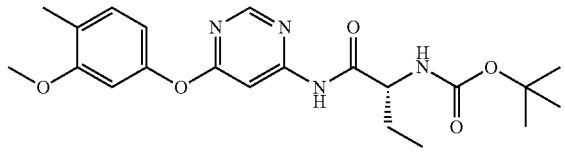 [SMILES: CC[C@@H](NC(=O)OC(C)(C)C)C(=O)Nc1cc(Oc2ccc(C)c(OC)c2)ncn1]

To a solution of Boc-D-Abu-OH (455 mg, 2.24 mmol) in DMF (4 mL) was added DIEA (590 µL, 3.36 mmol) followed by HBTU (1.02 g, 2.70 mmol) and the mixture allowed to stir for 30 min at rt. Then a solution of 6-(3-methoxy-4-methyl-phenoxy)pyrimidin-4-amine (260 mg, 1.12 mmol) in DMF (2 mL) was added and the mixture allowed to stir for 18 h at 80° C. The mixture was hydrolyzed with water, extracted with EtOAc, the organics were washed with brine, dried over $MgSO_4$ and conc. in vacuo to afford, after purification by silica gel chromatography, eluting with a gradient of ethyl acetate:cyclohexane—0:100 to 100:0, the title compound as a yellow oil (215 mg, 46% yield). $^1$H NMR (300 MHz, CHCl$_3$-d) 9.17 (bs, 1H), 8.47 (s, 1H), 7.71 (s, 1H), 7.14 (d, J=8.0 Hz, 1H), 6.65-6.58 (m, 2H), 5.12 (bs, 1H), 4.23 (bs, 1H), 3.79 (s, 3H), 2.20 (s, 3H), 2.02-1.85 (m, 1H), 1.78-1.65 (m, 1H), 1.45 (s, 9H), 1.24 (t, J=7.2 Hz, 3H).

Intermediate 2-3: (2R)-2-amino-N-[6-(3-methoxy-4-methyl-phenoxy)pyrimidin-4-yl]butanamide

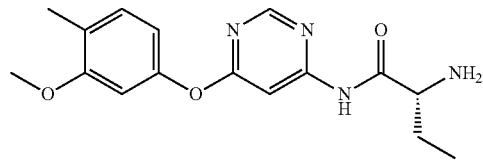 [SMILES: CC[C@@H](N)C(=O)Nc1cc(Oc2ccc(C)c(OC)c2)ncn1]

To a solution of tert-butyl N-[(1R)-1-[[6-(3-methoxy-4-methyl-phenoxy)pyrimidin-4-yl]carbamoyl]propyl]carbamate (215 mg, 0.52 mmol) in DCM (20 mL) at 0° C. was added TFA (2.0 mL) and the mixture allowed to stir for 2 h at 0° C. and 2 h at room temperature. The mixture made basic using $NaHCO_3$, extracted with DCM, dried over $MgSO_4$ and conc. in vacuo to give the title compound as a yellow oil (70 mg, 42% yield). $^1$H NMR (300 MHz, CHCl$_3$-d) 8.50 (s, 1H), 7.91-7.80 (m, 1H), 7.71 (s, 1H), 7.47-7.42 (m, 1H), 7.13 (d, J=7.8 Hz, 1H), 6.65-6.58 (m, 2H), 3.81-3.74 (m, 4H), 3.74-3.58 (m, 1H), 2.19 (s, 3H), 2.05-1.95 (m, 1H), 1.80-1.65 (m, 1H), 1.01 (t, J=7.4 Hz, 3H).

Example 55: (5R)-5-ethyl-3-[6-(3-methoxy-4-methyl-phenoxy)pyrimidin-4-yl]imidazolidine-2,4-dione

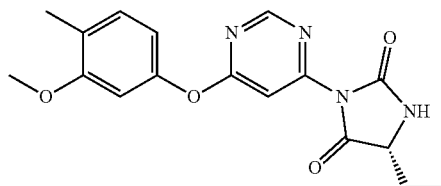

To a solution of (2R)-2-amino-N-[6-(3-methoxy-4-methyl-phenoxy)pyrimidin-4-yl]butanamide (70 mg, 0.22 mmol) in DCM (10 mL) at rt was added TEA (185 µL, 1.32 mmol) and carbonyl diimidazole (110 mg, 0.66 mmol). The mixture was allowed to stir for 3 h at rt. The mixture was hydrolyzed with water, extracted with DCM, dried over $MgSO_4$ and conc. in vacuo to afford, after purification by silica gel chromatography eluting with a gradient of ethyl acetate:cyclohexane—0:100 to 100:0, a semi-preparative purification and a lyophilization using acetonitrile and water, the title compound as a white foam (18 mg, 24% yield). $^1$H NMR (300 MHz, DMSO-$d_6$) 8.77 (d, J=0.8 Hz, 1H), 8.70 (s, 1H), 7.19 (d, J=8.1 Hz, 1H), 7.06 (d, J=0.8 Hz, 1H), 6.86 (d, J=2.1 Hz, 1H), 6.71 (dd, J=8.1 and 2.1 Hz, 1H), 4.21 (t, J=5.5 Hz, 1H), 3.74 (s, 3H), 2.14 (s, 3H), 1.80-1.60 (m, 2H), 0.92 (t, J=7.4 Hz, 3H). ESIMS m/z [M+H]$^+$=343.3.

Intermediate 2-4:
4-(3-methoxy-4-methyl-phenoxy)pyrimidin-2-amine

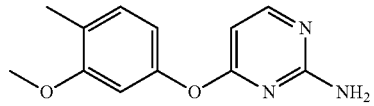

Essentially following the procedures described or intermediate 2-1, using 2-amino-4-chloro-pyrimidine (940 mg, 7.23 mmol). After trituration in ethyl acetate, methanol and dichloromethane, the mixture was filtered. The beige solid gives 875 mg of the title compound and the filtrate was evaporated under reduced pressure and purified by silica gel chromatography, eluting with a gradient of ethyl acetate:cyclohexane—0:100 to 100:0 to gives another 450 mg of the title compound as a white powder (1325 mg, 79% yield). ¹H NMR (300 MHz, DMSO-d₆) 8.08 (d, J=5.5 Hz, 1H), 7.14 (d, J=8.6 Hz, 1H), 6.75 (d, J=2.2 Hz, 1H), 6.64-6.60 (m, 3H), 6.05 (d, J=5.5 Hz, 1H), 3.76 (s, 3H), 2.13 (s, 3H).

Intermediate 2-5: tert-butyl N-[(1R)-1-[[4-(3-methoxy-4-methyl-phenoxy)pyrimidin-2-yl]carbamoyl]propyl]carbamate

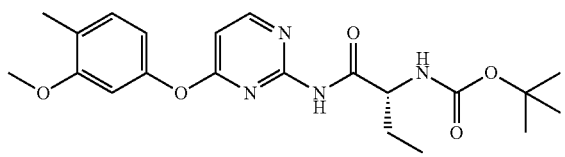 [SMILES: CC[C@@H](NC(=O)OC(C)(C)C)C(=O)Nc1nccc(Oc2ccc(C)c(OC)c2)n1]

Essentially following the procedures described for intermediate 2-2, using 4-(3-methoxy-4-methyl-phenoxy)pyrimidin-2-amine (650 mg, 2.81 mmol) and HATU to afford, after purification by silica gel chromatography, eluting with a gradient of ethyl acetate:cyclohexane—0:100 to 100:0, the title compound as a yellow gum (370 mg, 32% yield). ¹H NMR (300 MHz, CHCl₃-d) 8.66 (bs, 1H), 8.42 (d, J=5.8 Hz, 1H), 7.14 (d, J=8.4 Hz, 1H), 6.67-6.63 (m, 2H), 6.53 (d, J=5.8 Hz, 1H), 5.10 (bs, 1H), 4.64-4.50 (m, 1H), 3.81 (s, 3H), 2.21 (s, 3H), 1.99-1.82 (m, 1H), 1.68-1.58 (m, 1H), 1.43 (s, 9H), 0.93 (t, J=7.4 Hz, 3H). ESIMS m/z [M+H]⁺=417.3.

Intermediate 2-6: (2R)-2-amino-N-[4-(3-methoxy-4-methyl-phenoxy)pyrimidin-2-yl]butanamide

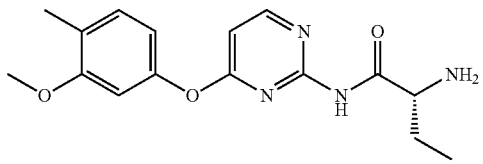 [SMILES: CC[C@@H](N)C(=O)Nc1nccc(Oc2ccc(C)c(OC)c2)n1]

Essentially following the procedures described for intermediate 2-3, using tert-butyl N-[(1R)-1-[[4-(3-methoxy-4-methyl-phenoxy)pyrimidin-2-yl]carbamoyl]propyl]carbamate (370 mg, 0.88 mmol). The solvents were directly removed under reduced pressure and the residue was purified by silica gel chromatography, eluting with a gradient of ethyl acetate:cyclohexane—0:100 to 100:0 followed by a gradient of dichloromethane:methanol—0:100 to 40:60. The TFA salt of the title compound was obtained as a beige gum (325 mg, 84% yield). ¹H NMR (300 MHz, DMSO-d₆) 8.52 (d, J=5.7 Hz, 1H), 8.11 (bs, 3H), 7.17 (d, J=8.2 Hz, 1H), 6.87 (d, J=2.2 Hz, 1H), 6.75-6.69 (m, 2H), 3.76 (s, 3H), 3.67-3.55 (m, 1H), 2.13 (s, 3H), 1.82-1.61 (m, 2H), 0.87 (t, J=7.5 Hz, 3H). ESIMS m/z [M+H]⁺=317.3.

Example 56: (5R)-5-ethyl-3-[4-(3-methoxy-4-methyl-phenoxy)pyrimidin-2-yl]imidazolidine-2,4-dione

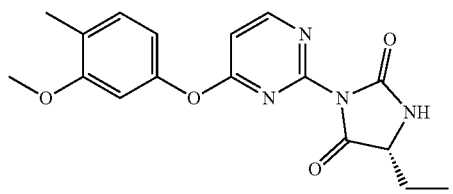 [SMILES: CC[C@H]1NC(=O)N(c2nccc(Oc3ccc(C)c(OC)c3)n2)C1=O]

Essentially following the procedures described for example 2-1, using (2R)-2-amino-N-[4-(3-methoxy-4-methyl-phenoxy)pyrimidin-2-yl]butanamide (320 mg, 0.75 mmol) to afford, after purification by silica gel chromatography eluting with a gradient of ethyl acetate:cyclohexane—0:100 to 100:0, the title compound as a white solid (105 mg, 40% yield). ¹H NMR (300 MHz, DMSO-d₆) 8.78 (d, J=5.8 Hz, 1H), 8.59 (bs, 1H), 7.21 (d, J=8.2 Hz, 1H), 7.09 (d, J=5.8 Hz, 1H), 6.91 (d, J=2.2 Hz, 1H), 6.74 (dd, J=8.2 and 2.2 Hz, 1H), 4.29 (t, J=5.2 Hz, 1H), 3.77 (s, 3H), 2.15 (s, 3H), 1.83-1.60 (m, 2H), 0.91 (t, J=7.4 Hz, 3H). ESIMS m/z [M+H]⁺=343.3.

Intermediate 2-7: 4-(2-aminopyrimidin-4-yl)oxy-3-tert-butyl-benzonitrile

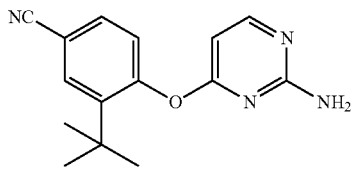 [SMILES: CC(C)(C)c1cc(C#N)ccc1Oc1ccnc(N)n1]

Essentially following the procedures described for intermediate 2-1, using 3-(tert-Butyl)-4-hydroxybenzonitrile (990 mg, 5.64 mmol) and 2-amino-4-chloro-pyrimidine (950 mg, 7.33 mmol) to afford, after purification by silica gel chromatography, eluting with a gradient of ethyl acetate:cyclohexane—0:100 to 75:25, the title compound as a beige solid (835 mg, 55% yield). ¹H NMR (300 MHz, CHCl₃-d) 8.20 (d, J=5.6 Hz, 1H), 7.73 (d, J=2.0 Hz, 1H), 7.51 (dd, J=8.4 and 2.0 Hz, 1H), 7.10 (d, J=8.4 Hz, 1H), 6.24 (d, J=5.6 Hz, 1H), 4.99 (bs, 2H), 1.35 (s, 9H).

Intermediate 2-8: tert-butyl N-[(1R)-1-[[4-(2-tert-butyl-4-cyano-phenoxy)pyrimidin-2-yl]carbamoyl]propyl]carbamate

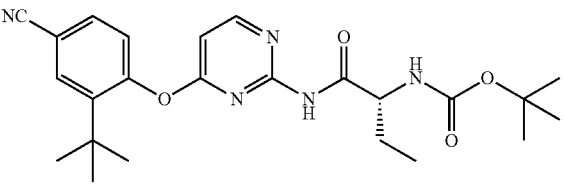 [SMILES: CC[C@@H](NC(=O)OC(C)(C)C)C(=O)Nc1nccc(Oc2ccc(C#N)cc2C(C)(C)C)n1]

Essentially following the procedures described for intermediate 2-2, using 4-(2-aminopyrimidin-4-yl)oxy-3-tertbutyl-benzonitrile (760 mg, 2.83 mmol) and HATU to afford, after purification by silica gel chromatography, eluting with a gradient of ethyl acetate:cyclohexane—0:100 to 50:50, the title compound as a yellow gum (700 mg, 55% yield). ESIMS m/z [M+H]⁺=454.3.

Intermediate 2-9: (2R)-2-amino-N-[4-(2-tert-butyl-4-cyano-phenoxy)pyrimidin-2-yl]butanamide

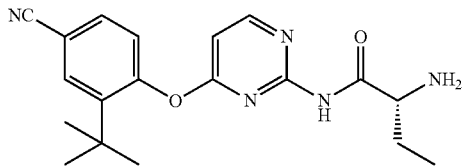 [SMILES: CC[C@@H](N)C(=O)Nc1nccc(Oc2ccc(C#N)cc2C(C)(C)C)n1]

Essentially following the procedures described for intermediate 2-3, using tert-butyl N-[(1R)-1-[[4-(2-tert-butyl-4-cyano-phenoxy)pyrimidin-2-yl]carbamoyl]propyl]carbamate (350 mg, 0.77 mmol) to afford, after purification by silica gel chromatography, eluting with a gradient of ethyl acetate:cyclohexane—0:100 to 100:0, the title compound as a yellow varnish (200 mg, 71% yield). ESIMS m/z [M+H]⁺=354.5.

Example 57: 3-tert-butyl-4-[2-[(4R)-4-ethyl-2,5-dioxo-imidazolidin-1-yl]pyrimidin-4-yl]oxy-benzonitrile

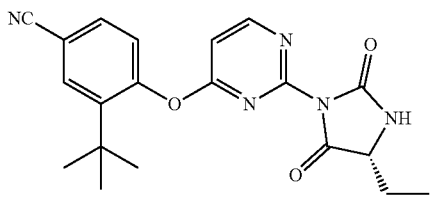 [SMILES: CC[C@H]1NC(=O)N(c2nccc(Oc3ccc(C#N)cc3C(C)(C)C)n2)C1=O]

Essentially following the procedures described for example 2-1, using (2R)-2-amino-N-[4-(2-tert-butyl-4-cyano-phenoxy)pyrimidin-2-yl]butanamide (200 mg, 0.57 mmol) to afford, after purification by silica gel chromatography eluting with a gradient of ethyl acetate:cyclohexane—0:100 to 100:0, a semi-preparative purification and a lyophilization using acetonitrile and water, the title compound as a white solid (66 mg, 29% yield). ¹H NMR (300 MHz, DMSO-d₆) 8.86 (d, J=5.7 Hz, 1H), 8.55 (bs, 1H), 7.85 (d, J=2.0 Hz, 1H), 7.77 (d, J=8.4 and 2.0 Hz, 1H), 7.36 (d, J=8.4 Hz, 1H), 7.35 (d, J=7.5 Hz, 1H), 4.25 (t, J=5.2 Hz, 1H), 1.78-1.55 (m, 2H), 1.29 (s, 9H), 0.86 (t, J=7.4 Hz, 3H). ESIMS m/z [M+H]⁺=380.3.

Intermediate 2-10: 4-(2-phenylphenoxy)pyrimidin-2-amine

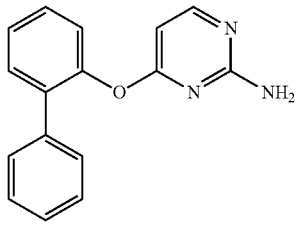 [SMILES: Nc1nccc(Oc2ccccc2-c2ccccc2)n1]

Essentially following the procedures described for intermediate 2-1, using 2-phenyl-phenol (670 mg, 3.92 mmol) and 2-amino-4-chloro-pyrimidine (280 mg, 2.21 mmol) to afford, after purification by silica gel chromatography, eluting with a gradient of ethyl acetate:cyclohexane—0:100 to 100:0, the title compound as a yellow oil (570 mg, Quantitative yield). ¹H NMR (300 MHz, CHCl₃-d) 7.96 (d, J=5.7 Hz, 1H), 7.50-7.20 (m, 8H), 7.17 (dd, J=8.0 and 2.0 Hz, 1H), 5.96 (d, J=5.7 Hz, 1H), 5.09 (bs, 2H).

Intermediate 2-11: tert-butyl N-[(1R)-1-[[4-(2-phenylphenoxy)pyrimidin-2-yl]carbamoyl]propyl]carbamate

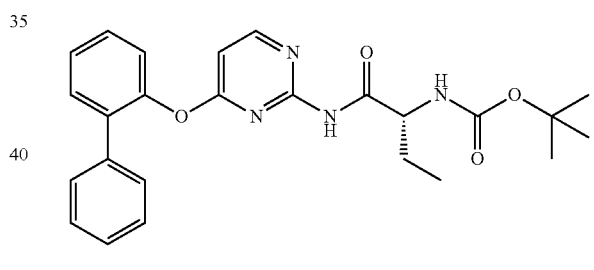

To a solution of 4-(2-phenylphenoxy)pyrimidin-2-amine (570 mg, 2.21 mmol) in THF (40 mL) at 0° C. was added 1 N tert-Butylmagnesium chloride in THF (5.2 mL, 5.16 mmol). After 15 minutes at 0° C. and 10 minutes at rt, the solution was cooled again to 0° C. and methyl (2R)-2-(tert-butoxycarbonylamino)butanoate (280 mg, 1.29 mmol) was added. The mixture was stirred at RT for 3 h. The reaction was cooled to 0° C. and saturated NH₄Cl (10 mL) was added. The mixture was concentrated to remove THF, water was added (10 mL) and the solution was extracted with EtOAc (3×10 mL). The organic extracts were dried over magnesium sulfate, filtered and evaporated. The residue was purified twice by silica gel chromatography, eluting with a gradient of ethyl acetate:cyclohexane—0:100 to 50:50, to afford the title compound as a yellow oil (290 mg, 50% yield). ¹H NMR (300 MHz, CHCl₃-d) 8.54 (bs, 1H), 8.30 (d, J=5.7 Hz, 1H), 7.50-7.12 (m, 9H), 6.36 (d, J=5.7 Hz, 1H), 5.10 (bs, 1H), 4.85-4.60 (m, 1H), 1.90-1.70 (m, 1H), 1.62-1.48 (m, 1H), 1.42 (s, 9H), 0.89 (t, J=7.3 Hz, 3H).

Intermediate 2-12: (2R)-2-amino-N-[4-(2-phenylphenoxy)pyrimidin-2-yl]butanamide

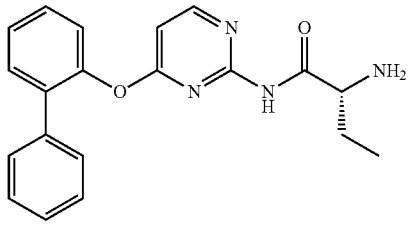 [SMILES: CC[C@@H](N)C(=O)Nc1nccc(Oc2ccccc2-c2ccccc2)n1]

Essentially following the procedures described for intermediate 2-3, using tert-butyl N-[(1R)-1-[[4-(2-phenylphenoxy)pyrimidin-2-yl]carbamoyl]propyl]carbamate (290 mg, 0.64 mmol) to afford, after purification by silica gel chromatography, eluting with a gradient of ethyl acetate:cyclohexane—0:100 to 100:0 followed by a gradient of ethyl acetate:methanol—100:0 to 80:20, the title compound as a colorless oil (210 mg, 93% yield). $^1$H NMR (300 MHz, CHCl$_3$-d) 8.36 (d, J=5.7 Hz, 1H), 7.55-7.15 (m, 9H), 6.33 (d, J=5.7 Hz, 1H), 3.61-3.44 (m, 1H), 2.02-1.51 (m, 4H), 0.97 (t, J=7.4 Hz, 3H).

Example 58: (5R)-5-ethyl-3-[4-(2-phenylphenoxy)pyrimidin-2-yl]imidazolidine-2,4-dione

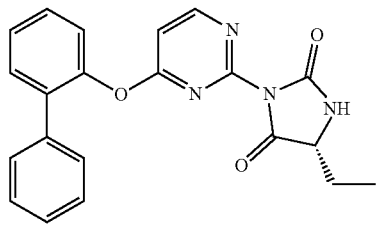 [SMILES: CC[C@H]1NC(=O)N(c2nccc(Oc3ccccc3-c3ccccc3)n2)C1=O]

Essentially following the procedures described for example 2-1, using (2R)-2-amino-N-[4-(2-phenylphenoxy)pyrimidin-2-yl]butanamide (210 mg, 0.60 mmol) to afford, after purification by silica gel chromatography eluting with a gradient of ethyl acetate:cyclohexane—0:100 to 100:0, the title compound as a white solid (145 mg, 64% yield). $^1$H NMR (300 MHz, DMSO-d$_6$) 8.67 (d, J=5.7 Hz, 1H), 8.53 (bs, 1H), 7.50-7.22 (m, 9H), 7.01 (d, J=7.5 Hz, 1H), 4.24 (t, J=5.2 Hz, 1H), 1.82-1.52 (m, 2H), 0.86 (t, J=7.4 Hz, 3H). ESIMS m/z [M+H]$^+$=375.1.

Intermediate 2-13: 2-(3-methoxy-4-methyl-phenoxy)pyrimidin-4-amine

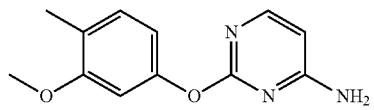 [SMILES: COc1cc(Oc2nccc(N)n2)ccc1C]

Essentially following the procedures described or intermediate 2-1, using 2-chloro-4-amino-pyrimidine (940 mg, 7.24 mmol) and heating the mixture for 18 h to afford, after purification by silica gel chromatography, eluting with a gradient of ethyl acetate:cyclohexane—0:100 to 100:0, the title compound as a beige solid (890 mg, 53% yield). $^1$H NMR (300 MHz, DMSO-d$_6$) 7.82 (d, J=5.7 Hz, 1H), 7.07 (d, J=8.1 Hz, 1H), 6.96 (bs, 2H), 6.67 (d, J=2.1 Hz, 1H), 6.54 (dd, J=8.1 and 2.1 Hz, 1H), 6.11 (d, J=5.7 Hz, 1H), 3.72 (s, 3H), 2.09 (s, 3H).

Intermediate 2-14: tert-butyl N-[(1R)-1-[[2-(3-methoxy-4-methyl-phenoxy)pyrimidin-4-yl]carbamoyl]propyl]carbamate

Essentially following the procedures described for intermediate 2-11, using 2-(3-methoxy-4-methyl-phenoxy)pyrimidin-4-amine (300 mg, 1.3 mmol) and stirred for 18 h to afford, after purification by silica gel chromatography, eluting with a gradient of ethyl acetate:cyclohexane—0:100 to 100:0, the title compound as a colorless varnish (200 mg, 74% yield). $^1$H NMR (300 MHz, CHCl$_3$-d) 9.34 (bs, 1H), 8.39 (d, J=5.6 Hz, 1H), 7.89 (d, J=5.3 Hz, 1H), 7.09 (d, J=8.5 Hz, 1H), 6.70-6.55 (m, 2H), 5.39 (bs, 1H), 4.40-4.25 (m, 1H), 3.76 (s, 3H), 2.17 (s, 3H), 2.00-1.85 (m, 1H), 1.80-1.61 (m, 1H), 1.41 (s, 9H), 0.95 (t, J=7.2 Hz, 3H).

Intermediate 2-15: (2R)-2-amino-N-[2-(3-methoxy-4-methyl-phenoxy)pyrimidin-4-yl]butanamide

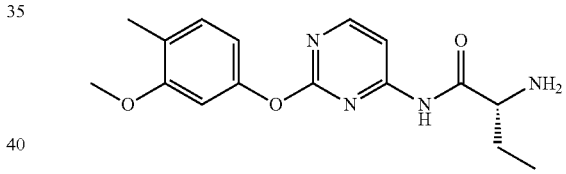

Essentially following the procedures described for intermediate 2-3, using tert-butyl N-[(1R)-1-[[2-(3-methoxy-4-methyl-phenoxy)pyrimidin-4-yl]carbamoyl]propyl]carbamate (635 mg, 1.52 mmol) to afford the title compound as a white foam (460 mg, 95% yield). $^1$H NMR (300 MHz, DMSO-d$_6$) 8.49 (d, J=5.6 Hz, 1H), 7.77 (d, J=5.6 Hz, 1H), 8.00-7.50 (bs, 2H), 7.13 (d, J=8.2 Hz, 1H), 6.78 (d, J=2.2 Hz, 1H), 6.63 (dd, J=8.2 and 2.2 Hz, 1H), 3.80-3.70 (m, 1H), 3.73 (s, 3H), 2.12 (s, 3H), 1.80-1.56 (m, 2H), 0.88 (t, J=7.4 Hz, 3H).

Example 59: (5R)-5-ethyl-3-[2-(3-methoxy-4-methyl-phenoxy)pyrimidin-4-yl]imidazolidine-2,4-dione

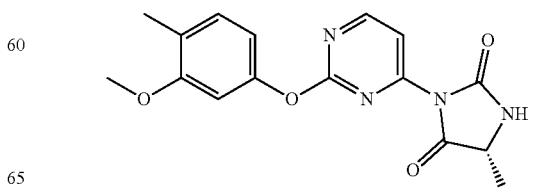

To a solution of (2R)-2-amino-N-[2-(3-methoxy-4-methyl-phenoxy)pyrimidin-4-yl]butanamide (300 mg, 0.95 mmol) in DCM (20 mL) at 0° C. were added Triethylamine (480 mg, 4.74 mmol) and a solution of Triphosgene (127 mg, 0.43 mmol) in DCM (2 mL). The mixture was stirred at 0° C. for 30 min. The mixture was diluted with water (15 mL) and DCM (10 mL), the two phases were separated, the aqueous phase was extracted with DCM (3×15 mL). The organic extracts were dried over magnesium sulfate, filtered and evaporated. The residue was purified by silica gel chromatography, eluting with a gradient of ethyl acetate:cyclohexane—0:100 to 100:0, and a semi-preparative purification to afford after lyophilization using methanol and water, the title compound as a white solid (55 mg, 17% yield). $^1$H NMR (300 MHz, DMSO-$d_6$) 8.76 (bs, 1H), 8.74 (d, J=5.3 Hz, 1H), 7.31 (d, J=5.3 Hz, 1H), 7.16 (d, J=8.1 Hz, 1H), 6.88 (d, J=2.1 Hz, 1H), 6.71 (dd, J=8.1 and 2.1 Hz, 1H), 4.24 (t, J=5.7 Hz, 1H), 3.76 (s, 3H), 2.14 (s, 3H), 1.86-1.60 (m, 2H), 0.93 (t, J=7.4 Hz, 3H). ESIMS m/z [M+H]$^+$=343.1.

Intermediate 3-1: tert-butyl N-[2-[(4-chloropyrimidin-2-yl)amino]-1,1-dimethyl-2-oxo-ethyl]carbamate

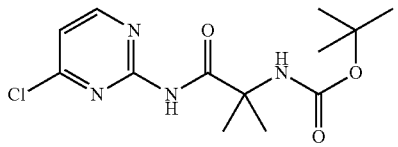 [SMILES: CC(C)(C)OC(=O)NC(C)(C)C(=O)Nc1nccc(Cl)n1]

Essentially following the procedures described for intermediate 2-11, using 2-amino-4-chloro-pyrimidine (1.20 g, 9.21 mmol) and methyl 2-(tert-butoxycarbonylamino)-2-methyl-propanoate (1.0 g, 4.60 mmol) to afford, after purification by silica gel chromatography, eluting with a gradient of ethyl acetate:cyclohexane—0:100 to 50:50, the title compound as a white solid (480 mg, 33% yield). $^1$H NMR (300 MHz, CHCl$_3$-d) 10.14 (s, 1H), 8.61 (d, J=5.3 Hz, 1H), 7.33 (d, J=5.3 Hz, 1H), 6.94 (bs, 1H), 3.35 (s, 9H).

Intermediate 3-2: tert-butyl N-[2-[[4-(3-methoxy-4-methyl-phenoxy)pyrimidin-2-yl]amino]-1,1-dimethyl-2-oxo-ethyl]carbamate

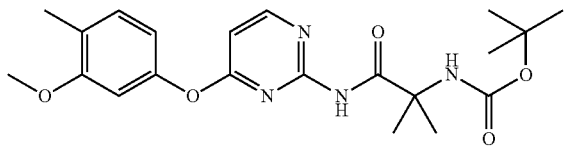 [SMILES: COc1cc(Oc2ccnc(NC(=O)C(C)(C)NC(=O)OC(C)(C)C)n2)ccc1C]

Essentially following the procedures described for intermediate 2-1, using tert-butyl N-[2-[(4-chloropyrimidin-2-yl)amino]-1,1-dimethyl-2-oxo-ethyl]carbamate (400 mg, 1.27 mmol) to afford, after purification by silica gel chromatography, eluting with a gradient of ethyl acetate:cyclohexane—0:100 to 100:0, the title compound as a colorless varnish (170 mg, 32% yield). ESIMS m/z [M+H]$^+$=417.1.

Intermediate 3-3: 2-amino-N-[4-(3-methoxy-4-methyl-phenoxy)pyrimidin-2-yl]-2-methyl-propanamide

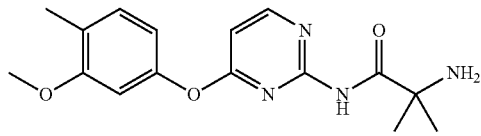 [SMILES: COc1cc(Oc2ccnc(NC(=O)C(C)(C)N)n2)ccc1C]

Essentially following the procedures described for intermediate 2-3, using tert-butyl N-[2-[[4-(3-methoxy-4-methyl-phenoxy)pyrimidin-2-yl]amino]-1,1-dimethyl-2-oxo-ethyl]carbamate (170 mg, 0.41 mmol) to afford the title compound as a colorless varnish (120 mg, 93% yield). ESIMS m/z [M+H]$^+$=317.4.

Example 60: 3-[4-(3-methoxy-4-methyl-phenox)pyrimidin-2-yl]-5,5-dimethyl-imidazolidine-2,4-dione

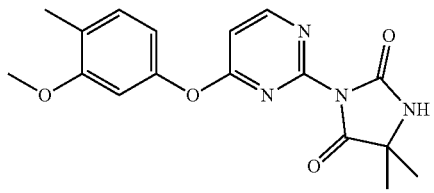

Essentially following the procedures described for example 2-1, using 2-amino-N-[4-(3-methoxy-4-methyl-phenoxy)pyrimidin-2-yl]-2-methyl-propanamide (120 mg, 0.38 mmol) to afford, after purification by silica gel chromatography eluting with a gradient of ethyl acetate:cyclohexane—0:100 to 100:0, and lyophilization using MeOH/water the title compound as a white solid (89 mg, 66% yield). $^1$H NMR (300 MHz, DMSO-$d_6$) 8.75 (d, J=5.7 Hz, 1H), 8.66 (bs, 1H), 7.20 (d, J=8.1 Hz, 1H), 7.05 (d, J=7.5 Hz, 1H), 6.90 (d, J=2.2 Hz, 1H), 6.73 (dd, J=8.1 and 2.2 Hz, 1H), 3.76 (s, 3H), 2.13 (s, 3H), 1.36 (s, 6H). ESIMS m/z [M+H]$^+$=343.3.

Intermediate 3-4: 2-iodo-5-isopropyl-phenol and 4-iodo-3-isopropyl-phenol

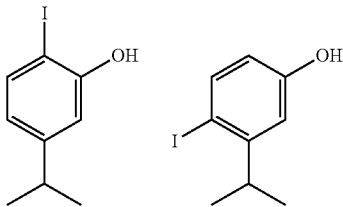

To a stirred solution of 3-isopropylphenol (4.02 mL, 29.4 mmol) in methanol (70 mL) was added a solution of Iodine monochloride (4.77 g, 29.4 mmol) in methanol (70 mL) over 1 hour. After stirring at room temperature for 16 hours, the mixture was quenched with 20% aq. Na$_2$S$_2$O$_3$ (10 mL) and stirred for 20 min. Water was added (50 mL) and the organics were extracted with EtOAc (3×40 mL). The combined organic extracts were dried over MgSO₄, filtered and the solvent was evaporated in vacuo. The residue was purified by silica gel chromatography eluting with a gradient of dichloromethane:cyclohexane—0:100 to 50:50, to afford 2-iodo-5-isopropyl-phenol (3.23 g, 34% yield), Rf: 0.37 (CH₂Cl₂/cyclohexane 1:1). ¹H NMR (300 MHz, DMSO-d₆) 7.51 (d, J=8.0 Hz, 1H), 6.73 (d, J=2.0 Hz, 1H), 6.47 (dd, J=8.0 and 2.0 Hz, 1H), 2.74 (sept, J=6.9 Hz, 1H), 1.12 (d, J=6.9 Hz, 6H) and 4-iodo-3-isopropyl-phenol (3.9 g, 35% yield) Rf: 0.12 (CH₂Cl₂/cyclohexane 1:1). ¹H NMR (300 MHz, DMSO-d₆) 9.56 (s, 1H), 7.53 (d, J=8.5 Hz, 1H), 6.72 (d, J=2.9 Hz, 1H), 6.41 (dd, J=8.5 and 2.9 Hz, 1H), 2.96 (sept, J=6.8 Hz, 1H), 1.11 (d, J=6.8 Hz, 6H).

Intermediate 3-5:
4-hydroxy-2-isopropyl-benzonitrile

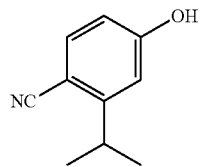

A solution of 4-iodo-3-isopropyl-phenol (2.85 g, 10.9 mmol) in NMP (20 mL) was treated with copper cyanide (1.27 g, 14.1 mmol) and stirred at 180° C. for 1.5 hours. The reaction mixture was cooled to 20° C. and diluted with diethylether (200 mL). The resulting suspension was filtered through Celite. The filtrate was washed with water and brine. The organic fraction was dried over MgSO₄, filtered and the solvent was evaporated in vacuo. The residue was purified by silica gel chromatography eluting with a gradient of dichloromethane:cyclohexane—0:100 to 30:70 to afford the title compound as a red solid (1.73 g, 99% yield). ¹H NMR (300 MHz, DMSO-d₆) 10.48 (s, 1H), 7.54 (d, J=8.5 Hz, 1H), 6.80 (d, J=2.3 Hz, 1H), 6.71 (dd, J=8.5 and 2.3 Hz, 1H), 3.11 (sept, J=6.9 Hz, 1H), 1.20 (d, J=6.9 Hz, 6H).

Intermediate 3-6: tert-butyl N-[2-[[4-(4-cyano-3-isopropyl-phenoxy)pyrimidin-2-yl]amino]-1,1-dimethyl-2-oxo-ethyl]carbamate

Essentially following the procedures described for intermediate 2-1, using tert-butyl N-[2-[(4-chloropyrimidin-2-yl)amino]-1,1-dimethyl-2-oxo-ethyl]carbamate (400 mg, 1.27 mmol) and 4-hydroxy-2-isopropyl-benzonitrile (205 mg, 1.27 mmol) to afford, after purification by silica gel chromatography, eluting with a gradient of ethyl acetate:cyclohexane—0:100 to 70:30, the title compound as a colorless foam (295 mg, 28% yield). ESIMS m/z [M+H]⁺=440.4.

Intermediate 3-7: 2-amino-N-[4-(4-cyano-3-isopropyl-phenoxy)pyrimidin-2-yl]-2-methyl-propanamide

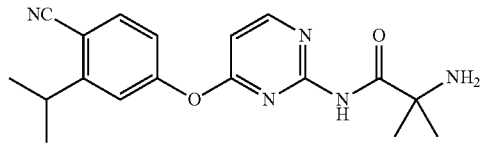 [SMILES: CC(C)c1cc(Oc2ccnc(NC(=O)C(C)(C)N)n2)ccc1C#N]

Essentially following the procedures described for intermediate 2-3, using tert-butyl N-[2-[[4-(4-cyano-3-isopropyl-phenoxy)pyrimidin-2-yl]amino]-1,1-dimethyl-2-oxo-ethyl]carbamate (295 mg, 0.67 mmol) to afford the title compound as a yellow oil (175 mg, 64% yield). ESIMS m/z [M+H]⁺= 340.3.

Example 61: 4-[2-(4,4-dimethyl-2,5-dioxo-imidazolidin-1-yl)pyrimidin-4-yl]oxy-2-isopropyl-benzonitrile

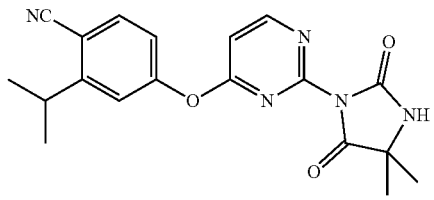 [SMILES: CC(C)c1cc(Oc2ccnc(N3C(=O)NC(C)(C)C3=O)n2)ccc1C#N]

Essentially following the procedures described for example 2-1, using 2-amino-N-[4-(4-cyano-3-isopropyl-phenoxy)pyrimidin-2-yl]-2-methyl-propanamide (175 mg, 0.52 mmol) to afford, after purification by silica gel chromatography eluting with a gradient of ethyl acetate:cyclohexane—0:100 to 100:0, a Sephadex exclusion chromatography and a lyophilization using methanol and water the title compound as a colorless foam (19 mg, 10% yield). ¹H NMR (300 MHz, DMSO-d₆) 8.86 (d, J=5.7 Hz, 1H), 8.66 (bs, 1H), 7.88 (d, J=8.5 Hz, 1H), 7.51 (d, J=2.3 Hz, 1H), 7.32 (dd, J=8.5 and 2.3 Hz, 1H), 7.28 (d, J=5.7 Hz, 1H), 3.23 (sept, J=6.9 Hz, 1H), 1.34 (s, 6H), 1.24 (d, J=6.9 Hz, 6H). ESIMS m/z [M+H]⁺=366.3.

Intermediate 4-1: (5R)-5-ethyl-5-methyl-3-(2-methylsulfanylpyrimidin-4-yl)imidazolidine-2,4-dione

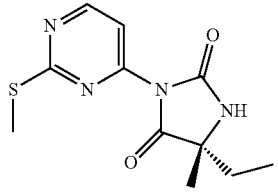 [SMILES: CC[C@@]1(C)NC(=O)N(c2ccnc(SC)n2)C1=O]

Essentially following the procedures described for example 1-1, using 4-Iodo-2-(methylthio)pyrimidine (500 mg, 2.0 mmol) and (5R)-5-ethyl-5-methyl-imidazolidine-2,4-dione (370 mg, 2.6 mmol), to afford, after purification by by silica gel chromatography eluting with a gradient of ethyl acetate:cyclohexane—0:100 to 100:0 the title compound as colorless oil (283 mg, 54% yield). ¹H NMR (300 MHz, CHCl₃-d) 8.61 (d, J=5.3 Hz, 1H), 7.16 (d, J=5.3 Hz, 1H), 5.74 (bs, 1H), 2.57 (s, 3H), 2.03-1.92 (m, 1H), 1.82-1.70 (m, 1H), 1.54 (s, 3H), 0.98 (t, J=7.4 Hz, 3H).

Intermediate 4-2: (5R)-5-ethyl-5-methyl-3-(2-methylsulfonylpyrimidin-4-yl)imidazolidine-2,4-dione

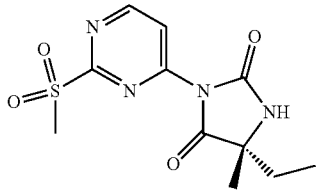 [SMILES: CC[C@@]1(C)NC(=O)N(c2ccnc(S(C)(=O)=O)n2)C1=O]

(5R)-5-ethyl-5-methyl-3-(2-methylsulfanylpyrimidin-4-yl)imidazolidine-2,4-dione (280 mg, 1.05 mmol) was solubilized in DCM (25 mL) and the solution was cooled to 0° C. mCPBA (544 mg, 2.21 mmol) (70% weight) was added in one portion and the reaction was allowed to reach to room temperature slowly. The reaction mixture was stirred at room temperature for 2 hours. The reaction mixture was quenched with aqueous saturated K₂CO₃ solution and brine, the organics were extracted with DCM (2×50 mL) and the combined extracts were dried over magnesium sulfate. The solvent was evaporated in vacuo to afford crude title compound as a white foam (320 mg, 74% yield). ¹H NMR (300 MHz, CHCl₃-d) 8.61 (d, J=5.3 Hz, 1H), 7.16 (d, J=5.3 Hz, 1H), 5.74 (bs, 1H), 2.57 (s, 3H), 2.03-1.92 (m, 1H), 1.82-1.70 (m, 1H), 1.54 (s, 3H), 0.98 (t, J=7.4 Hz, 3H). ESIMS m/z [M+H]⁺=299.4.

Example 62: (5R)-5-ethyl-3-[2-(3-methoxy-4-methyl-phenoxy)pyrimidin-4-yl]-5-methyl-imidazolidine-2,4-dione

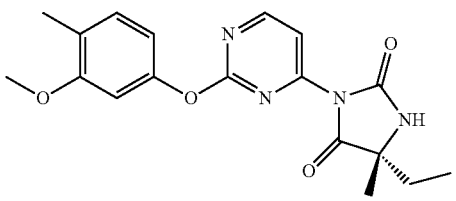 [SMILES: CC[C@@]1(C)NC(=O)N(c2ccnc(Oc3ccc(C)c(OC)c3)n2)C1=O]

Potassium carbonate (278 mg, 2.0 mmol) was added to a mixture of (5R)-5-ethyl-5-methyl-3-(2-methylsulfonylpyrimidin-4-yl)imidazolidine-2,4-dione (300 mg, 1.0 mmol) and 3-methoxy-4-methyl-phenol (139 mg, 1.0 mmol) in DMF (5 mL) and the reaction mixture was stirred at room temperature for 18 hours. The reaction mixture was hydrolyzed in water (100 mL) and the organics were extracted with diethyl ether (2×75 mL). The combined extracts were dried over magnesium sulfate, filtered and the solvent was evaporated in vacuo. The residue was purified by silica gel chromatography eluting with a gradient of ethyl acetate:cyclohexane—0:100 to 100:0 to afford, after a lyophilization using acetonitrile and water, title compound as white solid (196 mg, 53% yield). ¹H NMR (300 MHz, DMSO-d₆) 8.73 (bs, 1H), 8.71 (d, J=5.3 Hz, 1H), 7.32 (d, J=5.3 Hz, 1H), 7.14 (d, J=8.1 Hz, 1H), 6.86 (d, J=2.2 Hz, 1H), 6.69 (dd, J=8.1 and 2.2 Hz, 1H), 3.74 (s, 3H), 2.12 (s, 3H), 1.83-1.56 (m, 2H), 1.37 (s, 3H), 0.83 (t, J=7.3 Hz, 3H). ESIMS m/z [M+H]⁺=357.4.

Intermediate 4-3: 5,5-dimethyl-3-(2-methylsulfanylpyrimidin-4-yl)imidazolidine-2,4-dione

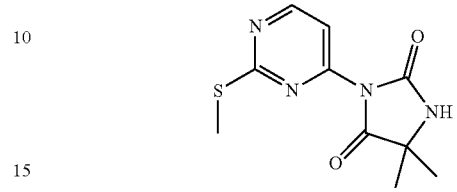

In a sealable vessel, a mixture of 4-Iodo-2-(methylthio)pyrimidine (500 mg, 2.0 mmol), 5,5-dimethyl-imidazolidine-2,4-dione (760 mg, 6.0 mmol), and copper (I) oxide (280 mg, 2.0 mmol) in DMA (5 mL) was sealed and stirred at 150° C. for 18 h. After cooling, the reaction mixture was quenched in water (100 mL), extracted with Et₂O (3×50 mL) and the combined extracts were dried over magnesium sulfate, filtered and the solvent was evaporated in vacuo. The residue was purified by silica gel chromatography, eluting with a gradient of ethyl acetate:cyclohexane—0:100 to 0:100, to afford the title compound as a colorless oil (310 mg, 62% yield). ¹H NMR (300 MHz, CHCl₃-d) 8.61 (d, J=5.3 Hz, 1H), 7.18 (d, J=5.3 Hz, 1H), 5.93 (bs, 1H), 2.58 (s, 3H), 1.56 (s, 6H).

Intermediate 4-4: 5,5-dimethyl-3-(2-methylsulfonylpyrimidin-4-yl)imidazolidine-2,4-dione

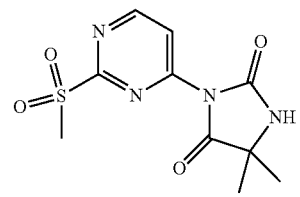 [SMILES: CC1(C)NC(=O)N(c2ccnc(S(C)(=O)=O)n2)C1=O]

Essentially following the procedures described for intermediate 4-2, using 5,5-dimethyl-3-(2-methylsulfanylpyrimidin-4-yl)imidazolidine-2,4-dione (300 mg, 1.2 mmol), to afford, after purification by silica gel chromatography eluting with a gradient of ethyl acetate:cyclohexane—0:100 to 100:0 the title compound as white solid (85 mg, 25% yield). ESIMS m/z [M+H]⁺=285.3.

Example 63: 3-[2-(3-methoxy-4-methyl-phenoxy)pyrimidin-4-yl]-5,5-dimethyl-imidazolidine-2,4-dione

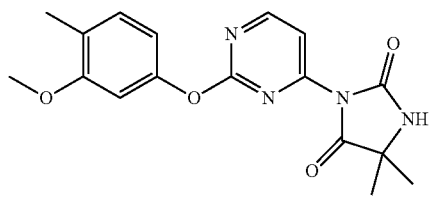

Essentially following the procedures described for example 4-1, using 5,5-dimethyl-3-(2-methylsulfonylpyrimidin-4-yl)imidazolidine-2,4-dione (80 mg, 0.3 mmol), to afford, after semi-preparative purification and a lyophilization using acetonitrile and water, the title compound as a white foam (38 mg, 39% yield). $^1$H NMR (300 MHz, DMSO-$d_6$) 8.77 (bs, 1H), 8.71 (d, J=5.3 Hz, 1H), 7.33 (d, J=5.3 Hz, 1H), 7.14 (d, J=8.1 Hz, 1H), 6.86 (d, J=2.2 Hz, 1H), 6.69 (dd, J=2.2 and 8.1 Hz, 1H), 3.75 (s, 3H), 2.12 (s, 3H), 1.38 (s, 6H). ESIMS m/z [M+H]$^+$=343.3.

Example 64: 3-[2-(3-methoxy-4-fluoro-phenoxy)pyrimidin-4-yl]-5,5-dimethyl-imidazolidine-2,4-dione

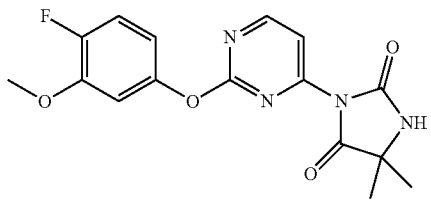

Essentially following the procedures described for example 4-1, using 5,5-dimethyl-3-(2-methylsulfonylpyrimidin-4-yl)imidazolidine-2,4-dione (100 mg, 0.35 mmol) and 4-fluoro-3-methoxyphenol (50 mg, 0.35 mmol), to afford, after purification by silica gel chromatography, eluting with a gradient of ethyl acetate:dichloromethane—0:100 to 100:0, the title compound as a white solid (44 mg, 36% yield). $^1$H NMR (300 MHz, DMSO-$d_6$) 8.78 (bs, 1H), 8.73 (d, J=5.2 Hz, 1H), 7.36 (d, J=5.1 Hz, 1H), 7.30-7.20 (m, 1H), 7.20-7.11 (m, 1H), 6.88-6.72 (m, 1H), 3.80 (s, 3H), 1.38 (s, 6H). ESIMS m/z [M+H]$^+$=347.3.

Example 65: 3-[2-[3-methoxy-4-(trifluoromethyl)-phenoxy]pyrimidin-4-yl]-5,5-dimethyl-imidazolidine-2,4-dione

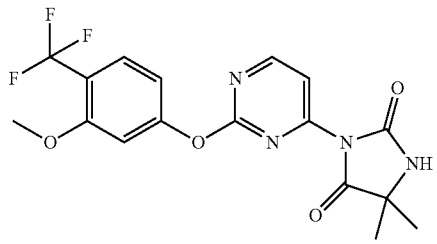

Essentially following the procedures described for example 4-1, using 5,5-dimethyl-3-(2-methylsulfonylpyrimidin-4-yl)imidazolidine-2,4-dione (100 mg, 0.35 mmol) and 3-methoxy-4-(trifluoromethyl)phenol (68 mg, 0.35 mmol), to afford, after purification by silica gel chromatography, eluting with a gradient of ethyl acetate:dichloromethane—0:100 to 100:0 and a lyophilization using methanol and water, the title compound as a white foam (90 mg, 63% yield). $^1$H NMR (300 MHz, DMSO-$d_6$) 8.80 (bs, 1H), 8.77 (d, J=5.3 Hz, 1H), 7.65 (d, J=8.6 Hz, 1H), 7.42 (d, J=5.3 Hz, 1H), 7.27 (d, J=1.7 Hz, 1H), 6.98 (dd, J=8.6 and 1.7 Hz, 1H), 3.86 (s, 3H), 1.39 (s, 6H). ESIMS m/z [M+H]$^+$=397.3.

Example 66: 3-[2-(4-chloro-3-methoxy-phenoxy)pyrimidin-4-yl]-5,5-dimethyl-imidazolidine-2,4-dione

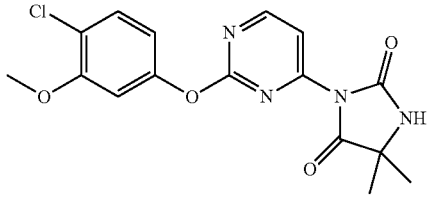

Essentially following the procedures described for example 4-1, using 5,5-dimethyl-3-(2-methylsulfonylpyrimidin-4-yl)imidazolidine-2,4-dione (100 mg, 0.35 mmol) and 4-chloro-3-methoxy-phenol (56 mg, 0.35 mmol), to afford, after purification by silica gel chromatography, eluting with a gradient of ethyl acetate:dichloromethane—0:100 to 100:0, the title compound as a white solid (45 mg, 35% yield). $^1$H NMR (300 MHz, DMSO-$d_6$) 8.79 (bs, 1H), 8.74 (d, J=5.3 Hz, 1H), 7.45 (d, J=8.6 Hz, 1H), 7.38 (d, J=5.3 Hz, 1H), 7.14 (d, J=2.3 Hz, 1H), 6.85 (dd, J=2.1 and 8.6 Hz, 1H), 3.83 (s, 3H), 1.38 (s, 6H). ESIMS m/z [M+H]$^+$=363.3.

Example 67: 3-[2-(3-fluoro-4-methyl-phenoxy)pyrimidin-4-yl]-5,5-dimethyl-imidazolidine-2,4-dione

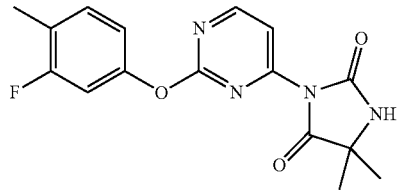

Essentially following the procedures described for example 4-1, using 5,5-dimethyl-3-(2-methylsulfonylpyrimidin-4-yl)imidazolidine-2,4-dione (70 mg, 0.25 mmol) and 3-fluoro-4-methylphenol (31 mg, 0.25 mmol), to afford, after purification by silica gel chromatography, eluting with a gradient of ethyl acetate:dichloromethane—0:100 to 100:0, the title compound as a white solid (60 mg, 73% yield). $^1$H NMR (300 MHz, DMSO-$d_6$) 8.78 (bs, 1H), 8.72 (d, J=5.3 Hz, 1H), 7.37 (d, J=5.3 Hz, 1H), 7.32 (app. t, J=8.6 and 8.8 Hz, 1H), 7.18 (dd, J=2.3 and 10.7 Hz, 1H), 7.00 (dd, J=2.3 and 8.3 Hz, 1H), 2.22 (s, 3H), 1.38 (s, 6H). ESIMS m/z [M+H]$^+$=331.3.

Example 68: 3-[2-(benzofuran-6-yloxy)pyrimidin-4-yl]-5,5-dimethyl-imidazolidine-2,4-dione

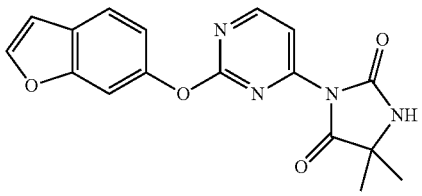 [SMILES: CC1(C)NC(=O)N(c2ccnc(Oc3ccc4ccoc4c3)n2)C1=O]

Essentially following the procedures described for example 4-1, using 5,5-dimethyl-3-(2-methylsulfonylpyrimidin-4-yl)imidazolidine-2,4-dione (70 mg, 0.25 mmol) and benzofuran-6-ol (33 mg, 0.25 mmol), to afford, after purification by silica gel chromatography, eluting with a gradient of ethyl acetate:dichloromethane—0:100 to 100:0, semi-preparative purification and a lyophilization using methanol and water, the title compound as a white solid (25 mg, 30% yield). $^1$H NMR (300 MHz, DMSO-$d_6$) 8.77 (bs, 1H), 8.70 (d, J=5.3 Hz, 1H), 8.01 (d, J=2.2 Hz, 1H), 7.67 (d, J=8.5 Hz, 1H), 7.59 (d, J=2.1 Hz, 1H), 7.36 (d, J=5.3 Hz, 1H), 7.14 (dd, J=2.1 and 8.5 Hz, 1H), 6.98 (d, J=2.1 Hz, 1H), 1.39 (s, 6H). ESIMS m/z [M+H]$^+$=339.3.

Example 69: 3-tert-butyl-4-[4-(4,4-dimethyl-2,5-dioxo-imidazolidin-1-yl)pyrimidin-2-yl]oxy-benzonitrile

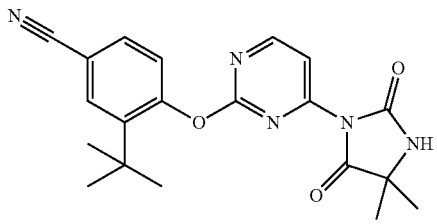 [SMILES: CC1(C)NC(=O)N(c2ccnc(Oc3ccc(C#N)cc3C(C)(C)C)n2)C1=O]

Essentially following the procedures described for example 4-1, using 5,5-dimethyl-3-(2-methylsulfonylpyrimidin-4-yl)imidazolidine-2,4-dione (100 mg, 0.35 mmol) and 3-(tert-butyl)-4-hydroxybenzonitrile (62 mg, 0.35 mmol), to afford, after purification by silica gel chromatography, eluting with a gradient of ethyl acetate:dichloromethane—0:100 to 100:0, semi-preparative purification and a lyophilization using methanol and water, the title compound as a white foam (20 mg, 15% yield). $^1$H NMR (300 MHz, DMSO-$d_6$) 8.80 (bs, 1H), 8.75 (d, J=5.3 Hz, 1H), 7.81 (d, J=1.8 Hz, 1H), 7.74 (dd, J=1.9 and 8.4 Hz, 1H), 7.42 (d, J=5.3 Hz, 1H), 7.35 (d, J=8.4 Hz, 1H), 1.39 (s, 6H), 1.30 (s, 9H). ESIMS m/z [M+H]$^+$=380.3.

Example 70: 4-[4-(4,4-dimethyl-2,5-dioxo-imidazolidin-1-yl)pyrimidin-2-yl]oxy-2-isopropyl-benzonitrile

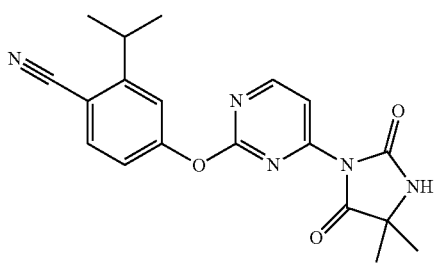 [SMILES: CC(C)c1cc(Oc2nccc(N3C(=O)NC(C)(C)C3=O)n2)ccc1C#N]

Essentially following the procedures described for example 4-1, using 5,5-dimethyl-3-(2-methylsulfonylpyrimidin-4-yl)imidazolidine-2,4-dione (100 mg, 0.35 mmol) and 4-hydroxy-2-isopropyl-benzonitrile (Intermediate 3-5, 57 mg, 0.35 mmol), to afford, after purification by silica gel chromatography, eluting with a gradient of ethyl acetate: dichloromethane—0:100 to 100:0, the title compound as a white foam (70 mg, 68% yield). $^1$H NMR (300 MHz, DMSO-$d_6$) 8.80 (bs, 1H), 8.77 (d, J=5.3 Hz, 1H), 7.84 (d, J=8.5 Hz, 1H), 7.48 (d, J=2.3 Hz, 1H), 7.43 (d, J=5.3 Hz, 1H), 7.31 (dd, J=2.3 and 8.5 Hz, 1H), 3.23 (sept, J=6.8 Hz, 1H), 1.38 (s, 6H), 1.25 (d, J=6.9 Hz, 6H). ESIMS m/z [M+H]$^+$=366.3.

Intermediate 4-5:
4-methyl-3-(trifluoromethoxy)phenol

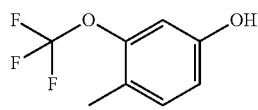

Essentially following the procedures described for intermediate 1-1, using 4-hydroxy-2-(trifluoromethoxy)benzaldehyde (1.44 g, 7.00 mmol) in ethanol/aqueous 12N HCl (50 mL/1.5 mL) to afford, after purification by silica gel flash chromatography eluting with a gradient of cyclohexane:ethyl acetate-100:0 to 60:40 the title compound as a pale yellow oil (1.04 g, 78% yield). 1H NMR (300 MHz, CHCl$_3$-d) 7.08 (d, J=8.3 Hz, 1H), 6.73 (d, J=1.4 Hz, 1H), 6.68 (dd, J=2.5 and 8.3 Hz, 1H), 2.22 (s, 3H).

Example 71: 5,5-dimethyl-3-[2-[4-methyl-3-(trifluoromethoxy)phenoxy]pyrimidin-4-yl]imidazolidine-2,4-dione

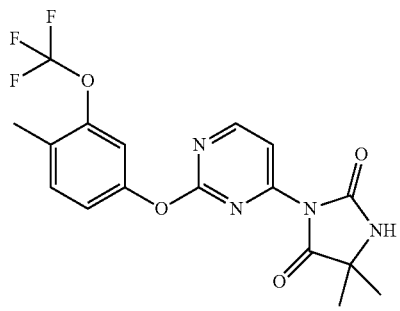

Essentially following the procedures described for example 4-1, using 5,5-dimethyl-3-(2-methylsulfonylpyrimidin-4-yl)imidazolidine-2,4-dione (150 mg, 0.53 mmol) and 4-methyl-3-(trifluoromethoxy)phenol (101 mg, 0.53 mmol), to afford, after purification by silica gel chromatography, eluting with a gradient of ethyl acetate:dichloromethane—0:100 to 100:0, semi-preparative purification and a lyophilization using methanol and water, the title compound as a white solid (100 mg, 47% yield). $^1$H NMR (300 MHz, DMSO-$d_6$) 8.78 (bs, 1H), 8.73 (d, J=5.3 Hz, 1H), 7.44 (d, J=8.5 Hz, 1H), 7.38 (d, J=5.3 Hz, 1H), 7.33 (bs, 1H), 7.23 (dd, J=2.3 and 8.4 Hz, 1H), 2.27 (s, 3H), 1.38 (s, 6H). ESIMS m/z [M+H]$^+$=397.3.

Example 72: 3-[2-(2-methoxy-3-methyl-phenoxy)pyrimidin-4-yl]-5,5-dimethyl-imidazolidine-2,4-dione

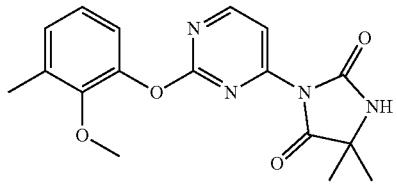

Essentially following the procedures described for example 4-1, using 5,5-dimethyl-3-(2-methylsulfonylpyrimidin-4-yl)imidazolidine-2,4-dione (150 mg, 0.53 mmol) and 2-methoxy-3-methyl-phenol (Intermediate 1-16, 73 mg, 0.53 mmol), to afford, after purification by silica gel chromatography, eluting with a gradient of ethyl acetate:dichloromethane—0:100 to 100:0, semi-preparative purification and a lyophilization using methanol and water, the title compound as a white solid (75 mg, 41% yield). $^1$H NMR (300 MHz, DMSO-$d_6$) 8.78 (bs, 1H), 8.67 (d, J=5.3 Hz, 1H), 7.34 (d, J=5.3 Hz, 1H), 7.15-7.00 (m, 3H), 3.60 (s, 3H), 2.23 (s, 3H), 1.39 (s, 6H). ESIMS m/z [M+H]$^+$=343.3.

Example 73: 3-[2-[(2,2-difluoro-1,3-benzodioxol-5-yl)oxy]pyrimidin-4-yl]-5,5-dimethyl-imidazolidine-2,4-dione

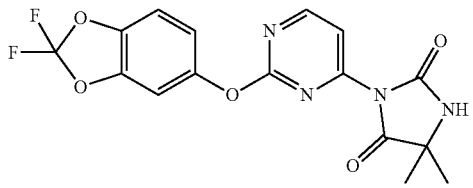 [SMILES: CC1(C)NC(=O)N(c2ccnc(Oc3ccc4c(c3)OC(F)(F)O4)n2)C1=O]

Essentially following the procedures described for example 4-1, using 5,5-dimethyl-3-(2-methylsulfonylpyrimidin-4-yl)imidazolidine-2,4-dione (125 mg, 0.44 mmol) and 2,2-difluoro-1,3-benzodioxol-5-ol (intermediate 1-54, 77 mg, 0.44 mmol), to afford, after purification by silica gel chromatography, eluting with a gradient of ethyl acetate:dichloromethane—0:100 to 100:0 and a lyophilization using methanol and water, the title compound as a white solid (100 mg, 58% yield). $^1$H NMR (300 MHz, DMSO-$d_6$) 8.80 (bs, 1H), 8.72 (d, J=5.3 Hz, 1H), 7.54 (d, J=2.3 Hz, 1H), 7.46 (d, J=8.7 Hz, 1H), 7.39 (d, J=5.3 Hz, 1H), 7.11 (dd, J=2.3 and 8.7 Hz, 1H), 1.39 (s, 6H). ESIMS m/z [M+H]$^+$=379.3.

Intermediate 4-6: 3-(2-methylsulfanylpyrimidin-4-yl)-1,3-diazaspiro[4.5]decane-2,4-dione

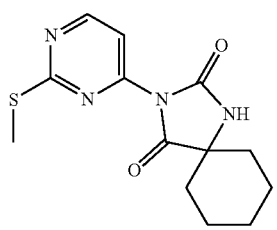 [SMILES: CSc1nccc(N2C(=O)NC3(CCCCC3)C2=O)n1]

Essentially following the procedures described for intermediate 4-3, using 1,3-diazaspiro[4.5]decane-2,4-dione (400 mg, 2.38 mmol), to afford, after purification by silica gel chromatography, eluting with a gradient of ethyl acetate:cyclohexane—0:100 to 100:0 followed by a gradient of methanol:ethyl acetate-0:100 to 10:90, the title compound as a yellow oil (300 mg, 53% yield). ESIMS m/z [M+H]$^+$= 293.3.

Intermediate 4-7: 3-(2-methylsulfonylpyrimidin-4-yl)-1,3-diazaspiro[4.5]decane-2,4-dione

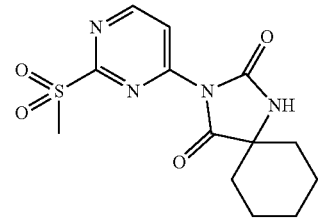 [SMILES: CS(=O)(=O)c1nccc(N2C(=O)NC3(CCCCC3)C2=O)n1]

Essentially following the procedures described for intermediate 4-2, using 3-(2-methylsulfanylpyrimidin-4-yl)-1,3-diazaspiro[4.5]decane-2,4-dione (300 mg, 0.66 mmol), to afford, after purification by silica gel chromatography, eluting with a gradient of ethyl acetate:cyclohexane—0:100 to 100:0 followed by a gradient of methanol:ethyl acetate—0:100 to 10:90, the title compound as a white solid (95 mg, 45% yield). ESIMS m/z [M+H]$^+$=325.2.

Example 74: 3-[2-(3-methoxy-4-methyl-phenoxy)pyrimidin-4-yl]-1,3-diazaspiro[4.5]decane-2,4-dione

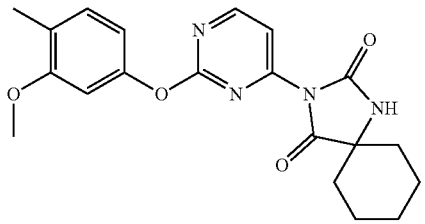 [SMILES: COc1cc(Oc2nccc(N3C(=O)NC4(CCCCC4)C3=O)n2)ccc1C]

Essentially following the procedures described for example 4-1, using 3-(2-methylsulfonylpyrimidin-4-yl)-1,3-diazaspiro[4.5]decane-2,4-dione (95 mg, 0.30 mmol) to afford, after purification by silica gel chromatography, eluting with a gradient of ethyl acetate:cyclohexane—0:100 to 100:0, the title compound as a white solid (70 mg, 61% yield). $^1$H NMR (300 MHz, DMSO-$d_6$) 9.18 (bs, 1H), 8.71 (d, J=5.2 Hz, 1H), 7.33 (d, J=5.2 Hz, 1H), 7.14 (d, J=8.1 Hz, 1H), 6.86 (d, J=2.0 Hz, 1H), 6.69 (dd, J=2.1 and 8.0 Hz, 1H), 3.74 (s, 3H), 2.12 (s, 3H), 1.80-1.48 (m, 9H), 1.40-1.28 (m, 1H). ESIMS m/z [M+H]$^+$=383.3.

Intermediate 4-8: 3-(2-methylsulfanylpyrimidin-4-yl)-1,3-diazaspiro[4.4]nonane-2,4-dione

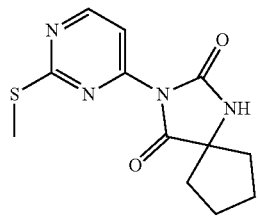 [SMILES: CSc1nccc(N2C(=O)NC3(CCCC3)C2=O)n1]

Essentially following the procedures described for example 1-1, using 1,3-diazaspiro[4.4]nonane-2,4-dione (220 mg, 1.43 mmol), to afford, after purification by silica gel chromatography, eluting with a gradient of dichloromethane:cyclohexane—0:100 to 100:0 followed by a gradient of methanol:dichloromethane—0:100 to 10:90, the title compound as a beige powder (206 mg, 62% yield). ESIMS m/z [M+H]$^+$=279.2.

Intermediate 4-9: 3-(2-methylsulfonylpyrimidin-4-yl)-1,3-diazaspiro[4.4]nonane-2,4-dione

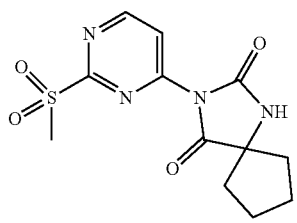 [SMILES: CS(=O)(=O)c1nccc(N2C(=O)NC3(CCCC3)C2=O)n1]

Essentially following the procedures described for intermediate 4-2, using 3-(2-methylsulfanylpyrimidin-4-yl)-1,3-diazaspiro[4.4]nonane-2,4-dione (206 mg, 0.74 mmol), to afford, after purification by silica gel chromatography, eluting with a gradient of methanol:dichloromethane—0:100 to 15:85, the title compound as a white foam (220 mg, 96% yield). ESIMS m/z [M+H]$^+$=311.2.

Example 75: 3-[2-(3-methoxy-4-methyl-phenoxy)pyrimidin-4-yl]-1,3-diazaspiro[4.4]nonane-2,4-dione

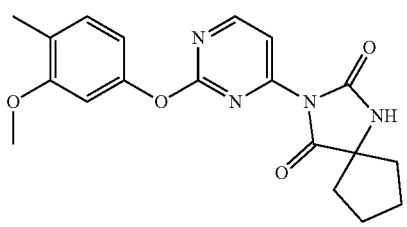 [SMILES: COc1cc(Oc2nccc(N3C(=O)NC4(CCCC4)C3=O)n2)ccc1C]

Essentially following the procedures described for example 4-1, using 3-(2-methylsulfonylpyrimidin-4-yl)-1,3-diazaspiro[4.4]nonane-2,4-dione (220 mg, 0.71 mmol) to afford, after purification by silica gel chromatography, eluting with a gradient of ethyl acetate:cyclohexane—0:100 to 100:0 and a lyophilization using acetonitrile and water, the title compound as a white powder (175 mg, 66% yield). $^1$H NMR (300 MHz, DMSO-d$_6$) 8.97 (bs, 1H), 8.71 (d, J=5.2 Hz, 1H), 7.33 (d, J=5.2 Hz, 1H), 7.14 (d, J=8.1 Hz, 1H), 6.86 (d, J=2.0 Hz, 1H), 6.69 (dd, J=2.1 and 8.0 Hz, 1H), 3.75 (s, 3H), 2.12 (s, 3H), 2.10-1.99 (m, 2H), 1.90-1.72 (m, 6H). ESIMS m/z [M+H]$^+$=369.4.

Intermediate 4-10: 3-(2-methylsulfanylpyrimidin-4-yl)-1,3-diazaspiro[3.4]octane-2,4-dione

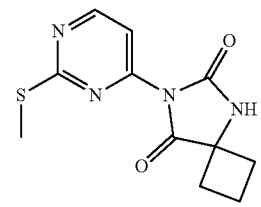 [SMILES: CSc1nccc(N2C(=O)NC3(CCC3)C2=O)n1]

Essentially following the procedures described for example 1-1, using 1,3-diazaspiro[3.4]octane-2,4-dione (200 mg, 1.43 mmol), to afford, after purification by silica gel chromatography, eluting with a gradient of methanol:dichloromethane—0:100 to 10:90, the title compound as a white foam (260 mg, 78% yield). ESIMS m/z [M+H]$^+$=266.1.

Intermediate 4-11: 3-(2-methylsulfonylpyrimidin-4-yl)-1,3-diazaspiro[3.4]octane-2,4-dione

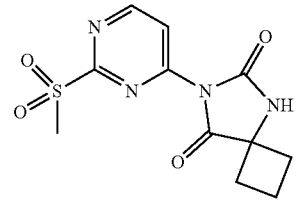 [SMILES: CS(=O)(=O)c1nccc(N2C(=O)NC3(CCC3)C2=O)n1]

Essentially following the procedures described for intermediate 4-2, using 3-(2-methylsulfanylpyrimidin-4-yl)-1,3-diazaspiro[3.4]octane-2,4-dione (260 mg, 0.98 mmol), to afford, after purification by silica gel chromatography, eluting with a gradient of methanol:dichloromethane—0:100 to 10:90, the title compound as a colorless oil (140 mg, 44% yield). ESIMS m/z [M+H]$^+$=297.3.

Example 76: 3-[2-(3-methoxy-4-methyl-phenoxy)pyrimidin-4-yl]-1,3-diazaspiro[3.4]octane-2,4-dione

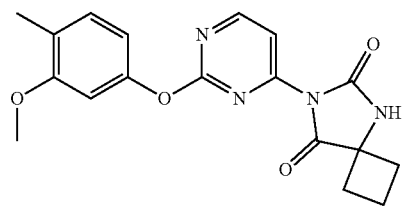 [SMILES: COc1cc(Oc2nccc(N3C(=O)NC4(CCC4)C3=O)n2)ccc1C]

Essentially following the procedures described or example 4-1, using 3-(2-methylsulfonylpyrimidin-4-yl)-1,3- diazaspiro[3.4]octane-2,4-dione (140 mg, 0.47 mmol) to afford, after purification by silica gel chromatography, eluting with a gradient of ethyl acetate:cyclohexane—0:100 to 100:0, the title compound as a white foam (35 mg, 20% yield). $^1$H NMR (300 MHz, DMSO-$d_6$) 9.10 (bs, 1H), 8.71 (d, J=5.2 Hz, 1H), 7.31 (d, J=5.2 Hz, 1H), 7.14 (d, J=8.1 Hz, 1H), 6.86 (d, J=2.0 Hz, 1H), 6.68 (dd, J=2.1 and 8.0 Hz, 1H), 3.75 (s, 3H), 2.60-2.50 (m, 2H), 2.42-2.28 (m, 2H), 2.12 (s, 3H), 2.01-1.90 (m, 1H), 1.89-1.74 (m, 1H). ESIMS m/z $[M+H]^+$=355.3.

Intermediate 5-1: 3-(5-chloropyridazin-3-yl)-5,5-dimethyl-imidazolidine-2,4-dione

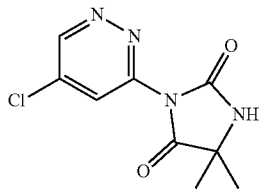 [SMILES: CC1(C)NC(=O)N(c2cc(Cl)cnn2)C1=O]

Essentially following the procedures described for example 1-1, using 3,5-dichloropyridazine (2.0 g, 13.4 mmol) to afford, after purification by by silica gel chromatography eluting with a gradient of methanol:dichloromethane—0:100 to 20:80 the title compound as an orange solid (700 mg, 22% yield). $^1$H NMR (300 MHz, MeOH-$d_4$) 9.70 (s, 1H), 8.25 (d, J=2.1 Hz, 1H), 1.51 (s, 6H). ESIMS m/z $[M+H]^+$=241.3.

Example 77: 3-[5-(3-methoxy-4-methyl-phenoxy)pyridazin-3-yl]-5,5-dimethyl-imidazolidine-2,4-dione

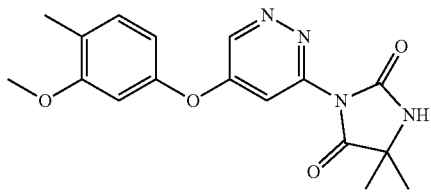

Cesium carbonate (1.14 g, 3.49 mmol) was added to a mixture of 3-(5-chloropyridazin-3-yl)-5,5-dimethyl-imidazolidine-2,4-dione (700 mg, 2.91 mmol) and 3-methoxy-4-methyl-phenol (401 mg, 2.91 mmol) in DMF (5 mL) and the reaction mixture was stirred at 110° C. for 1 hour. The reaction mixture was hydrolyzed in water (100 mL) and the organics were extracted with diethyl ether (2×75 mL). The combined extracts were dried over magnesium sulfate, filtered and the solvent was evaporated in vacuo. The residue was purified by silica gel chromatography eluting with a gradient of ethyl acetate:cyclohexane—0:100 to 100:0 and a semi-preparative purification to afford, after a lyophilization using methanol and water, title compound as white solid (25 mg, 3% yield). $^1$H NMR (300 MHz, DMSO-$d_6$) 9.26 (d, J=1.9 Hz, 1H), 8.90 (bs, 1H), 7.54 (d, J=1.9 Hz, 1H), 7.19 (d, J=8.1 Hz, 1H), 6.85 (d, J=2.2 Hz, 1H), 6.69 (dd, J=2.2 and 8.1 Hz, 1H), 3.75 (s, 3H), 2.14 (s, 3H), 1.39 (s, 6H). ESIMS m/z $[M+H]^+$=343.3.

Cell Biology Protocols and Data
Cell Lines hKv3.1, hKv3.2, hKv3.3, and hKv3.4 were stably expressed in CHO-K1 (Chinese hamster ovary) cells and kept under constant antibiotic selection. For in vitro assays, cells were maintained in appropriate growth medium at 37° C. and 5% $CO_2$ in a humidified incubator.

Electrophysiology
CHO/Kv3.x Cell Preparation hKv3.X expressing cells were plated in T-25 flasks for 3-4 days at 37° C. (no selection antibiotic) prior to use and grown to 80% confluence. Cells were washed twice with PBS (calcium and magnesium free) and detached with a 5-minute treatment at 37° C. with 2-3 mls of Accutase®. Cells were collected, and flask was washed in CHO-SFM II media (Life Technologies Gibco), centrifuged for 2 minutes at ~110×g and resuspended to obtain a single cell suspension of ~2-3×10$^6$ cells/ml.

Solutions and Compound Preparation

The intracellular solution contained the following (in mM): KCl 50, NaCl 10, KF 60, EGTA 20, HEPES 10, adjusted to pH 7.2 with KOH and an osmolarity of 285 mOsmol. Seal enhancer was purchased from Nanion (80 mM NaCl, 3 mM KCl, 10 mM $MgCl_2$, 35 mM $CaCl_2$), 10 mM HEPES, pH7.4, 298 mOsmol. The external solution contained (in mM): NaCl 140, KCl 4, $CaCl_2$) 2, $MgCl_2$ 1, HEPES 10, Glucose 5, adjusted to pH7.4 and an osmolarity of 298 mOsmol.

All compounds were initially tested at 10 uM at a final DMSO concentration of 0.33%. Compounds were dissolved in dimethylsulfoxide (DMSO) at a stock concentration of 30 mM. The compound was further diluted 1:10 to give a stock concentration of 3 mM in DMSO. The final assay solution was diluted 1:300 in External solution to give a final concentration of 10 uM. For the DMSO Control Buffer 30 uL of DMSO was added to 10 mL buffer.

The following voltage protocols were used to assess different hKv3.X channels:

Patchliner Protocol

All electrophysiological recordings were performed at ambient temperature (21-23° C.) using automated patch clamp (Patchliner, Nanion Technologies GmbH) in the whole-cell configuration.

Cell membrane potentials were held at −80 mV, and currents were evoked by voltage steps (1000 ms duration) from −60 to +60 mV in 10 mV increments. This was performed first with vehicle (0.33% DMSO) and then with 10 uM compound, after a 3-minute incubation period. Data was taken from 4 cells per assay.

Data Analysis

The recordings were analysed and selected using peak current amplitude (>100 pA at the −10 mV voltage step) in the absence of compound to eliminate unsuitable cells from analysis. Peak current amplitude was measured and recorded for each voltage step and data was normalised to the maximum current at +60 mV. The normalised Kv3.x currents following addition of the compound were then compared with the currents recorded prior to compound addition (vehicle control). Positive modulation was determined as % potentiation at the voltage step of −10 mV=[current (cmpd)/current (veh)]*100−100. % potentiation≥50% was considered acceptable. In addition, voltage shift of the IV curve at $V_{1/2}$ was measured. $V_{1/2}$ of ≥−5 mV was also considered acceptable. IV curves were plotted in GraphPad Prism (software version 6.0) and fitted with a Boltzmann equation, where $V_{1/2}$ is the voltage at half-maximal activation.

| Example # | Kv3.1 Activity at 10 μM Potentiation (%) | Kv3.1 Activity at 10 μM Voltage Shift (mV) | Kv3.2 Activity at 10 μM Potentiation (%) | Kv3.2 Activity at 10 μM Voltage Shift (mV) |
|---|---|---|---|---|
| 1 | 45 | −5.5 | 25 | −4.3 |
| 2 | 16 | −1.9 | ND | ND |
| 3 | 34 | −2.1 | ND | ND |
| 4 | 25 | −0.9 | ND | ND |
| 5 | 35 | −3.2 | ND | ND |
| 8 | 48 | −3.1 | ND | ND |
| 9 | 22 | −2.2 | ND | ND |
| 10 | 3 | +0.4 | ND | ND |
| 11 | 8 | −1.3 | ND | ND |
| 12 | 13 | −0.3 | ND | ND |
| 13 | 40 | −2.7 | 86 | −9.2 |
| 14 | 43 | −2.3 | 42 | −1.1 |
| 15 | 17 | −2.7 | 1 | −0.3 |
| 16 | 63 | −4.2 | 24 | −2.8 |
| 17 | 7 | −0.2 | ND | ND |
| 18 | 53 | −2.7 | ND | ND |
| 19 | 15 | −1.7 | ND | ND |
| 20 | 37 | −3.3 | ND | ND |
| 21 | 29 | −1.4 | ND | ND |
| 22 | 31 | −2.3 | ND | ND |
| 23 | 28 | −0.9 | ND | ND |
| 24 | 33 | −4.0 | ND | ND |
| 25 | 6 | −0.1 | ND | ND |
| 26 | 17 | −2.2 | ND | ND |
| 27 | −17 | +2.11 | ND | ND |
| 28 | 3 | −1.1 | ND | ND |
| 29 | 10 | −1.6 | ND | ND |
| 30 | 63 | −2.1 | ND | ND |
| 31 | 65 | −3.3 | ND | ND |
| 32 | 13 | −1.3 | ND | ND |
| 33 | 33 | −1.6 | ND | ND |
| 35 | −10 | −0.4 | ND | ND |
| 36 | 17 | −3.3 | ND | ND |
| 37 | 16 | −1.0 | ND | ND |
| 38 | 18 | −2.0 | ND | ND |
| 39 | 13 | −2.1 | ND | ND |
| 40 | 23 | −2.1 | ND | ND |
| 42 | 11 | +2.0 | ND | ND |
| 44 | 33 | −2.9 | ND | ND |
| 45 | 19 | −1.7 | ND | ND |
| 47 | 36 | −2.8 | 54 | −4.9 |
| 48 | 32 | −2.1 | ND | ND |
| 50 | 2 | −1.5 | −7 | +1.6 |
| 53 | 52 | −4.0 | 49 | −6.0 |
| 54 | 15 | −0.5 | ND | ND |
| 55 | 16 | −3.9 | ND | ND |
| 56 | 26 | −5.0 | 35 | −4.6 |
| 57 | −7 | +0.8 | ND | ND |
| 58 | 61 | −6.9 | 39 | −4.6 |
| 59 | 22 | −1.1 | ND | ND |
| 60 | 22 | −2.0 | ND | ND |
| 61 | 21 | −1.6 | ND | ND |
| 62 | 20 | −3.1 | ND | ND |
| 63 | 50 | −4.2 | 25 | −2.3 |
| 64 | 34 | −1.8 | ND | ND |
| 65 | 32 | −2.7 | 35 | −2.8 |
| 66 | ND | ND | 54 | −3.5 |
| 74 | 41 | −3.8 | 12 | −1.6 |
| 77 | 26 | −2.4 | ND | ND |

The invention claimed is:

1. A compound of formula (I):

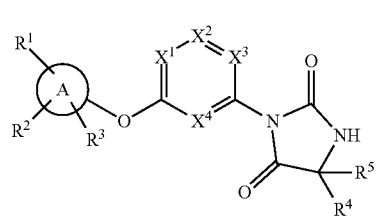

wherein:
$X^1$ and $X^4$ are both N and $X^2$ and $X^3$ are independently CR; or
$X^1$ and $X^3$ are both N and $X^2$ and $X^4$ are independently CR; or
$X^3$ and $X^4$ are both N and $X^1$ and $X^2$ are independently CR; or
$X^1$ and $X^2$ are both N and $X^3$ and $X^4$ are independently CR; or
$X^2$ and $X^3$ are both N and $X^1$ and $X^4$ are independently CR; or
$X^2$ and $X^4$ are both N and $X^1$ and $X^3$ are independently CR; or
$X^1$, $X^3$ and $X^4$ are N and $X^2$ is CR; or
$X^1$, $X^2$ and $X^4$ are N and $X^3$ is CR; or
$X^2$, $X^3$ and $X^4$ are N and $X^1$ is CR; and
Ring A is phenyl or pyridinyl;
$R^1$ is H, CN, halo, $OCF_3$, optionally substituted $C_1$-$C_5$ alkoxy, optionally substituted $C_1$-$C_5$ alkyl, optionally substituted aryl or optionally substituted heteroaryl;
$R^2$ and $R^3$ are independently H, CN, halo, optionally substituted $C_1$-$C_5$ alkyl or optionally substituted $C_1$-$C_5$ alkoxy; or
$R^2$ and $R^3$ together represent an optionally substituted 5- or 6-membered O, N or S-containing heterocyclyl; and
$R^4$ and $R^5$ are independently H, optionally substituted $C_1$-$C_4$ alkyl or optionally substituted $C_1$-$C_4$ haloalkyl; or
$R^4$ and $R^5$ together represent an optionally substituted 3-, 4-, 5-, 6- or 7-membered cycloalkyl or optionally substituted 3-, 4-, 5-, 6- or 7-membered heterocyclyl;
R is selected from H, halo, $C_1$-$C_3$ haloalkyl, $C_1$-$C_5$ alkoxy or $C_1$-$C_5$ alkyl;
or a pharmaceutically acceptable salt, solvate or prodrug thereof, and stereoisomer thereof.

2. A compound according to claim 1 which is represented by formula (II):

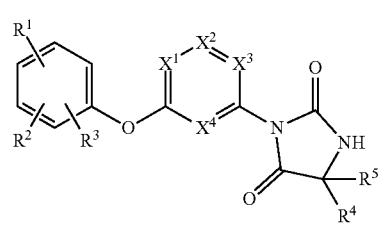

wherein:
$X^1$ and $X^4$ are both N and $X^2$ and $X^3$ are independently CR; or $X^1$ and $X^3$ are both N and $X^2$ and $X^4$ are independently CR; or
$X^3$ and $X^4$ are both N and $X^1$ and $X^2$ are independently CR; or
$X^1$ and $X^2$ are both N and $X^3$ and $X^4$ are independently CR; or
$X^2$ and $X^3$ are both N and $X^1$ and $X^4$ are independently CR; or
$X^2$ and $X^4$ are both N and $X^1$ and $X^3$ are independently CR; or
$X^1$, $X^3$ and $X^4$ are N and $X^2$ is CR; or
$X^1$, $X^2$ and $X^4$ are N and $X^3$ is CR; or
$X^2$, $X^3$ and $X^4$ are N and $X^1$ is CR; and
$R^1$ is H, CN, halo, $OCF_3$, optionally substituted $C_1$-$C_5$ alkoxy, optionally substituted $C_1$-$C_5$ alkyl, optionally substituted aryl or optionally substituted heteroaryl;
$R^2$ and $R^3$ are independently H, CN, halo, optionally substituted $C_1$-$C_5$ alkyl or optionally substituted $C_1$-$C_5$ alkoxy; or
$R^2$ and $R^3$ together represent an optionally substituted 5- or 6-membered O, N, S-containing heterocyclyl; and
$R^4$ and $R^5$ are independently H, optionally substituted $C_1$-$C_4$ alkyl or optionally substituted $C_1$-$C_4$ haloalkyl; or
$R^4$ and $R^5$ together represent an optionally substituted 3-, 4-, 5-, 6- or 7-membered cycloalkyl or optionally substituted 3-, 4-, 5-, 6- or 7-membered heterocyclyl; and
R is selected from H, halo, $C_1$-$C_3$ haloalkyl, $C_1$-$C_5$ alkoxy or $C_1$-$C_5$ alkyl;
or a pharmaceutically acceptable salt, solvate or prodrug thereof, and stereoisomer thereof.

3. The compound of claim 2, wherein the compound of formula (II) is a compound of formula (IIa), (IIb), or (IIc):

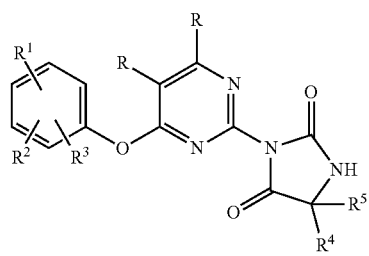
(IIa)

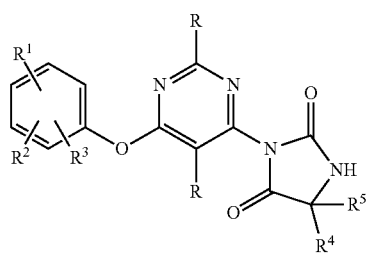
(IIb)

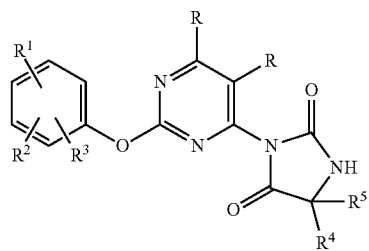
(IIc)

wherein R and $R^1$ to $R^5$ are as defined.

4. The compound of claim 2, wherein the compound of formula (II) is a compound of formula (IId), (IIe), or (IIf):

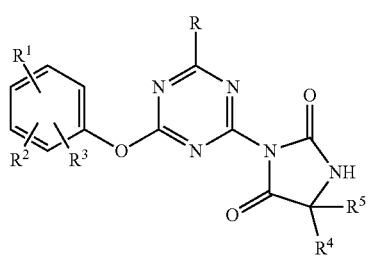
(IId)

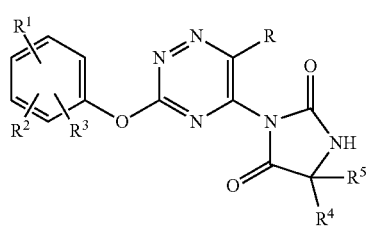
(IIe)

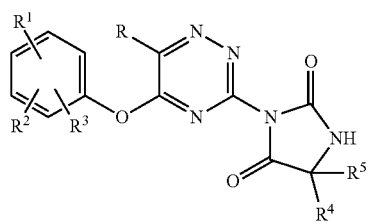
(IIf)

wherein R and $R^1$ to $R^5$ are as defined.

5. A compound according to claim 1 which is represented by formula (III) is a compound of formula (IIIa), (IIIb), or (IIIc):

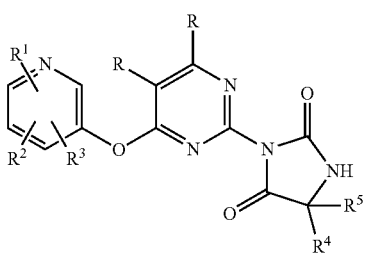
(IIIa)

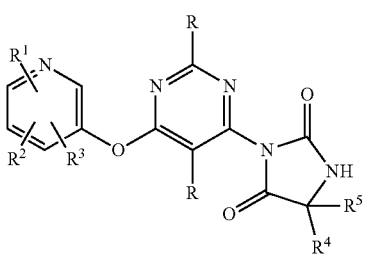
(IIIb)

(IIIc)

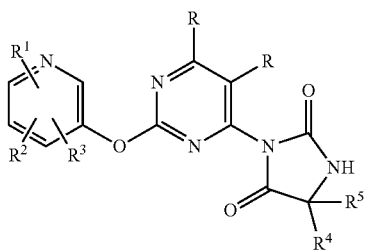

wherein R and R¹ to R⁵ are as defined above.

6. A compound according to claim 1 which is represented by formula (III) is a compound of formula (IIId), (IIIe), or (IIIf):

(IIId)

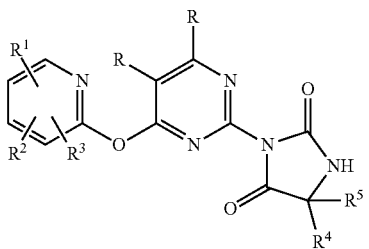

(IIIe)

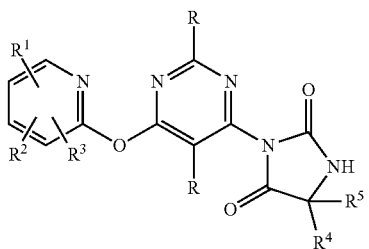

(IIIf)

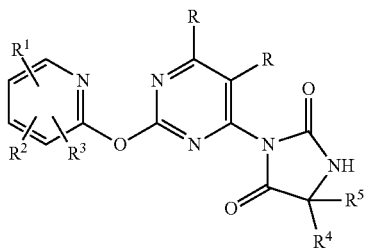

wherein R and R¹ to R⁵ are as defined above.

7. A compound according to claim 1 which is represented by formula (III) is a compound of formula (IIIg), (IIIh), or (IIIi):

(IIIg)

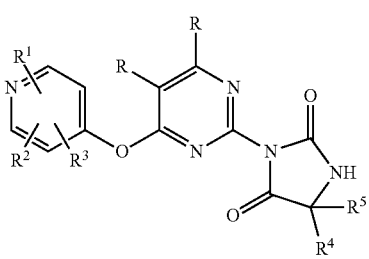

(IIIh)

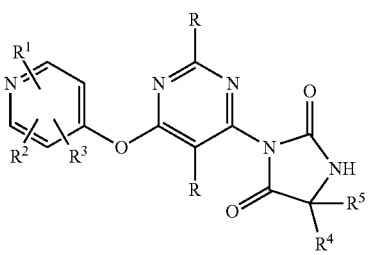

(IIIi)

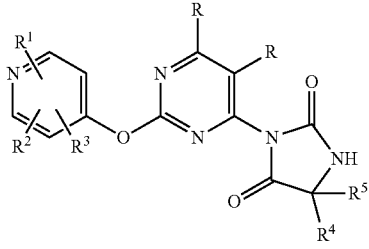

wherein R and R¹ to R⁵ are as defined above.

8. A compound according to claim 1 which is represented by formula (III) is a compound of formula (IIIj), (IIIk), (IIIl), (IIIm), (IIIn), (IIIo), (IIIp), (IIIq) or (IIIr):

(IIIj)

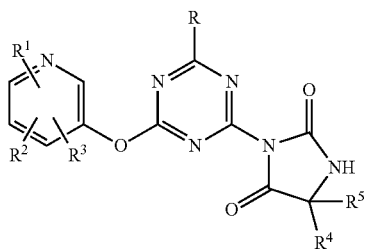

(IIIk)

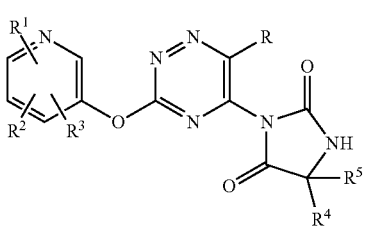

(IIIl)

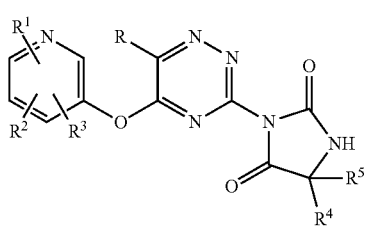

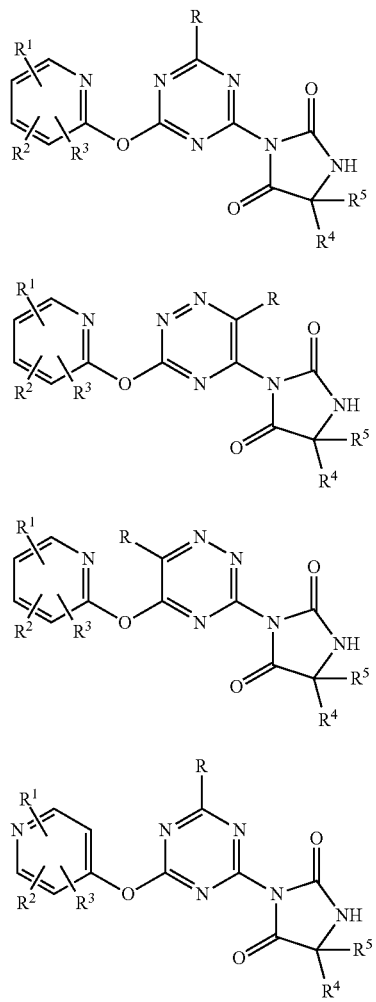

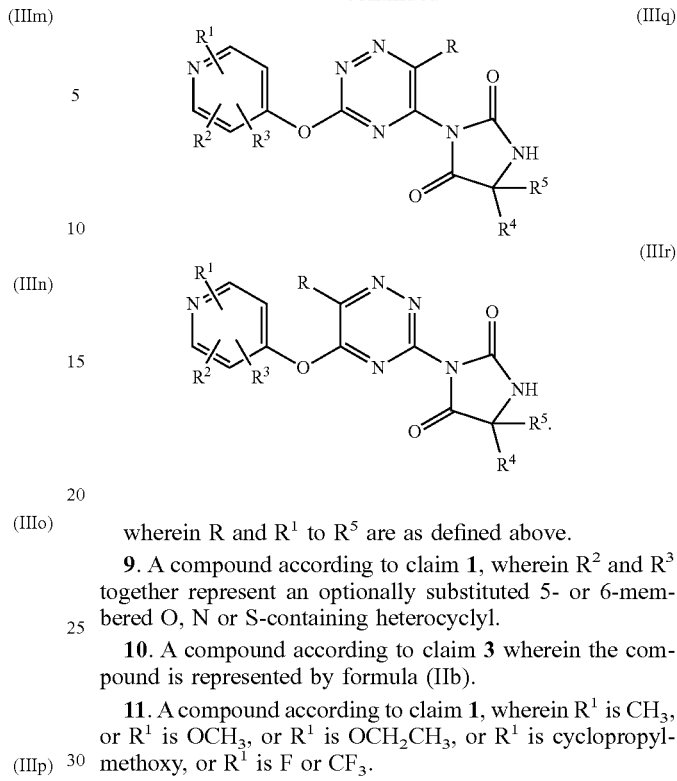

wherein R and $R^1$ to $R^5$ are as defined above.

9. A compound according to claim 1, wherein $R^2$ and $R^3$ together represent an optionally substituted 5- or 6-membered O, N or S-containing heterocyclyl.

10. A compound according to claim 3 wherein the compound is represented by formula (IIb).

11. A compound according to claim 1, wherein $R^1$ is $CH_3$, or $R^1$ is $OCH_3$, or $R^1$ is $OCH_2CH_3$, or $R^1$ is cyclopropylmethoxy, or $R^1$ is F or $CF_3$.

12. A compound according to claim 1, wherein $R^2$ is H or $CH_3$, or $R^2$ is H, F or $CF_3$, or $R^2$ is $OCH_3$, or $R^2$ is $OCF_3$.

13. A compound according to claim 1, wherein $R^3$ is H or $CH_3$, or $R^3$ is H, F or $CF_3$, or $R^3$ is $OCH_3$, or $R^3$ is $OCF_3$, or $R^2$ and $R^3$ together is an optionally substituted tetrahydrofuranyl ring.

14. A compound according to claim 1, wherein $R^4$ is $CH_3$ and $R^5$ is $CH_3$, or $R^4$ is $CH_3$ and $R^5$ is H.

* * * * *